United States Patent
McAllister et al.

(10) Patent No.: US 9,695,436 B2
(45) Date of Patent: Jul. 4, 2017

(54) PLANTS HAVING ENHANCED NITROGEN USE EFFICIENCY AND METHODS OF PRODUCING SAME

(71) Applicant: Bayer CropScience LP, Research Triangle Park, NC (US)

(72) Inventors: Chandra McAllister, Edmonton (CA); Perrin Beatty, Edmonton (CA); Jayne D'Entremont, Barriere (CA); Allen Good, Edmonton (CA)

(73) Assignee: BAYER CROPSCIENCE LP, Durham, NC (US)

( * ) Notice: Subject to any disclaimer, the term of this patent is extended or adjusted under 35 U.S.C. 154(b) by 0 days.

(21) Appl. No.: 14/772,276

(22) PCT Filed: Mar. 4, 2014

(86) PCT No.: PCT/EP2014/054171
§ 371 (c)(1),
(2) Date: Sep. 2, 2015

(87) PCT Pub. No.: WO2014/135535
PCT Pub. Date: Sep. 12, 2014

(65) Prior Publication Data
US 2016/0010102 A1    Jan. 14, 2016

Related U.S. Application Data
(60) Provisional application No. 61/773,770, filed on Mar. 6, 2013.

(51) Int. Cl.
*C12N 5/14* (2006.01)
*C12N 15/82* (2006.01)
*C12N 9/10* (2006.01)

(52) U.S. Cl.
CPC ....... *C12N 15/8261* (2013.01); *C12N 9/1096* (2013.01); *C12N 5/14* (2013.01); *C12Y 206/01002* (2013.01)

(58) Field of Classification Search
None
See application file for complete search history.

(56) References Cited

U.S. PATENT DOCUMENTS

| 4,634,674 | A | 1/1987 | Shahin | |
| 7,589,257 | B2 | 9/2009 | Hershey et al. | |
| 2003/0233675 | A1* | 12/2003 | Cao | C07K 14/195 800/279 |
| 2005/0044585 | A1 | 2/2005 | Good et al. | |
| 2007/0162995 | A1* | 7/2007 | Good | C12N 9/1096 800/278 |
| 2009/0288224 | A1 | 11/2009 | Good et al. | |

FOREIGN PATENT DOCUMENTS

WO    WO 2013/033846 A1    3/2013

OTHER PUBLICATIONS

Ward et al 2000 (Journal of Bacteriology 182: p. 2559-2566).*
GenBank Accession No. Z26322.1, "H.vulgare mRNA for alanine aminotransferase," http://www.ncbi.nlm.nih.gov/nuccore/Z26322, last update Jun. 12, 2006 (2 pages).
Beatty et al., "Transcriptome analysis of nitrogen-efficient rice over-expressing alanine aminotransferase," Plant Biotechnology Journal, vol. 7, 2009, pp. 562-576.
Burton et al., "Over-expression of specific HvCsIF cellulose synthase-like genes in transgenic barley increases the levels of cell wall (1,3:1,4)-β-D-glucans and alters their fine structures," Plant Biotech Jor. vol. 9, 2011, pp. 117-135.
Dellapenna, Plant Metabolic Engineering, Plant Physiology vol. 125 pp. 160-163.
Duff et al., "The Enzymology of alanine aminotransferase (AlaAT) isoforms from Hordeum vulgare and other organisms, and the HvAlaAT crystal structure," Archives of Biochemistry and Biophysics, vol. 528, 2012, pp. 90-101.
GenBank Accession No. 1X19_A, "Chain A, Alanine Aminotransferase From Pyrococcus Furiosus Pfu-1397077-001," http://ww.ncbi.nlm.gov/protein/1x19_A, last udate Oct. 9, 2012. (3 pages).
GenBank Accession No. AAK98527.1, "alanine aminotransferase-like protein [Thermococcus litoralis]," http://www.ncbi.nlm.nih.gov/protein/AAK98527.1, last update date Sep. 5, 2011 (2 pages).
GenBank Accession No. ACJ15716.1, "alanine aminotransferase [Thermococcus onnurineus NA1]," http://www.ncbi.nlm.nih.gov/protein/ACJ15716.1, last updated Jan. 31, 2014 (2 pages).
GenBank Accession No. ACS33579.1, "Alanine aminotransferase (aat) [Thermococcus gammatolerans EJ3]," last update date Jun. 25, 2015, (3 pages).
GenBank Accession No. ACS90484.1, Alanine aminotransferase [Thermococcus sibiricus MM 739], http://www.ncbi.nlm.nih.gov/protein/ACS90484.1, last updated date Jan. 30, 2014 (2 pages).
GenBank Accession No. ADT83250.1, "aspartate aminotransferase [Thermococcus barophilus MP]," http://www.ncbi.nih.gov/ADT83250.1, last updated date Jan. 31, 2014 (2 pages).
GenBank Accession No. AEC52815.1, "alanine aminotransferase [*Pyrococcus* sp. NA2]," http://www.ncbi.nlm.nih.gov/protein/AEC52815.1, last updated date Jan. 31, 2014 (2 pages).
GenBank Accession No. AEH24862.1, "alanine aminotransferase [Pyrococcus yayanosii CH1]," http://www.ncbi.nlm.nih.gov/protein/AEH24862.1, last update date Jan. 31, 2014, (2 pages).
GenBank Accession No. AEK72704.1 "alanine aminotransferase [*Thermococcus* sp. 4557]," http://www.ncbi.nlm.nih.gov/protein/AEK72704.1, last update date Jan. 31, 2014 (2 pages).
GenBank Accession No. AFK22834.1, "alanine aminotransferase [*Pyrococcus* sp. ST04]," http:www.ncbi.nih.gov/protein/AFK228341, last updated date Jan. 31, 2014 (2 pages).
GenBank Accession No. AFL94660.1, "putative aminotransferase 2[Thermococcus cleftensis]," http://www.ncbi.nhi.gov/protein/AFL94660.1, last update date Jan. 31, 2014 (2 pages).
GenBank Accession No. BAD85283.1, "alanine aminotransferase [Thermococcus kodakarensis KOD1]," http://www.nicbi.nlm.nih.gov/protein/BAD85283.1, last update date May 19, 2007 (2 pages).

(Continued)

*Primary Examiner* — Matthew Keogh
(74) *Attorney, Agent, or Firm* — Arent Fox LLP

(57) ABSTRACT

Methods are provided for enhancing yield and nitrogen use efficiency in plants, and to methods of increasing biomass and seed yield in plants grown under nitrogen limiting conditions using variants of enzymes involved in nitrogen assimilation or metabolism from non-plant organisms.

15 Claims, 16 Drawing Sheets

(56) References Cited

OTHER PUBLICATIONS

GenBank Accession No. EEB72915.1, Aspartate aminotransferase [*Thermococcus* sp. AM4], http://www.ncbi.nlm.nih.gov/protein/EEP72915.1, last update date Jan. 31, 2014 (2 pages).
GenBank Accession No. NM_001021084.1, "Schizosaccharomyces pornbe 972h-alanine aminotransferase (predicted) (SPBC582.08), mRNA," http://www.ncbi.nih.gov/nuccore/NM_001021084.1, last updated date Aug. 5, 2011 (3 pages).
GenBank Accession No. NM_001071039.1, "*Oryza sativa* Japonica Group Os10g0390500 (Os10g0390500) mRNA, complete cds," http://www.ncbi.nih.gov/nuccore/NM_001071039.1, last update date Jun. 8, 2010 (4 pages).
GenBank Accession No. NM_001083740.1, "Bos taurus glutamic-pyruvate transaminase (alanine aminotransferase) (GPT), mRNA," http://www.ncbi.nlm.nih.gov/nuccore/NM_001083740.1, last updated date Jul. 14, 2012 (3 pages).
GenBank Accession No. NM_001142774.1, "Danio rerio glutamic pyruvate transaminase (alanine aminotransferase) 2, like (gpt2l), mRNA," http://www.ncbi.nih.gov/nuccore/NM_001142774.1, last update Sep. 28, 2014 (3 pages).
GenBank Accession No. NM_001181976.1, "*Saccharomyces cerevisiae* S288c alanine transaminase ALT1 (ALT1), mRNA," http://www.ncbi.nlm.nih.gov/nuccore/NM_001181976.1, last update date Jun. 14, 2015 (3 pages).
GenBank Accession No. NM_005309.2, "*Homo sapiens* glutamic-pyruvate transaminase (alanine aminotransferase) (GPT), mRNA," http://www.ncbi.nlm.nih.gov/nuccore/NM_187761304/?report=genbank, last update date Mar. 15, 2015 (5 pages).
GenBank Accession No. NM_031039.1, "Rattus norvegicus glutamic-pyruvate transaminase (alanine aminotransferase) (Gpt), mRNA," http://www.ncbi.nlm.nih.gov/nuccore/NM_031039.1, last update date Aug. 10, 2014 (3 pages).
GenBank Accession No. NM_101591.5, "*Arabidopis thaliana* alanine aminotransferase mRNA, complete cds," http://www.ncbi.nlm.nih.gov/nuccore/NM_101591.5, last update date Jan. 22, 2014 (4 pages).
GenBank Accession No. NM_105892.4, "*Arabiodopsos thaliana* alanine aminotransferase 2 mRNA, complete cds,"http://www.ncbi.nlm.nih.gov/nuccore/NM_105892.4, last update date Jan. 22, 2014 (3 pages).
GenBank Accession No. NM_182805.2, "Mus musculous glutamic pyruvic transaminase, soluable (Gpt), mRNA," http://www.ncbi.nlm.nih.gov/nuccore/NM_182805.2, last update date Feb. 15, 2015 (4 pages).
GenBank Accession No. NP_001064504.1, "Os10g0390500 [*Oryza sativa* Japonica Group]," http://www.ncbi.nlm.nih.gov/protein/NP_001064504.1, last update date Jun. 8, 2010 (4 pages).
GenBank Accession No. NP_001077209.1, alanine aminotransferase 1 [Bos Taurus], http://www.ncbi.nlm.nih.gov/protein/NP_001077209.1, last update date Jan. 4, 2014 (3 pages).
GenBank Accession No. NP_001136246.1, "alanine aminotransferase 2-like [Danio rerio]," http://www.ncbi.nlm.nih.gov/protein/NP_001136426.1, last update date Sep. 28, 2014 (3 pages).
GenBank Accession No. NP_005300.1, "alanine aminotransferase 1[*Homo sapiens*]," http://www.ncbi.nlm.nih.gov/protein/NP_005300.1, last update date Mar. 15, 2015 (4 pages).
GenBank Accession No. NP_013190.1, "alanine transaminase ALT1 [*Saccharomyces cerevisiae* S288c]," http://www.ncbi.nlm.nih.gov/protein/NP_013190.1, last update date Jun. 14, 2015 (3 pages).
GenBank Accession No. NP_112301.1, "alanine aminotransferase 1[Rattus norvegicus]," http://www.ncbi.nlm.nih.gov/protein/NP_112301.1, last update date Aug. 10, 2014 (3 pages).
GenBank Accession No. NP_126507.1, "alanine aminotransferase [Pyrococcus abyssi GE5]," http://www.ncbi.nlm.nih.gov/protein/NP_126507.1?report=genpept, last update date Dec. 16, 2014 (2 pages).
GenBank Accession No. NP_143210.1, "alanine aminotransferase [Pyrococcus horikoshii OT3]," http://www.ncbi.nlm.nih.gov/protein/NP_143210.1?report=genpept, last update Dec. 16, 2014 (2 pages).
GenBank Accession No. NP_173173.3, "alanine aminotransferase [*Arabidopsis thaliana*]," http://www.ncbi.nlm.nih.gov/protein/NP_173173.3, last update date Jan. 22, 2014 (4 pages).
GenBank Accession No. NP_565040.2, "alanine aminotransferase 2 [*Arabidopsis thaliana*]," http://www.ncbi.nlm.nih.gov/protein/NP_565040.2, last update Jan. 22, 2014 (3 pages).
GenBank Accession No. NP_579226.1, "alanine aminotransferase [Pyrococcus furious DSM 3638]," http://www.ncbi.nlm.nih.gov/protein/NP_579226.1?report=genpept, last update date Dec. 16, 2014 (2 pages).
GenBank Accession No. NP_595176.1, "alanine aminotransferase (predicted) [Schizosaccharomyces pombe 972h-2]," http://www.ncbi.nlm.nih.gov/protein/NP_595176.1, last updated date May 1, 2013 (3 pages).
GenBank Accession No. NP_776291.1, "alanine aminotransferase 2 [Mus musculus]," http://www.ncbi.nlm.nih.gov/protein/NP_776291.1, last update Apr. 10, 2015, (3 pages).
GenBank Accession No. NP_877957.1, "alanine aminotransferase 1[Mus musculus]," http://www.ncbi.nlm.nih.gov/protein/NP_877957.1, last update date Feb. 15, 2015 (3 pages).
GenBank Accession No. XM_001093616.2, "Predicted: Macaca mulatta glutamic-pyruvate transamine (alanine aminotransferase), transcript variant 1 (GPT), mRNA," http://www.ncbi.nlm.nih.gov/nuccore/XM_001093616.2?report=genbank, last update date Jun. 1, 2010 (2 pages).
GenBank Accession No. XM_001919861.2, "Predicted: Danio renio alanine aminotransferase 2-like (LOC100148522), mRNA," http://www.ncbi.nlm.nih.gov/nuccore/XM_001919861.2, last update date Mar. 23, 2011 (2 pages).
GenBank Accession No. XM_369988.2, "Megnaporthe Oeyzae 70-15 conserved hypothetical protein (MGG_06503) partial mRNA," http://www.ncbi.nlm.nih.gov/nuccore/XM_369988.2?report =genbank, last update date May 17, 2010 (2 pages).
GenBank Accession No. XM_455940.1, "Kluyveromyces lactis NRRL Y-1140 hypothetical protein partial mRNA," http://www.ncbi.nlm.nih.gov/nuccore/XM_455940.1, last updated date Aug. 5, 2010 (3 pages).
GenBank Accession No. XM_847258.2, "Predicted: Canis lupis familiaris glutamic-pyruvate transaminase (alanine aminotransferase) (GPT), mRNA," http://www.ncbi.nlm.nih.gov/nuccore/XM_847258.2?report =genbank, last update Dec. 2, 2011 (2 pages).
GenBank Accession No. XM_952519.2, "Neurospora crassa OR74A hypothetical protein NCU03973 partial mRNA," last update Apr. 10, 2008 (3 pages).
GenBank Accession No. XP_001093616.1, "Predicted: alanine aminotransferase 1 isoform 1 [Macaca Mulatta]," http://www.ncbi.nlm.nih.gov/protein/XP_001093616.1?report=genpept, last updated date Jun. 1, 2010 (2 pages).
GenBank Accession No. XP_001919896.1, "Predicted: alanine aminotransferase 1 [Danio rerio]," http://www.ncbi.nlm.nih.gov/protein/XP_001919896.1, last update date Sep. 24, 2014.
GenBank Accession No. XP_369988.2, "conserved hypothetical protein [Magnaporthe oryzae 70-15]," http://www.ncbi.nih.gov/protein/XP_369988.2?report=genpept, last updated date May 17, 2010 (2 pages).
GenBank Accession No. XP_455940.1, "hypothetical protein [Kluyveromyces lactis NRRL Y-1140]," http://www.ncbi.nih.gov/protein/XP_455940.1, last updated date Aug. 5, 2010 (3 pages).
GenBank Accession No. XP_852351.2, "Predicted: alaninetransferase 1 [Canis lupus familiaris]," http://www.ncbi.nih.gov/protein/XP_852351.2?report=genpept, last updated date Dec. 2, 2011 (2 pages).
GenBank Accession No. XP_957612.1, "hypothetical protein NCU03973 [Neurospora crassa OR74A]," http://www.ncbi.nih.gov/protein/XP_957612.1, last updated date Apr. 10, 2008 (2 pages).

(56) References Cited

OTHER PUBLICATIONS

GenBank Accession No. YP_002306613.1, "alanine aminotransferase [Thermococcus onnurineus NA1]," http://www.ncbi.nih.gov/protein/YP_002306613.1?report=genpept, last updated date Dec. 17, 2014 (2 pages).
GenBank Accession No. YP_002581272.1, "aspartate aminotransferase [*Thermococcus* sp. AM4]," http://www.ncbi.nih.gov/protein/YP_002581272.1?report=genpept, last updated date Dec. 17, 2014 (2 pages).
GenBank Accession No. YP_00295443.1, "alanine aminotransferase [Thermococcus gammatolerans EJ3]," http://www.ncbi.nih.gov/protein/YP_002959443.1, last updated date Dec. 17, 2014 (3 pages).
GenBank Accession No. YP_002994833.1, "Alaninen aminotransferase [Thermococcus sibiricus MM 739]," http://www.ncbi.nih.gov/protein/YP_002994833.1?report=genpept, last updated date Dec. 17, 2014 (2 pages).
GenBank Accession No. YP_004070473.1, "aspartate aminotransferase [Thermococcus barophilus MP]," http://www.ncbi.nih.gov/protein/YP_004070473.1?report=genpept, last updated date Dec. 17, 2014 (2 pages).
GenBank Accession No. YP_004424819.1, "alanine aminotransferase [*Pyrococcus* sp. NA2]," http://www.ncbi.nih.gov/protein/YP_004424819.1?report=genpept, last updated date Dec. 17, 2014 (2 pages).
GenBank Accession No. YP_004624134.1, "alanine aminotransferase [Pyrococcus yayanosii CH1]," http://www.ncbi.nlh.gov/protein/YP_004624134.1?report=genpept, last updated date Dec. 17, 2014 (2 pages).
GenBank Accession No. YP_006354909.1, "alanine aminotransferase [*Pyrococcus* sp. ST04]," http://www.ncbi.nlh.gov/protein/YP_006354909.1?report=genpept, last updated date Dec. 17, 2014 (2 pages).
GenBank Accession No. YP_006424454.1, "putative aminotransferase 2 [Thermococcus cleftensis]," http://www.ncbi.nlh.gov/protein/YP_006424454.1, last updated date Dec. 17, 2014 (2 pages).
GenBank Accession No. YP_183507.1, "alanine aminotransferase [Thermococcus kodakarensis KOD1]," http://www.ncbi.nlh.gov/protein/YP_183507.1?report=genpept, last updated date Dec. 17, 2014 (2 pages).
GenBank Accession No. ZP_09730551, "alanine aminotransferase [Thermococcus litoralis DSM 5473]," http://www.ncbi.nlh.gov/protein/ZP_09730551.1?report=genpept, last updated date Feb. 9, 2012 (2 pages).
GenBank Accession No. ZP_11216073.1, "alanine aminotransferase [Thermococcus zilligii AN1]," http://www.ncbi.nlh.gov/protein/ZP_11216073.1, last updated date Oct. 16, 2012 (2 pages).
Good et al., "Biotechnology Approaches to Improving Nitrogen Use Efficient in Plants: Alanine Aminotransferase as a Case Study," The Molecular and Physiological Basis of Nutrient Use Efficiency in Crops, Frist Edition, 2011, pp. 165-191.
Good et al., "Can less yield more? Is reducing nutrient input into the environment compatible with maintaining crop production?" TRENDS in Plant Science, vol. 9, Dec. 2004, pp. 597-605.
Good et al., "Engineering nitrogen use efficiency with alanine aminotransferase," Canadian Journal of Botany, vol. 85, 2007, pp. 252-262.
Good et al., "Fertilizing Nature: A Tragedy of Excess in the Commons," Plos Biol., 2011, vol. 9, pp. 1-9.
Green et al., "Generation of up-regulated allosteric variants of potato ADP-glucose pyrophosphorylase by reversion genetics," Proc. Natl. Acad. Sci. USA, vol. 95, Aug. 1998, pp. 10322-10327.
Harrison et al., "A rapid and robust method of identifying transformed *Arabidopsis thaliana* seedlings 1 following floral dip transformation," Plant Methods, vol, 2, 2006, pp. 1-7.
Kasuga et al "Improving plant drought, salt, and freezing tolerance by gene transfer of a single stress-inducible transcription factor." Nature Biotechnology, vol. 17, Mar. 1999, pp. 287-291.

Lock, "Engineering nitrogen use efficiency in *Oryza sativa* by the development over-expression of barley alanine aminotransferase using a novel rice promoter," Master of Science thesis. University of Alberta, Edmonton, Alberta, Canada, 2011, pp. 1-151.
McAllister at al., "Analysis of the Enzymatic Properties of a Broad Family of Alanine Aminotransferases," PLOS One, vol. 8, Feb. 2013, pp. 1-9.
McAllister et al., "Engineering nitrogen use efficient crop plants: the current status," Plant Biotech. Jour., (2012), 10, pp. 1011-1025.
Miyashita et al., "NAD(H)-dependent glutamate dehydrogenase is essential for the survival of *Arabidopsis thaliana* during dark-induced carbon starvation," J. of Experimental Botany, vol. 59, 2008, pp. 667-680.
Muench et al., "Hypoxically Inducible barley alanine aminotransferase: cDNA cloning and expression analysis," Plant Molecular Biology, vol. 24, 1994, pp. 417-427.
Napoli et al., "Introduction of a Chimeric Chalcone Synthase Gene into Petunia Results in Reversibie Co-Suppression of Homologous Genes in trans," The Plant Cell, vol. 2, 1990, pp. 279-289.
Needleman et al., "A General Method Applicable to the Search for Similarities in the Amino Acid Sequence of Two Proteins," J. Mol. Biol. (1970) vol. 48, pp. 443-453.
Oguchi et al., "Methylmalonate-semialdehyde dehydrogenase is induced in auxin-stimulated and zinc-stimulated root formationrice," Plant Cell Rep (2004) vol. 22, pp. 848-858.
Paine et al., "Improving the nutritional value of Golden Rice through increased pro-vitamin A content," Nat. Biotechnol., vol. 23, 2005, pp. 482-487.
Pearson et al., "Improved tools for biological sequence comparison," Proc. Natl. Acad. Sci. USA, vol. 85, Apr. 1988. pp. 2444-2448.
Pino et al., "Use of a stress inducible promoter to drive ectopic AtCBF expression improves potato freezing tolerance while minimizing negative effects on tuber yield," Plant Biotech, Jour. (2007), 5, pp. 591-604.
Qu et al., "Evaluation of tissue specificity and expression strength of rice seed component gene promoters in transgenic rice," Plant Biotechnology Journal, vol. 2, 2004, pp. 113-125.
Rus et al., "Natural Variants of AtHKT1 Enhance Na Accumulation in Two Wild Populations of *Arahidopsis*," PLoS Genetics, Dec. 2006, vol. 2, pp. 1964-1973.
Shelton et al., "Economic, Ecological, Food Safety, and Social Consequences of the Deployment of BT Transgenic Plants," Annu. Rev. Entomol, vol. 47, 2002, pp. 845-881.
Shrawat et al., "Agrobacterium tumefaciens-Mediated Genetic Transformation of Cereals Using Immature Embryos," Methods in molecular biology, vol. 710, 2011, pp. 355-372.
Shrawat et al., "Genetic engineering of improved nitrogen use efficiency in rice by the tissue-specific expression of alanine aminotransferase," Plant Biotechnological Journal (2008), vol. 6, pp. 722-732.
Smith et al., Comparison of Biosequences, Advances in Applied Mathematics, vol. 2, 1981, pp. 482-489.
Tanaka et al., "Proteome Approach to Characterize that Methylmalonate-Semialdehyde Dehydrogenase that Is Regulated by Gibberellin," J. of Proteome Research, vol. 4, 2005, pp. 1575-1582.
Tao et al., "Milestones in directed enzyme evolution," Current Opinion in chemical biology, vol. 6, pp. 858-864.
Yanagisawa et al., "Dof1 and Dof2 transcription factors are associated with expression of multiple gene involved in carbon metabolism in maize," The Plant Journal, vol. 21, 2000, pp. 281-288.
Yanaglsawa et al., "Metabolic: engineering with Dof1 transcription factor in plants: Improved nitrogen assimilation and growth under low-nitrogen conditions," 2004, PNAS, vol. 101 pp. 7833-7838.
Yang et al., "Alanine aminotransferase isoenzymes: molecular cloning and quantitative analysis of tissue expression in rats and serum elevation in liver toxicity," Hepatology, Feb. 2009, vol. 49, pp. 598-607.
Zhang et al., "An Engineered Monolignol 4-0-Methyltransferase Depresses Lignin Biosynthesis and Confers Novel Metabolic Capability in Arabidopsis," The Plant Cell, vol. 24, Jul. 2012, pp. 3135-3152.

\* cited by examiner

Figure 1.

Components of the expression vectors used for *Arabidopsis* experiments:

*Promoters:*

CaMV35S – constitutive

OsAnt1 – root-specific

*Target genes:*

HVAlaAT (Barley)

MmAlaAT1 and MmAlaAT2 (Mouse)

PfAlaAT (*Pyrococcus*)

Components of the expression vectors used for *Oryza* experiments:

*Promoters:*

Maize Ubiquitin-1 promoter – constitutive

PBpr1 – tissue-specific

*Target genes:*

MmAlaAT1 (Mouse)

PfAlaAT (*Pyrococcus*)

*Genetic constructs:* pGPMn: (tissue-specific expression of mouse AlaAT1)
        G=pGA backbone
        P=the PBpr1 promoter
        M=mouse 1 AlaAT
        n=nos terminator pGPPn: (tissue-specific expression of *Pyrococcus* AlaAT)
        G=pGA backbone
        P=the PBpr1 promoter
        P=Pyrococcus AlaAT
        n=nos terminator

Figure 1. (Continued)

pGUMn: (constitutive expression of mouse AlaAT1)
    G=pGA backbone
    U=UBI plus intron promoter
    M=mouse 1 AlaAT
    n=nos terminator pGUPn: (constitutive expression of *Pyrococcus* AlaAT)
    G=pGA backbone
    U=UBI plus intron promoter
    P=Pyrococcus AlaAT
    n=nos terminator

FIGURE 11. SEQ ID NO: 1 - Barley AlaAT cDNA atggctgccaccgtcgccgtggacaacctgaaccccaaggttttaaaatgtgagtatgctgtgcgtggagagattgtcatccatgctcagcgcttgcag
gaacagctaaagactcaaccagggtctctaccttttgatgagatcctctattgtaacattgggaacccacaatctcttggtcagcaaccagttacattct
tcagggaggttcttgccctttgtgatcatccagacctgttgcaaagagaggaaatcaaaacattgttcagtgctgattctatttctcgagcaaagcagat
tcttgccatgatacctggaagagcaacaggagcatacagccatagccagggtattaaaggacttcgtgatgcaattgcttctgggatcgcttcacgag
atggattccctgctaatgctgatgacattttctcacacagatggagcaagtcctggggtgcacctgatgatgcaattactgataaggaatgagaaagatg
gcattcttgtcccgattcctcagtaccccttgtactcggcttccatagctcttcatggcggagctcttgtcccatactatctcaatgaatcgacgggctggg
gtttggaaacctctgatgttaagaagcaacttgaagatgctcggtcaagaggcatcaacgttagggctttggtggttatcaatccaggaaatccaactg
gacaggtacttgctgaagaaaaccaatatgacatagtgaagttctgcaaaaatgagggtcttgttcttctagctgatgaggtataccaagagaacatc
tatgttgacaacaagaaattccactctttcaagaagatagtgagatccttgggatacggcgaggaggatctccctctagtatcatatcaatctgtttcta
agggatattatggtgagtgtggtaaaagaggtggttactttgagattactggcttcagtgctccagtaagagagcagatctacaaaatagcatcagtg
aacctatgctccaatatcactggccagatccttgctagtcttgtcatgaacccaccaaaggctagtgatgaatcatacgcttcatacaaggcagaaaaa
gatggaatcctcgcatctttagctcgtcgtgcgaaggcattggagcatgcattcaataaacttgagggaattacttgcaacgaggctgaaggagcaat
gtacgtgttccctcaaatctgtctgccacagaaggcaattgaggctgctaaagctgctaacaaagcacctgatgcattctatgctcttcgtctcctcgag
tcgactggaatcgtcgttgtccctggatcaggatttggccaggttcctggcacatggcacttcaggtgcacgatccttccgcaggaggataagatcccg
gcagtcatctcccgcttcacggtgttccatgaggcgttcatgtcagagtatcgtgactaaactggt

FIGURE 12. SEQ ID NO:2 - Barley AlaAT amino acid sequence

MAATVAVDNLNPKVLKCEYAVRGEIVIHAQRLQEQLKTQPGSLPFDEILYCNIGNPQSLGQQPVTFFREVLALCDHPDLL
QREEIKTLFSADSISRAKQILAMIPGRATGAYSHSQGIKGLRDAIASGIASRDGFPANADDIFLTDGASPGVHLMMQLLIR
NEKDGILVPIPQYPLYSASIALHGGALVPYYLNESTGWGLETSDVKKQLEDARSRGINVRALVVINPGNPTGQVLAEENQ
YDIVKFCKNEGLVLLADEVYQENIYVDNKKFHSFKKIVRSLGYGEEDLPLVSYQSVSKGYYGECGKRGGYFEITGFSAPVRE
QIYKIASVNLCSNITGQILASLVMNPPKASDESYASYKAEKDGILASLARRAKALEHAFNKLEGITCNEAEGAMYVFPQICL
PQKAIEAAKAANKAPDAFYALRLLESTGIVVVPGSGFGQVPGTWHFRCTILPQEDKIPAVISRFTVFHEAFMSEYRD

FIGURE 13. SEQ ID NO: 3 – *Mus musculus* AlaAT cDNA sequence (MmAlaAT)

Atggcctcacaaaggaatgaccggatccaggcttcaaggaatggactgaaggggaaggtgctaactctggataccatgaacccatgtgtgcggagg
gtggagtatgcagtccgaggcccatcgtgcaacgtgccttggagctggagcaggagctgcgccagggtgtgaagaagccttttactgaggttatccg
tgccaatattggggatgcacaagccatggggcagagacccatcaccttcttccgccaggtcctggccctctgtgtctacccaatcttctgagcagtccg
gacttcccagaggatgccaagagaagggcagaacgcatcttgcaggcatgcgggggccacagcctgggtgcctatagcattagtctggaatccagc
cgattcgggaggatgtggcgcaatatattgagaggagagacggaggcatccctgcagacccgaacaacatatttctgtccacaggggccagcgatgc
catcgtgaccatgctcaagctgctggtagccggcgagggccgtgcgcgaaccggtgtactcattcccattcctcagtacccactgtactcagctgcgct
ggctgagctggacgccgtcaagtggactactacctggacgaagagcgcgcctgggctcttgacatcgctgagctgcggcgcgctctgtgccaggcac
gtgaccgctgctgccctcgagtactatgcgtcatcaaccccgcaacccacggggcaggtgcagacccgtgaatgcatcgaggccgtaatccgctttg
ctttcgaagagggactcttcctgatggctgatgaggtataccaagacaatgtatatgctgagggctctcagttccattcattcaagaaggtgctcacg Figure 13. (Continued)

gagatggggccaccatatgccacgcagcaggagctcgcgtctttccactcagtctctaagggctacatgggcgagtgcgggtttcgtggtggctatgtg
gaagtggtaaacatggatgccgaggtgcagaaacagatggcgaaactgatgagcgtgcggttgtgtccaccagtgccgggccaggctttgatgggca
tggtggtcagtccgccaaccccctcggagccgtccttcaagcagtttcaagcagagaggcaggaggtgctggctgaactggcagccaaggctaaact
cacggagcaggtcttcaacgaggcccccgggatccgctgcaacccggtgcagggcgctatgtattccttccctcaaattcagctgcctttgaaagcagt
gcagcgtgcgcaggacctgggcctggcccctgacatgttcttctgtctgtgcctcctggaagagaccggcatctgcgttgtgcctgggagtggctttggg
cagcaggagggcacctatcatttccggatgaccattctgcccccccatggagaaactgcgggtgctgctggagaaactgaggcacttccatgctaaatt
cactcatgagtactcctt FIGURE 14. SEQ ID NO: 4 - *Pyrococcus* AlaAT cDNA sequence (PyAlaAT)

atgataagggcctcaaagagagctctctctgtggagtatgctattagagatgtcgttctacctgcaagggaacttgaaaaaaagggaatcaaggtaat
taggctaaacataggcgatcctgtaaagttcgactttcaaccacccgagcacatgaaggaagcatattgtaaagcaattaaagaggggcacaattac
tatggagatagtgagggattacccgagttaagaaaagctatagtagaaagggaaaagaggaagaatggagtggacataactcccgatgacgtgag
ggttacagctgcagtcactgaagctctccagctaattttttggagctctattagacccaggagatgaaattctagttcctgggcccagttatcctccctata
cagggcttgtaaagttctacggtggaaagcctgtggaatatagaactattgaagaggaagactggcaacctgatattgacgacattaggaagaagat
aacagacagaacaaaagctatagcagttataaaccccaacaacccgactggagcgctctacgacaaaaagacacttgaggaaatcttgaacatcgc
aggggaatatgaaattcctgttataagcgacgagatatacgatttgatgacatacgagggagaacacatttctcccggatcattaaccaaagatgttc
ctgtaatagttatgaacggattatccaaagtctactttgccacagggtggagacttggatacatgtactttgtcgatccagagaataaattgagtgaggt
cagagaggcaatagatagattggcaaggattagactgtgtccaaataccccgcacaattcgcagctatagcaggactaacgggcccaatggattat
ctcaaagaatacatgaaaaagctcaaggagagaagagattacatctacaagaggctaaatgagatcccaggaataagcacgacaaaaccacaag
gagcattttacatattccccaagatagaggtgggaccgtggaagaatgataaagaattcgttcttgacgttctccacaatgctcacgttctatttgttca
cggttcaggatttggagagtatggtgcaggccactttagagcagtgttcttgcctccaatagaaatcctggaagaggctatggatagattcgaaaagtt
catgaaagaaagactgaaagaatgatt FIGURE 15. SEQ ID NO:5 - PBpr1 promoter sequence 5'gaattctgaaagtttccgtccaaatcgcaccttttaaccgtttgaaaaacatacaaacgaaaaataatctatatcttaatcaggaagaaagagtacg
aaatggtgaaccgtcgaaactattcatatacgtcgtctgtctcatgaaaaaaaaaatcaatccagaaggatacgagacacttttacttcaacaaatat
agacatgagcttattctactaggtttggttgtttaataagacgaaagaaatacattggttagtttttcattaaaaaataatcgtttgactgacataaacct
aggaaatactggattaagatagatcagtaggattaagatccactgatgtaatttcccactgatttggtggctgacatgtggacctgagagttgtgtggg
ctcacatgtcaaatcacggtgaacagtacgtcacgatatgttagaggttcctcttccggagatacttatacgaattttgcggaaacctgcaaactttgat
ggacgattgaggcgagtttagttctaaattttttcttcaaacttctaacttttttcatcacatcgtttcaatttcaatcaaacttccaatgttgacgtgaacta
aacacacctatgagatatgagaagcgggttgacacttgacaagtcctgacatgctgtgttggcgtgggcccacctgccacgtcaggtccagctccgg
gtggttgggtttggtgctttccgataggcacgagctcggtaccatg3'

FIGURE 16. SEQ NO 6: Maize Ubiquitin 1 plus 1st Intron ctgcagtgcagcgtgacccggtcgtgcccctctctagagataatgagcattgcatgtctaagttataaaaaattaccacatatttttttgtcacacttgtt
tgaagtgcagtttatctatctttatacatatatttaaactttactctacgaataatataatctatagtactacaataatatcagtgttttagagaatcatat
aaatgaacagttagacatggtctaaaggacaattgagtattttgacaacaggactctacagttttatcttttagtgtgcatgtgttctcctttttttttgca
aatagcttcacctatataatacttcatccattttattagtacatccatttagggtttagggttaatggttttatagactaattttttagtacatctattttat
tctattttagcctctaaattaagaaaactaaaactctattttagtttttttatttaataatttagatataaaatagaataaaataaagtgactaaaaatta
aacaaatacccttttaagaaattaaaaaaactaaggaaacattttttcttgtttcgagtagataatgccagcctgttaaacgccgtcgatcgacgagtcta
acggacaccaaccagcgaaccagcagcgtcgcgtcgggccaagcgaagcagacggcacggcatctctgtcgctgcctctggaccccctctcgagagtt
ccgctccaccgttggacttgctccgctgtcggcatccagaaattgcgtggcggagcggcagacgtgagccggcacggcaggcggcctcctcctcctctc
acggcaccggcagctacgggggattcctttcccaccgctccttcgctttcccttcctcgcccgccgtaataaatagacacccctccacaccctctttccc
caacctcgtgttgttcggagcgcacacacacacaaccagatctcccccaaatccacccgtcggcacctccgcttcaaggtacgccgctcgtcctcccc
ccccccctctctaccttctctagatcggcgttccggtccatggttagggcccggtagttctacttctgttcatgtttgtgttagatccgtgtttgtgttagat
ccgtgctgctagcgttcgtacacggatgcgacctgtacgtcagacacgttctgattgctaacttgccagtgtttctctttggggaatcctgggatggctct
agccgttccgcagacgggatcgatctaggataggtatacatgttgatgtgggttttactgatgcatatacatgatggcatatgcagcatctattcatatg
ctctaaccttgagtacctatctattataataaacaagtatgttttataattattttgatcttgatatacttggatgatggcatatgcagcagctatatgtgg
atttttttagccctgccttcatacgctatttatttgcttggtactgtttcttttgtcgatgctcaccctgttgtttggtgttacttctgcag

Figure 17

```
SaccharomycescerevisiaeAlaAT1    ------------------------------------------------------------
SaccharomycescerevisiaeAlaAT2    MLSLSAKNHFYVSNSITHVIKSYIHIRTLTSSAEKMHITTPFSTSASSTKLKAFNVRPVLQRHSSSMVIAQNNRRSLSGQSSLNDLRHLNRFPHHTLKT
ArabidopsisthalianaAlaAT1        ------------------------------------------------------------
ArabidopsisthalianaAlaAT2        ----------------------------------MRRFVIGOAMNLIDQSRRQLHHHKNLSFVSLIPPSAPSDSSRHLSSSSSTM
MedicagotruncatulaAlaAT          ----------------------------------------MRRFLINQAKGLVDHSRRQHHHKSPSFLSPQRPLASSPPALSR---FFSSISEM
HordeumvulgareAlaAT              --------------------------------------------------MRKSAADRFRHLPNRSLVFVRNQNQQYHRPSP---------LRSL
ArabidopsisthalianaGGT1          ------------------------------------------------------------
ArabidopsisthalianaGGT2          ------------------------------------------------------------
MusmusculusAlaAT1                ------------------------------------------------------------
HomosapienAlaAT1                 ------------------------------------------------------------
MusmusculusAlaAT2                --------------------------------------------------------MSQRNDRIQ
HomosapienAlaAT2                 --------------------------------------------------------MASTGDRSQ
PyrococcusfuriosusAlaAT          ------------------------------------------------------------

SaccharomycescerevisiaeAlaAT1    ---------------------------------------------MQRAALVLVRRGSCPRASPWGRSHSSAAEPASAALKY
SaccharomycescerevisiaeAlaAT2    ---------------------------------------------MQRAALVRRGCGPRTBSWGRSQSSAAEPASAVLKV
ArabidopsisthalianaAlaAT1        KQLDFKPAGKIKKDLNTGVTGAEYAVRGAIPTRADELKEHLAKNPEVLPFDDINANIGNPQQLDDRPLIFTRQVLALEYPELLRVGHNELASLNLFS
SaccharomycescerevisiaeAlaAT2    SNNFFYPAEQLITEDVNENVLKAKTAVRGAFPMRAEHLKAQLEKDFVQSLPFDRITNANIGNPQQLQAOKFLTYYROVLSLLQYPELLNQNEQQLVDSKLFK
ArabidopsisthalianaAlaAT2        SASDSSSLPVTLDITINPKVIKCEYAVRGEIVNIAQKLQEDLATNKDAYPFDELIYCNIGNPQSLGQOPITFFREVLALCSYTALIDESA----THGLFS
MedicagotruncatulaAlaAT          SASDSTSSLPVTLDSINPKVLKCEYAVRGEIVTLAQNLQKALQANPDAHSFDEIIYCNIGNPQSLGQPITFFREVLALCDVPALIDKSE----TQGLFS
HordeumvulgareAlaAT              SSMASDSPFFVTAQNINPQVLKCQYAVRGEIVTLAQNLQEOLKTOPGSLPFDEIYCNIGNPQSLGOQPITFFREVLALCHPDLIQKSE----IKTLFS
ArabidopsisthalianaGGT1          ----MAATAVDNLNPKVLKCEYAVRGEITLAQRLQEOLATOPGSLPFDEILYCNIGNPQSLGOQPITFFREVLALCHPDLIQKEE----IKTLFS
ArabidopsisthalianaGGT2          ----MAIKALDVDTILNENVRKCQYAVRGELVLRASELQKEGKK-------IIFTNVGNPHALGGKPLIFPRQVSLCQAPRLLDDPN----VGMLFP
MusmusculusAlaAT1                ----MSIKALDVESLNENVRNCQYAVRGELYIRASELQKEGK--------IIFTNVGNPHALGGKPLITPROVVSLCQAPRLLDDPN----VGMLFP
HomosapienAlaAT1                 ASRNGLRGKVIVTLDGMNPCVRENVPRRVEYAVRGPIVQRALEIEQEIRQG--VKKPFTEVLRANIGDAQAMGQBPITFLRQVLALCVWPDLL33P----DFP
MusmusculusAlaAT2                AVRNGLRAVVITLDGMNPKVRERVFYAVRGPIVLRAGEIEMELRQG--VKKPFTEVLRANIGDAHAMGQOPITFLRQVLALCYPNLINSP----SFP
HomosapienAlaAT2                 RPERSPRDRIITLESMNPQVKAVEYAVRGPIVLRAGEIELELQRG--IKKKPFTEVIRANIGDAQAMGQOPITFLRQVMALCYPNLLNSP----SFP
PyrococcusfuriosusAlaAT          ----------MIRASKRALSVEYAIR--DVLPARELEK---------KGIKVIRLNIGDPVKFDFQPP SaccharomycescerevisiaeAlaAT1    RDALERAERLNDIGG-SIGAESHSQGVPGIRQTVADFITRDQGEPATPEDIVLITGASSAATSLLSLLCKDS----QTGLLIPEPQYPLYTASASLFNA
SaccharomycescerevisiaeAlaAT2    RDAIKRAKSLMEDIGG-SVGAENSSQGVEGIRKSVAEFITKRDEGEISYPEDIFLHIAGASAAVNYLLSIPCRGP----ETGVLIPEPQYPLYIATALNNS
ArabidopsisthalianaAlaAT1        SDSIERAWKIIDHIPGRATGAENSHSQGIKGLRDAIADGIEARDG--FPADPNDIFMTDGASPGVHMMMQLLISE----KDGILSPIPQYPLYSASIALHGG
ArabidopsisthalianaAlaAT2        TDSIDRAWKIIDHIPGRATGAENSHSQGIKGLRDVIAAGIEARDG--FPADPNDIFLIDGASPAVTHMMWQLLISE----KDGILSPIPQYPLYSASIAHGG
MedicagotruncatulaAlaAT          ADSIERAWQIVDQIPGRATGAENSHSQGIQGLRDTIAAGIEERDG--FPCNANDIFLIDGASPAVHMMMAMQLLIRNE----KDGILCPIPQYPLYSASIALHGG
HordeumvulgareAlaAT              ADSIDRAKQILAMIPGRATGAENSHSQGIKGLRDAIALSGIASRDG--FPANADDIFLIDGASPGVHLMMQLLIRNE----KDGILVPEPQYPLYSAIALHGG
ArabidopsisthalianaGGT1          ADAIARAKHVLSLISG-GLGAENSRGLPGVRKEVAEFIERRDG--YPSDPELIFIDGASKGVMQILNCVIRGN----KDGILVPKPQYPLVSATTISLLGG
ArabidopsisthalianaGGT2          ADAIARAKHVLSLISG-GLGAENSRGLPGVRKEVAEFIERRDG--YPSDPELIPIDGASVGVMQILNCVIRGQ----KDGLIVPEPQYPLVSATISLLGG
MusmusculusAlaAT1                EDAKRRAERIIQACGGHSLGAYSTSSGIQPIREDVAQYIERRDGGIPADPNNIFLSTGASDAIVTMKLLVAGEGRARTGVLIPIPEVQYPLYSAIAFLDA
HomosapienAlaAT1                 DNAKKRAERIIQACGGHSLGAYSTSSGIQLIREDVARVIERRDGGIPADPNNVFLSTGASDAIVTVKLLVAGEGHTRGVLIPIPEVQYPLYSATIALGA
MusmusculusAlaAT2                EDNAKKRAERIIQACGGNSLGSYSASQGVNCIREDVAALFITRDG--VPALDPNIVYLLTGASDGISTILALLVSGGEKSRTGVMIPIPEYPLYEAVISELDA
HomosapienAlaAT2                 EDAKKRAERIIQACGGNSLGSYSASQGVNCIREDVAANVITRRDGGVPALDPNIVINITGASDGISTILIKLLVSGGEKSRIGVMIPIPEYPLYEAVISELDA
PyrococcusfuriosusAlaAT          ------EHMKEAYCKAIKEGHNTLPDSEGLPELRKAIVEREKRNG--VDIIPDDVKTPAVTEALQLIPGALLDG----DEIIVPGPYPPPYTGLVKFVGS
```

Figure 17 continued

PLANTS HAVING ENHANCED NITROGEN USE EFFICIENCY AND METHODS OF PRODUCING SAME

CROSS-REFERENCE TO RELATED APPLICATIONS

This application is a 35 U.S.C. 371 National Phase of PCT Application Number PCT/EP2014/054171 filed Mar. 4, 2014, which claims priority to U.S. provisional application No. 61/773,770 filed Mar. 6, 2013, the disclosure of which is hereby incorporated by reference in its entirety.

JOINT RESEARCH AGREEMENT

Work disclosed herein was performed in accordance with the terms of a joint research agreement between Bayer CropScience AG, Monheim am Rhein, Germany (subsequently assigned to Bayer CropScience LP, Research Triangle Park, USA), The Governors of the University of Alberta, Alberta, Canada and Dr. Allen Good, Alberta, Canada.

FIELD OF INVENTION

The present invention relates to plants having enhanced yield and/or nitrogen utilization efficiency (NUE), to methods for enhancing yield and NUE in plants, and to methods of increasing biomass and seed yield in plants grown under nitrogen limiting conditions.

BACKGROUND OF THE INVENTION

The productivity of plants is limited by the three primary nutrients: nitrogen, phosphorous and potassium, in most natural and agricultural ecosystems. Generally nitrogen is the most important of the three limiting nutrients and the major components in fertilizers. Since nitrogen is usually the rate-limiting element in plant growth, most field crops have a fundamental dependence on inorganic nitrogenous fertilizer. The nitrogen source in fertilizer is usually ammonium nitrate, potassium nitrate, or urea (McAllister et al., 2012).

Increased nitrogen use efficiency by plants has a number of beneficial effects, for example, increased growth and yield when compared to conventional plants grown in nitrogen poor soils, and reduced requirement for the addition of nitrogenous fertilizers to crops (Good and Beatty, 2011a). Fertilizers account for a significant percentage of the costs associated with crop production, therefore using less fertilizer would reduce the producers' costs. A reduction in fertilizer application would also lessen the environmental damage resulting from extensive nitrogenous fertilizer use. Excess fertilizer application causes increased eutrophication, acid rain, soil acidification and the greenhouse effect. These environmental disasters cause further problems such as fish kills, loss of biodiversity, increased algal blooms, loss of arable land and accelerated global climate change, affecting the world population on both social and economic scales (Good and Beatty, 2011b).

Of the commercially grown plants, monocots (which include the main cereal crops) represent a large percentage of the crops grown in the world with approximately 217 million hectares of wheat and 158 million hectares of both maize and rice planted in 2007. Approximately half of the global calorie and protein requirement is derived from wheat, rice and maize. Rice is routinely used as a model crop for genetic and physiological studies in other monocot crops including maize, wheat, sugarcane, barley, sorghum, rye and grass. Rice has a small, diploid genome that is well conserved and syntenic across monocots (McAllister et al., 2013).

In the case of NUE plant engineering, a number of different genes have been evaluated for their role in increasing the efficacy of N uptake, utilization or remobilization in the plant. One way to improve the nitrogen use efficiency (NUE) of the cereal crops would be to improve the different components of NUE. NUE can be partitioned into N uptake efficiency (NUpE) and N utilization efficiency (NUtE; Good et al., 2004). NUtE can be further reduced to N assimilation and N remobilization. Therefore, increasing the efficiency of either N uptake or N utilization, could lead to an increase in NUE of the crop. There have been a number of single genes targeted as candidates for genetic engineering to try and increase the NUE of crop plants (reviewed in Good and Beatty, 2011a and McAllister et al., 2012). Many of these candidate genes are primary N uptake and assimilation genes such as nitrate and ammonia transporters, nitrate reductase, GS and GOGAT. Gene targets that have shown an NUE phenotype in a crop plant after bioengineering over-expression include genes that are not primary N assimilation genes, but instead are involved in N metabolism further downstream than GS (glutamine synthase) and GOGAT (Glutamine oxoglutarate aminotransferase) such as alanine aminotransferase (AlaAT), or are transcriptional regulators, such as Dof1 (Good et al., 2007; Shrawat et al., 2008; Yanagisawa et al., 2000; Yanigisawa et al., 2004). While some of these genes have shown some efficacy, in most cases the over-expression of these genes, under the specific promoter used, did not result in any significant increase in NUE or components of NUE (reviewed in Good and Beatty, 2011a and McAllister et al., 2012).

SUMMARY OF THE INVENTION

The present invention relates to plants having enhanced yield and/or nitrogen utilization efficiency (NUE) and methods of producing such plants. The present invention also relates to methods for enhancing yield and NUE in plants, and to methods of increasing biomass and seed yield in plants grown under nitrogen limiting conditions. This invention also relates to the use of AlaAT encoding polynucleotides from non-plant organisms in plants, and the use of different variants of AlaAT encoding polynucleotides from organisms such as Archaea and mammals in plants under control of a plant-expressible promoter.

It is an object of the invention to provide an improved plant having enhanced nitrogen efficiency.

According to the present invention there is provided a non-naturally occurring plant or plant part from a non-naturally occurring plant comprising, elevated levels of one or more different nitrogen utilization proteins, as described above from a plant or non-plant under control of a plant-expressible promoter.

The one or more nitrogen utilization proteins may be selected from aminotransferases, alanine aminotransferase (AlaAT) and aspartate aminotransferase. The one or more nitrogen utilization proteins may be variants of AlaAt encoding polynucleotides from non-plants, such as from Archaea and mammals.

The non-naturally occurring plant or plant part may be selected from corn, wheat, maize, rice, barley, canola, soybean, cotton, alfalfa, safflower, sugarcane, tomato and potato.

The present invention also provides a non-naturally occurring plant or plant part wherein the plant or plant part comprises a first nucleic acid encoding one or more non-naturally occurring AlaAT gene operably linked to a second nucleic acid comprising a promoter, such as, but not limited to, a tissue-specific promoter.

The present invention also pertains to a seed obtained from the non-naturally occurring plant as described above.

The present invention provides a method of generating a plant with increased nitrogen use efficiency comprising, introducing a nucleic acid encoding one or more nitrogen utilization protein, operably linked to a promoter, such as, but not limited to, a tissue-specific promoter, and producing the plant, the plant comprising elevated levels of one or more nitrogen utilization protein. The one or more nitrogen utilization protein may be selected from the group consisting of the aminotransferases. Preferably, the one or more nitrogen utilization proteins is alanine aminotransferase.

To generate monocot plants that are able to grow under suboptimal nutrient conditions, a monocot plant may be generated that uses nitrogen more efficiently. Such monocot plants are able to grow in soils that are poorer in nitrogen, as a result of being able to more efficiently use the nitrogen that is available, with no loss in yield. Additionally, such monocot plants may also demonstrate enhanced yield in soils that have normal nitrogen levels as well. Nitrogen use efficiency in plants is a result of two main subcomponents; N uptake efficiency and N utilization efficiency. A plant exhibiting a nitrogen use efficiency phenotype may have improvements in its ability to take up nitrogen from the soil, which is a desired trait in plants growing in lower nutrient-available soils. Or the NUE plant may have improvements in its ability to utilize the N that it has taken up so that the available N (whether it be low or high) is efficiently incorporated into the subcellular components (such as nucleic acids, proteins, storage etc.), translocated to the necessary tissues and remobilized at the correct developmental stage into seed. Or, another possibility is that the NUE plant has improvements in both N uptake and utilization. Any one of these possibilities would allow for an increased yield from a NUE crop grown in normal nitrogen conditions because those plants would be able to take up a non-limiting amount of nitrogen and be able to use the nitrogen to increase biomass and seed yield, either by increased number of seeds or an increase in seed weight, or both.

This present invention will allow the user to develop plants that have an environmental benefit in that they can maintain yield, while reducing the need for high levels of nutrient application. Alternatively, under high nutrient levels this invention would improve plant nutrient up-take allowing plants to extract more nutrients from their environment during times of nutrient abundance. Using the methods and compositions of the invention, plants may be improved for growth and development under environmental conditions usually unsuitable for growth of the plant. Furthermore, the methods and compositions of the invention permit the genetic engineering of a plant to alter one or more plant characteristics in only selected tissues of the plant.

The present invention provides a method for directing expression of a specific target gene or nucleotide sequence in a plant, including producing a plant from a transformed plant cell such that tissue-specific expression of a target gene or nucleotide sequence occurs within a selected tissue of the plant, wherein the transformed plant cell contains a target gene or nucleotide sequence for a novel variant to AlaAT.

The present invention further provides a method for increasing biomass of a plant growing under one or more environmentally adverse conditions comprising: transforming a plant with a novel target gene or nucleotide sequence in operative linkage with an OsANT1 or PBpr1 promoter element to produce a transformed plant, the target gene or nucleotide sequence encoding an enzyme involved in nitrogen assimilation or metabolism; and growing the transformed plant.

This invention also relates to the use of AlaAT encoding polynucleotides from non-plant organisms in plants, and the use of different variants of AlaAT encoding polynucleotides from other organisms, such as Archaea and mammals, in plants under control of a plant-expressible promoter.

Also embraced within the present invention is a method for increasing biomass of a plant growing under conditions of low nitrogen comprising: transforming a plant with a target gene or nucleotide sequence in operative linkage with an OsANT1 or PBpr1 promoter element to produce a transformed plant, the target gene or nucleotide sequence encoding an enzyme involved in nitrogen assimilation; and growing the transformed plant. Preferably, the target gene or nucleotide sequence encodes an enzyme that is a variant of AlaAT.

The present invention also pertains to a method for increasing the biomass of a plant growing under one or more environmentally adverse conditions comprising: transforming a plant with a gene or nucleotide sequence encoding AlaAT in operative linkage with a promoter element to produce a transformed plant; and growing the transformed plant.

The present invention is also directed to a method for increasing seed yield of a plant comprising: transforming the plant with a target gene or nucleotide sequence or nucleotide sequence in operative linkage with a specific promoter element, to produce a transformed plant, the target gene or nucleotide sequence or nucleotide sequence encoding an enzyme involved in nitrogen assimilation or metabolism; and growing the transformed plant. Preferably, the target gene or nucleotide sequence encodes an enzyme that is a variant of AlaAT.

Also embraced within the present invention is a method for increasing seed yield of a plant growing under conditions of high nitrogen comprising; transforming a plant with a target gene or nucleotide sequence or nucleotide sequence in operative linkage with an promoter element to produce a transformed plant, the target gene or nucleotide sequence or nucleotide sequence encoding an enzyme involved in nitrogen assimilation; and growing the transformed plant. Preferably, the target gene or nucleotide sequence encodes an enzyme that is a variant of AlaAT.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 1 outlines the components of the various constructs contemplated by the present invention. Each of these genetic constructs has a promoter operatively linked to a variant of AlaAT (including HvAlaAt, MmAlaAT1, MmAlaAT2 and PfAlaAt. These constructs are given the designation of Promoter::AlaATgene and terminated by a nos terminator. The selection marker is kanamycin (Kan) for plasmid selection and hygromycin (Hyg) for plant selection.

FIG. 2A represents the constructs introduced into the ecotype Columbia (COL background); and FIG. 2B represents the constructs introduced into the alaat1;2 double knockout line of *Arabidopsis thaliana* (alaat1;alaat2 Background).

FIG. 3A shows tap root growth under the condition of low light, 0% sucrose and 1 mM nitrate ($NO_3^-$); and FIG. 3B shows tap root growth under the condition of low light, 0.2% sucrose and 0.25 $NO_3^-$.

FIG. 11 shows SEQ ID NO:1, which is the nucleotide sequence of barley (*Hordeum vulgare*) AlaAT used herein.

FIG. 12 shows SEQ ID NO:2, which is the amino acid sequence of barley (*Hordeum vulgare*) AlaAT used herein.

FIG. 13 shows SEQ ID NO:3, which is the nucleotide sequence of mouse (*Mus musculus*) AlaAT1 used herein.

FIG. 14 shows SEQ ID NO:4, which is the nucleotide sequence of *Pyrococcus furiosus* AlaAT used herein.

FIG. 15 SEQ ID NO:5, which is the nucleotide sequence of the pPBpr1 promoter element used herein.

FIG. 16 shows SEQ ID NO:6, which is the nucleotide sequence of the maize Ubiquitin 1 promoter elements, plus its first intron used herein.

FIG. 17 shows amino acid sequence comparisons of various alanine aminotransfereases (AlaAT's). *Saccharomyces cerevisea* AlaAT1 (SEQ ID NO:7); *Saccharomyces cerevisea* AlaAT2 (SEQ ID NO:8); *Arabidopsis thaliana* AlaAT1 (SEQ ID NO: 9); *Arabidopsis thaliana* AlaAT2 (SEQ ID NO: 10); *Medicago truncatula* AlaAT (SEQ ID NO: 11); *Arabidospsis thaliana* GGT1 (SEQ ID NO: 12); *Arabidospsis thaliana* GGT2 (SEQ ID NO: 13); *Pyrococcus furiosus* AlaAT (SEQ ID NO: 14); *Mus musculus* AlaAT1 (SEQ ID NO: 15); *Mus musculus* AlaAT2 (SEQ ID NO: 16); *Homo sapiens* AlaAT1 (SEQ ID NO: 17); *Homo sapiens* AlaAT2 (SEQ ID NO: 18).

DETAILED DESCRIPTION

Figure 2A:
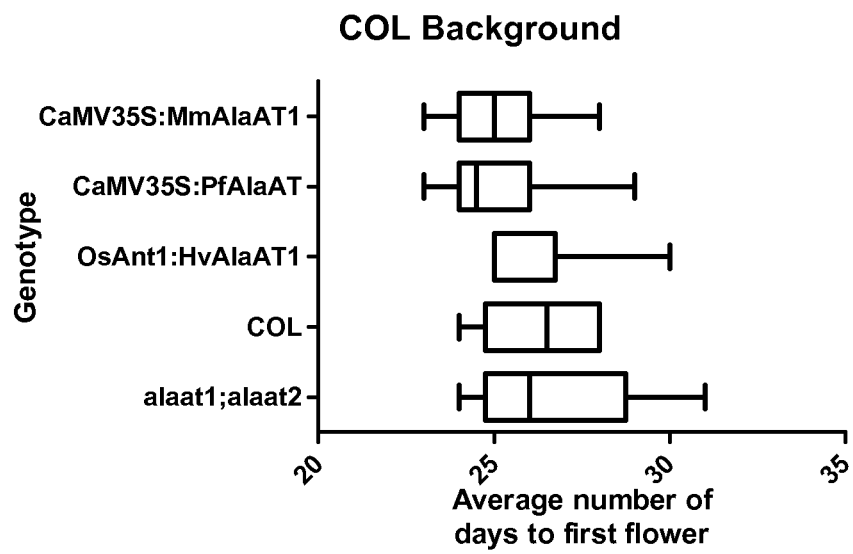
FIGS. 2A and 2B show the effects of specific constructs on flowering time in *Arabidopsis thaliana*.

The present invention relates to monocot plants having enhanced yield and/or nitrogen utilization efficiency (NUE), to methods of producing such plants, to methods for enhancing yield and NUE in monocot plants, and to methods of increasing biomass and seed yield in monocot plants grown under nitrogen limiting conditions. This invention also relates to variants of AlaAT and their operative linkage with different promoters, for example, without limitation, the cauliflower mosaic virus promoter CaMV 35S and tissue specific promoters (such as OsANT1 and PBpr1; Shrawat et al., 2008; Lock, 2011). The present invention also relates to the use of AlaAT encoding polynucleotides from non-plant organisms in plants, and the use of different variants of AlaAT encoding polynucleotides from organisms such as Archaea and mammals in plants under control of a plant-expressible promoter.

The following description is of a preferred embodiment.

The headings provided are not meant to be limiting of the various embodiments of the invention. Terms such as "comprises", "comprising", "comprise", "includes", "including" and "include" are not meant to be limiting. In addition, the use of the singular includes the plural, and "or" means "and/or" unless otherwise stated. Unless otherwise defined herein, all technical and scientific terms used herein have the same meaning as commonly understood by one of ordinary skill in the art.

The language "tissue-specific expression of a target nucleotide sequence" is known in the art and includes the expression of a target nucleotide sequences in only selected tissues; although the target nucleotide sequence may be present in multiple tissues, it is expressed in only a subset of those tissues. Such selective expression may be due to the influence of one or more regulatory genetic elements, for example but not limited to promoter elements, repressor elements, enhancer elements, or other regulatory factors that may interact with DNA, RNA.

The language "target gene" or "target nucleotide sequence" is art-recognized, and includes any nucleotide sequence which is desirably expressed in one or more selected plant tissues. Examples of target genes or nucleotide sequences which may advantageously be utilized in conjunction with the methods of the invention include genes or nucleotide sequences involved in nitrogen assimilation and/or utilization, genes or nucleotide sequences involved in stress resistance or disease and pest resistance, and genes or nucleotide sequences involved in nutrient uptake and utilization. Such genes or nucleotide sequences are well known to one of skill in the art.

The language "plant" is art-recognized, and includes any monocotyledenous or dicotyledenous plant. Examples of plants for use in the invention include but are not limited to canola, barley, maize, rice, tobacco, soybean, cotton, alfalfa, tomato, wheat, potato, *Arabidopsis thaliana* and certain tree genera, including conifers and *Populus* species.

The language "non-plant" includes any other organisms that are not plants, such as, but not limited to, microorganisms (for example, without limitation, bacteria, yeast, fungi, algae, Archaea, virus), mammals and non-mammals (for example, without limitation, arthropods, birds, reptiles, amphibians and fish).

The language "operative linkage" is art-recognized, and includes the placement of a target nucleotide sequence relative to a nucleic acid regulatory sequence such that the expression of the target nucleotide sequence is controlled by the regulatory sequence. This regulatory sequence can have a positive effect (increase) on the expression of the target gene or nucleotide sequence (e.g., the regulatory sequence is a promoter or an enhancer element), or the regulatory sequence can reduce the expression of the target gene or nucleotide sequence (e.g., the regulatory sequence is a repressor element). The regulatory sequence may be physically located 5' or 3' of the target gene or nucleotide sequence, may be within the coding sequence of the target gene or nucleotide sequence, or may be contained on an intron within the target gene or nucleotide sequence.

The language "nulls" is art-recognized and includes a plant that has undergone tissue culturing but does not carry a transgene or selectable marker.

Production of plants which express one or more target genes or nucleotide sequences under a plant-expressible promoter are described herein. The invention further provides seeds containing one or more target genes or nucleotide sequences under the control of a plant-expressible promoter, such as a tissue-specific promoter element that specifically directs the tissue-specific expression of the gene or nucleotide sequence. By the methods of the invention, it is possible to produce plants having one or more desired traits or properties in selected tissues; e.g., to alter specifically the genetic and/or physiological properties of the fruit or the roots of the plant. The invention further provides methods of producing plants having root and leaf-specific expression of one or more desired nucleotide sequences, using the OsANT1 and PBpr1 promoter elements (Shrawat et al., 2008; Lock, 2011).

The methods of the invention for the production of plants involve the operative linkage of one or target genes or nucleotide sequences to a genetic regulatory element, such as, but not limited to, a promoter. As is known in the art, promoters are nucleic acid sequences that allow for regulation of transcription of a gene or nucleotide sequence. Promoters can allow for constitutive expression, such as the well known cauliflower mosaic virus promoter CaMV 35S, inducible expression, such as the stress inducible promoter rd29A (Pino et al., 2007), tissue-specific expression, such as the root-specific OsANT1 promoter (Good et al., US 2009/0288224), and developmentally specific expression, such as the senescence induced IPT promoters (Ma 2008). Promoters can also be weak or strong, suggesting that whenever or wherever they are induced, they will allow for expression of the attached gene or nucleotide sequence at varying levels.

The methods of the invention for the production of plants having tissue-specific expression of one or more target genes or nucleotide sequences are accomplished through the use of a genetic regulatory element which directs the tissue-specific expression of the target gene(s). This regulatory element may be either negative or positive in activity: a plant tissue-specific promoter or enhancer element permits the expression of the target gene or nucleotide sequence(s) in one or more specific tissues, whereas a plant tissue-specific repressor suppresses the expression of the target genes or nucleotide sequences in one or more specific tissues, while expression in the other tissue(s) continues unabated. For the purposes of the present invention, it will be understood that promoter sequences constitute the preferred genetic regulatory elements of the invention.

It will be understood by one skilled in the art that modifications may be made to the promoters used in the methods and constructs of the invention to improve or modulate the activity of the promoter. Multiple copies of a selected promoter may be operatively linked to a single target gene or nucleotide sequence to thereby alter the expression level of the linked gene or nucleotide sequence, or a selected promoter may be operatively linked to one or more target genes or nucleotide sequences such that the expression of each target gene or nucleotide sequence is coordinately regulated. A promoter may be of any size appropriate to permit the tissue-specific functioning of the promoter. A promoter may be modified (e.g., by mutagenesis, deletion, insertion, or truncation) to alter the degree to which the operatively linked gene or nucleotide sequence is expressed in the selected tissue, or to alter the specificity of tissue expression directed by the promoter. Further, the placement of the promoter relative to the operatively linked target gene or nucleotide sequence may be modulated (e.g., moved further away or closer together) to attain a desired level of promoter-directed expression.

A target gene or nucleotide sequence of the invention may be any gene or nucleotide sequence which is desirably expressed in a plant, including the expression in a tissue-specific manner in a plant. General classes of target genes or nucleotide sequences that may be employed in the methods and constructs of the invention include one or more genes or nucleotide sequences encoding plant structural proteins, genes or nucleotide sequences encoding proteins involved in the transport and/or uptake of nutrients, genes or nucleotide sequences encoding enzymes and proteins involved in nutrient utilization, genes or nucleotide sequences encoding proteins involved in stimulation or continuation of plant growth. Further, the target gene or nucleotide sequence may be a nucleotide sequence which, when transcribed, is antisense to a native sequence, the transcription and translation of which is desired to be suppressed.

For example, which is not to be considered limiting in any manner, the genes or nucleotide sequences of interest are those encoding enzymes in the assimilation and/or metabolism of nitrogen. The genes or nucleotide sequences of interest may include genes or nucleotide sequences which encode proteins involved in assimilating ammonia into amino acids or use the formed amino acids in biosynthetic reactions, that is, "nitrogen utilization proteins". Example of nitrogen utilization proteins include, but are not limited to, nitrate ammonium and amino acid transporters, glutamine synthetase (GS), asparagine synthetase (AS), glutamate synthase (also known as glutamate 2:oxogluturate amino transferase and GOGAT), asparaginase (ANS), glutamate dehydrogenase (GDH), aspartate aminotransferase (AspAT) and alanine aminotransferase (AlaAT) and those genes or nucleotide sequences which may be involved in Nutrient Use Efficiency (NUE) as described by Beatty et al. (2009), and in U.S. Pat. No. 7,589,257 (which is incorporated herein by reference).

The target gene or nucleotide sequence may be a gene or nucleotide sequence naturally expressed in a selected plant (endogenous), or it may be not naturally expressed in the selected plant (non-endogenous). The gene or nucleotide sequence may originate from a plant or from a non-plant, including, without limitation, viral, bacterial, Archaea or animal sources. Preferably, the gene or nucleotide sequence is heterologous to the promoter to which it is linked, in that it is not linked to an unmodified, inducible promoter to which the gene or nucleotide sequence is naturally linked. Thus, as used herein, the term "heterologous" with respect to a nucleic acid or DNA refers to a nucleic acid or DNA which is operably linked to a nucleic acid to which it is not naturally linked in nature. For example, a promoter is said to be heterologous with respect to a coding region, when that promoter is not naturally linked to that coding region.

As used herein, the term "endogenous" with respect to a nucleic acid molecule or a polypeptide in an organism refers to a nucleic acid molecule or a polypeptide having a nucleotide sequence or respectively an amino acid sequence, which is naturally occurring within cells of that organism. Nucleic acid molecules or polypeptides do not become endogenous to a particular organism because that organism or cells of that organism have been modified using, for example, recombinant DNA techniques to artificially contain such nucleic acid molecule or polypeptide. Therefore, as used herein, a "non-endogenous" nucleic acid molecule or polypeptide is a nucleic acid molecule or polypeptide that is not naturally occurring with cells of an organism, and may have been artificially introduced.

It is therefore contemplated herein that the target gene or nucleotide sequence be a non-plant, non-endogenous AlaAT for expression in a plant, such as SEQ ID NOs: 1, 3 or 4 and *Mus musculus* AlaAT2, which is known in the art (see for example McAllister et.al, 2013; which is incorporated herein by reference). The target gene or nucleotide sequence can be any non-plant nucleotide sequence having an nucleic acid sequence similarity of approximately 70% to the nucleic acid sequence of barley (*Hordeum vulgare*) AlaAT (SEQ ID NO:1), mouse (*Mus musculus*) AlaAT (SEQ IDNO:3), *Mus musculus* AlaAT2, (McAllister et.al, 2013), or *Pyrococcus furiosus* AlaAT (SEQ ID NO:4), or any amount between 70% and 100% amino acid sequence, for example, but not limited, to 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% nucleic acid sequence similarity to the nucleic acid sequence of barley (*Hordeum vulgare*) AlaAT, mouse (*Mus musculus*) AlaAT, *Mus musculus* AlaAT2, (McAllister et.al, 2013), or *Pyrococcus furiosus* AlaAT, or any amount therebetween.

Sequence identity or sequence similarity may be determined using a nucleotide sequence comparison program, such as that provided within DNASIS (for example, using, but not limited to, the following parameters: GAP penalty 5, # of top diagonals 5, fixed GAP penalty 10, k-tuple 2, floating gap 10, and window size 5). However, other methods of alignment of sequences for comparison are well-known in the art for example the algorithms of Smith & Waterman (1981, Adv. Appl. Math. 2:482), Needleman & Wunsch (J. Mol. Biol. 48:443, 1970), Pearson & Lipman (1988, Proc. Nat'l. Acad. Sci. USA 85:2444), and by computerized implementations of these algorithms (e.g. GAP, BESTFIT, FASTA, and BLAST), or by manual alignment and visual inspection.

Also included are nucleotide sequences that hybridize under stringent hybridization conditions to SEQ ID NO:1; SEQ ID NO:3; SEQ ID NO:4, or *Mus musculus* AlaAT2, (McAllister et.al, 2013). The present invention also includes a nucleotide sequence that hybridizes under stringent hybridization conditions to a compliment of SEQ ID NO:1; SEQ ID NO:3; SEQ ID NO:4, or *Mus musculus* AlaAT2, (McAllister et.al, 2013). These nucleotide sequences that hybridize to SEQ ID 1, 3, 4, or *Mus musculus* AlaAT2, (McAllister et.al, 2013), a complement of SEQ ID 1, 3, 4, or *Mus musculus* AlaAT2, (McAllister et.al, 2013), encode a protein that exhibits AlaAT activity.

Hybridization under stringent hybridization conditions is known in the art (see for example Current Protocols in Molecular Biology, Ausubel et al., eds. 1995 and supplements; Maniatis et al., in Molecular Cloning (A Laboratory Manual), Cold Spring Harbor Laboratory, 1982; Sambrook and Russell, in Molecular Cloning: A Laboratory Manual, $3^{rd}$ edition 2001; each of which is incorporated herein by reference). An example of one such stringent hybridization conditions may be about 16-20 hours hybridization in 4×SSC at 65° C., followed by washing in 0.1×SSC at 65° C. for an hour, or 2 washes in 0.1×SSC at 65° C. each for 20 or 30 minutes. Alternatively, an exemplary stringent hybridization condition could be overnight (16-20 hours) in 50% formamide, 4×SSC at 42° C., followed by washing in 0.1×SSC at 65° C. for an hour, or 2 washes in 0.1×SSC at 65° C. each for 20 or 30 minutes, or overnight (16-20 hours), or hybridization in Church aqueous phosphate buffer (7% SDS; 0.5M $NaPO_4$ buffer pH 7.2; 10 mM EDTA) at 65° C., with 2 washes either at 50° C. in 0.1×SSC, 0.1% SDS for 20 or 30 minutes each, or 2 washes at 65° C. in 2×SSC, 0.1% SDS for 20 or 30 minutes each.

Figure 17:
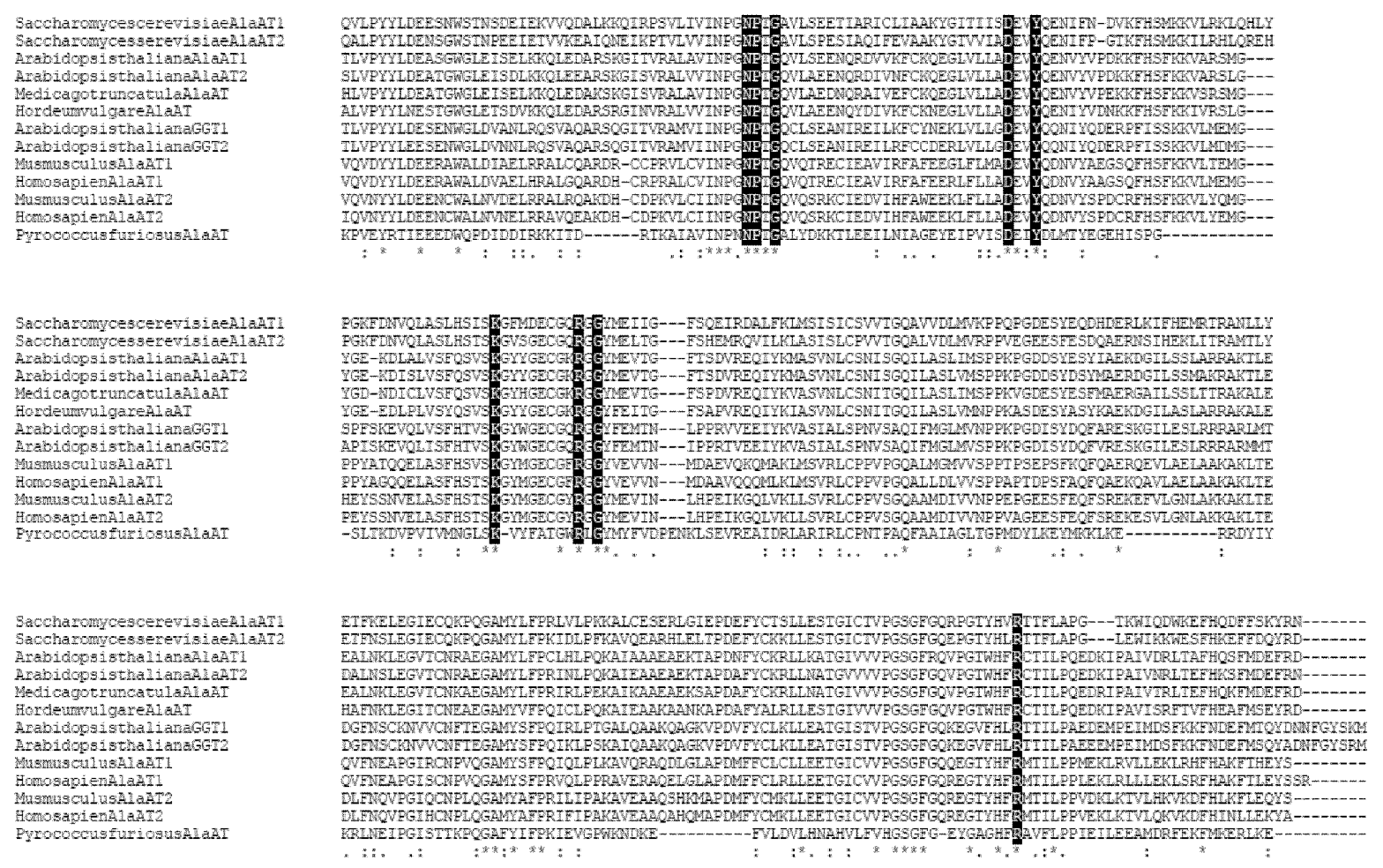

In addition, the target gene or nucleotide sequence can be any non-plant nucleotide sequence having an amino acid sequence similarity of approximately 80% to the amino acid sequence of barley (*Hordeum vulgare*) AlaAT, mouse (*Mus musculus*) AlaAT or *Pyrococcus furiosus* AlaAT, or any amount between 80% and 100% amino acid sequence, for example, but not limited, to 81, 82, 83, 84, 85, 86, 87, 88, 89, 90, 91, 92, 93, 94, 95, 96, 97, 98 or 99% amino acid sequence similarity to the amino acid sequence of barley (*Hordeum vulgare*) AlaAT, mouse (*Mus musculus*) AlaAT or *Pyrococcus furiosus* AlaAT, or any amount therebetween (see FIG. 17). For example, the following sequences may be used:

| Species | Gene | mRNA NCBI Reference | Protein NCBI Reference |
|---|---|---|---|
| H. sapiens | GPT | NM_005309.2 | NP_005300.1 |
| M. mulatta | GPT | XM_001093616.2 | XP_001093616.1 |
| C. lupus | GPT | XM_847258.2 | XP_852351.2 |
| B. taurus | GPT | NM_001083740.1 | NP_001077209.1 |
| M. musculus | Gpt | NM_182805.2 | NP_877957.1 |
| R. norvegicus | Gpt | NM_031039.1 | NP_112301.1 |
| D. rerio | gpt21 | NM_001142774.1 | NP_001136246.1 |
| D. rerio | LOC100148522 | XM_001919861.2 | XP_001919896.1 |
| S. cerevisiae | ALT1 | NM_001181976.1 | NP_013190.1 |
| K. lactis | KLLA0F19162g | XM_455940.1 | XP_455940.1 |
| S. pombe | SPBC582.08 | NM_001021084.1 | NP_595176.1 |
| 318829 | MGG_06503 | XM_369988.2 | XP_369988.2 |
| N. crassa | NCU03973 | XM_952519.2 | XP_957612.1 |
| A. thaliana | ALAAT2 | NM_105892.4 | NP_565040.2 |
| A. thaliana | AlaAT1 | NM_101591.5 | NP_173173.3 |
| O. sativa | Os10g0390500 | NM_001071039.1 | NP_001064504.1 |

-continued

| Species | Protein | Genbank Accession No. | NCBI Reference |
|---|---|---|---|
| Thermococcus sp. | Alanine aminotransferase | AEK72704.1 | |
| Thermococcus sp. | Aspartate aminotransferase | EEB72915.1 | YP_002581272.1 |
| Thermococcus barophilus | Aspartate aminotransferase | ADT83250.1 | YP_004070473.1 |
| Thermococcus zilligii | Alanine aminotransferase | | ZP_11216073.1 |
| Thermococcus sp. | aminotransferase 2 | AFL94660.1 | YP_006424454.1 |
| Thermococcus gammatolerans | Alanine aminotransferase | ACS33579.1 | YP_002959443.1 |
| Thermococcus onnurineus | Alanine aminotransferase | ACJ15716.1 | YP_002306613.1 |
| Thermococcus sibiricus | Alanine aminotransferase | ACS90484.1 | YP_002994833.1 |
| Thermococcus kodakarensis | alanine aminotransferase | BAD85283.1 | YP_183507.1 |
| Thermococcus litoralis | Alanine aminotransferase | AAK98527.1 | ZP_09730551.1 |
| Pyrococcus yayanosii | Alanine aminotransferase | AEH24862.1 | YP_004624134.1 |
| Pyrococcus sp. | alanine aminotransferase | AEC52815.1 | YP_004424819.1 |
| Pyrococcus sp. | alanine aminotransferase | AFK22834.1 | YP_006354909.1 |
| Pyrococcus horikoshii | alanine aminotransferase | | NP_143210.1 |
| Pyrococcus abyssi | alanine aminotransferase | | NP_126507.1 |
| Pyrococcus furiosus | Chains A, B, C and D alanine aminotransferase | | 1XI9_A |

The target gene or nucleotide sequence may be, but not necessarily, modified as required. For example, the gene or nucleotide sequence may be modified to be transcribable and translatable in a plant system; for example, the gene or nucleotide sequence can be modified such that it contains all of the necessary poly-adenylation sequences, start sites and termination sites which allow the coding sequence to be transcribed into messenger ribonucleic acid (mRNA) and the mRNA to be translated into a functional protein in the selected plant system. Further, the target gene or nucleotide sequence may be modified such that its codon usage is more similar to that of native genes or nucleotide sequences or nucleotide sequences of the selected plant. Such target gene or nucleotide sequence modifications and the methods by which they may be made are well known in the art.

The methods and genetic constructs disclosed herein may be used to produce a plant or a plant part of any species capable of utilizing the promoter such that the transgenic plant, or non-natural plant, has tissue-specific expression of one or more desired genes or nucleotide sequences. Both monocotyledenous and dicotyledenous plants are amenable to such alteration. The invention is intended to be particularly applicable to, for example, crop plants (especially those of the genus *Oryza*), ornamental plants, and trees (particularly conifers and the genus *Populus*). Particularly suitable plants for the practice of the present invention include, but are not limited to, canola, barley, sugar cane, corn, canola, tobacco, soybean, cotton, alfalfa, tomato, wheat, potato, aspen, cottonwood, *Arabidopsis thaliana*, conifers and poplar, or parts of any of these plants, for example, roots, root tips, leaves, stems, flowers, apical buds, meristematic tissues, and the like.

The transgenic plants (non-natural plants), plant parts, and seeds produced according to the present invention may be further useful in breeding programs for the production of plant species having more than one desired trait. For example two transgenic plants of the invention each having expression of a desired transgene in differing plant tissues may be crossed to result in progeny transgenic plants having tissue-specific expression of both transgenes; or two transgenic plants of the invention each having expression of a different desired transgene in the same plant tissue may be crossed to result in progeny transgenic plants having tissue-specific expression of both transgenes. In this fashion it is possible to produce transgenic plants having a combination of desirable traits in selected tissue(s) of the plant.

Furthermore, it will be understood by one skilled in the art that different species of plants may be more or less amenable to genetic manipulation in general, and that, therefore, it may be advantageous to first transform a related species of the desired plant by the methods and with the constructs of the invention and to subsequently introduce the tissue-specific expression of the target gene or nucleotide sequence into the desired plant species by cross-breeding techniques. Such techniques and appropriately related plant species are well known to one skilled in the art.

Plant cells or protoplasts that have been transformed with the gene constructs of the present invention can be regenerated into differentiated plants using standard nutrient media supplemented with shoot-inducing or root-inducing hormone, using methods known to those skilled in the art (see, for example, Shahin, E. A. U.S. Pat. No. 4,634,674 and references therein, incorporated herein by reference in their entirety). Seeds may additionally be harvested from such transgenic plants using methods well known in the art and further used to re-grow the transgenic plants and hybrids of the invention.

Uses of the Invention

The methods and constructs of the invention allow the production of plants and seeds having expression of one or more desired genes or nucleotide sequences in one or more selected tissues of the plant. Thus, the methods and constructs of the invention permit the production of plants having one or more desired traits limited to selected plant tissues, thereby enabling the targeting of a trait to the tissue to which it is best suited, or avoiding the expression of a desirable gene or nucleotide sequence in a tissue where its effects are unwanted. There are a wide variety of specific applications of the invention, including, but not limited to, the production of plants having increased yield, stress tolerance, having improved nutrient uptake and/or utilization, having improved nutrient content and/or yields of desired compounds. Specific applications of the invention are further described below.

One application of the invention is in the production of plants better able to thrive on nutrient-poor soils. It is well known in the art that certain plant species, particularly crop plants, deplete the soil of nutrients necessary to sustain growth, such as nitrogen, phosphate, and potassium. In order to replenish the lacking nutrients, it is necessary either to fertilize the soil (an expensive and environmentally damaging procedure) or to cultivate plants known to deposit the depleted nutrient into the soil (e.g., clover or soybean in the case of nitrogen depletion), which may be crops that are less profitable or nutritive and therefore less desirable to grow. Frequent fertilizing to maintain optimal nutrients in the soil is costly in terms of agriculture outputs such as labour and fuel therefore crop plants are usually in a state of either nutrient abundance or depletion. Another application of the invention is in the production of plants better able to capture and utilize nitrogen when it is present in either an adequate or abundant supply in the soil before nitrogen loss due to leaching, volatilization or microbial degradation occurs. The methods of the invention permit the targeted expression of genes or nucleotide sequences involved in nutrient uptake (e.g., transport molecules) to those tissues in which the uptake occurs (e.g., the root or root hairs) to thereby improve the ability of the plant to absorb the nutrient from the environment. The invention may also be used to produce plants which express heterologous nutrient utilization nucleotide sequences, or optimized (for example, optimized for plant expression) native nutrient utilization nucleotide sequences, in selected tissues (e.g., the root or leaves) that permit more efficient use of the nutrient, such that less of the nutrient is required for the normal growth and functioning of the plant. Further, it is possible, using the methods of the invention, to express genes or nucleotide sequences involved in the use and uptake of nutrients not normally used by the plant in those plant tissues which are directly exposed to the different nutrient (e.g., root and leaf). In this fashion, plants which are able to grow and thrive on different nutrient sources (e.g., different nitrogen sources) may be produced.

Development of Novel Cereal Crops:

As described below, *Oryza sativa* (rice) plants may be transformed with novel gene contracts such that the plants ectopically express a nucleotide sequence encoding an enzyme involved in nitrogen assimilation or metabolism, for example, but not limited to, alanine dehydrogenase, glutamine synthetase, asparagine synthetase, glutamate synthase, asparaginase, glutamate dehydrogenase, aspartate aminotransferase, alanine aminotransferase, and those nucleotide sequences which may be involved in Nutrient Use Efficiency described by Beatty et al. (2009), and U.S. Pat. No. 7,589, 257. The present invention contemplates transformation of *Oryza sativa* with a novel gene construct, as described above, operatively linked to a tissue-specific promoter. The transformed plant is grown under laboratory conditions to determine the beneficial effects of tissue-specific expression on plant growth and yield under controlled growth conditions.

As indicated in Example 4 below, transgenic plants expressing a gene or nucleotide sequence encoding an enzyme involved in nitrogen assimilation or metabolism under the control of a tissue-specific promoter (pPBpr1) exhibited higher biomass and seed weight than those plants expressing a gene or nucleotide sequence expressed under a constitutive promoter (maize ubiquitin 1 promoter, ubi-1) in the presence of an adequate supply of nitrogen.

Transgenic *Oryza* plants ectopically expressing a gene or nucleotide sequence encoding an enzyme involved in nitrogen assimilation or metabolism under the control of a tissue-specific promoter (pPBpr1) are also capable of optimising the utilization of available nitrogen under a range of environmental conditions thereby resulting in an increase in plant biomass, seed weight or a combination thereof.

Therefore, the present invention provides a method for increasing seed yield of a plant comprising; transforming the plant with a target gene or nucleotide sequence in operative linkage with a promoter element, to produce a transformed plant, the target gene or nucleotide sequence encoding an enzyme involved in nitrogen assimilation or metabolism; and growing the transformed plant.

The above description is not intended to limit the claimed invention in any manner, furthermore, the discussed combination of features might not be absolutely necessary for the inventive solution.

The present invention will be further illustrated in the following examples. In order to assess whether enzyme isoforms of AlaAT have different kinetics and if different isoforms favor an NUE phenotype, AlaAT from mouse and *Pyrococcus* were tested.

EXAMPLES

Materials and Methods

Expression Vector Construction and *Arabidopsis thaliana* Transformation

The alanine aminotransferase enzymes assayed were chosen based on differences in their amino acid sequence as described by McAllister et al. 2012 (see also FIG. 17) and the availability of a cloned gene. *Hordeum vulgare* AlaAT (GenBank accession no. Z26322) (HvAlaAT) cDNA, described by Muench and Good (1994), as well as the pCAMBIA 1300 vector containing HvAlaAT driven by an OsANT1 promoter (OsANT1:HvAlaAT) and OsANT1 promoter driving β-glucuronidase (Shrawat et al., 2008) were obtained from Ashok Shrawat, University of Alberta. Mouse (*Mus musculus*) AlaAT1 (MmAlaAT1) (GenBank accession no. NP_877957) and mouse (*Mus musculus*) AlaAT2 (MmAlaAT2) (GenBank accession no. NP_776291) were both obtained from Rong ze Yang, University of Maryland (Yang et al., 2009). *Pyrococcus furiosus* AlaAT (PfAlaAT) (GenBank accession no. NP_579226) was amplified from ATCC gDNA (DSM 3638). Restriction enzyme cut sites were incorporated at the 5 and 3 prime ends of each cDNA using primers specific to each AlaAT as outlined in detail in McAllister et al., 2012. HvAlaAT construction of the AlaAT plasmids was done as outlined in McAllister et al., 2012. The nucleotide sequences of barley (*Hordeum vulgare*) AlaAT, mouse (*Mus musculus*) AlaAT1, and *Pyrococcus furiosus* AlaAT used herein are provided as FIGS. 11, 13 and 14, respectively (SEQ ID NOs: 1, 3 and 4, respectively). Mouse (*Mus musculus*) AlaAT2 is as previously described. The final AlaAT constructs for transformation into *Arabidopsis thaliana*, the initial AlaAT source, the promoter used to drive AlaAT expression in vivo, as well as the binary vectors utilized for transformation are summarized in Table 1.

TABLE 1

List of promoters, genes and sequences used to build the specific expression vectors for transformation into *Arabidopsis thaliana*.

| Vector Name | Promoter | Gene | Accession # | Terminator | Vector Backbone |
|---|---|---|---|---|---|
| Arabidopsis | 2XCaMV35S | HvAlaAT | Z26322 | nos | binary vector pMDC32 |
| Arabidopsis | 2XCaMV35S | Mm1AlaAT | NP_877957 | nos | binary vector pMDC32 |
| Arabidopsis | 2XCaMV35S | Mm2AlaAT | NP_776291 | nos | binary vector pMDC32 |
| Arabidopsis | 2XCaMV35S | PfAlaAT | NP_579226 | nos | binary vector pMDC32 |
| Arabidopsis | OsAnt1 | HvAlaAT | Z26322 | nos | binary vector pMDC32 |

Binary vectors were transformed into *Agrobacterium tumefaciens* strain GU3101 and selected using kanamycin. *Agrobacterium* cultures ($OD_{600}$ 0.3-0.7) were then used to transform *Arabidopsis thaliana* plants, both COL (ecotype Columbia background) and alaat1;2 knockout backgrounds, using floral dip (alaat1;2 knockout background is explained in detail in Miyashita, 2008). Transformed plants were selected by sowing seeds on hygromycin (Hyg) and using a protocol modified from Harrison et al. (2006), with plants left covered at 4° C. for 4 days and at room temperature for 3 days; PCR was carried out on all primary transgenics with primers specific to the AlaAT insert: for HvAlaAT, 5'-GAG-GTTCTTGCCCTTTGTGA-3' (SEQ ID No: 19) and 5'-TTCAGCTCGTTGCAAGTAA-3' (SEQ ID No: 20); for MmAlaAT1, 5'-CCAGAGGATGCCAAGAGAAG-3' (SEQ ID No: 21) and 5'-GCTCCGTGAGTTTAGCCTTG-3 (SEQ ID No: 22)'; for MmAlaAT2, 5'-GCAGGCTTGTGGTG-GAAA-3' (SEQ ID No: 23) and 5'-GCACTTTCT-TAAAGGAGTGGAATC-3' (SEQ ID No: 24); for PfAlaAT, 5'-GCGCTCTACGACAAAAAGACACTTGA-3' (SEQ ID No: 25) and 5'-CGTTAGTCCTGCTATAGCTGCGAATT-3' (SEQ ID No: 26). T3 seed was sown on Hyg media to select for homozygous lines; PCR was used to verify the presences of the specific AlaAT insertions. Three independent *Arabidopsis* insertion lines for each AlaAT construct, in both COL and alaat1;2 knockout backgrounds, were selected for and used for future analyses.

Plate Assays

Sterilized seeds were stratified in 0.15% (w/v) agar for approximately 48 hrs; sterilized seeds were sown onto square 100×100×15 mm petri plates containing modified ½ MS media (0.5% (w/v) sucrose and 0.8% (w/v) agar) with 0 mM $KNO_3^-$, 2 mM $KNO_3^-$, 0.25 mM $KNO_3^-$, 2.5 mM alanine or 2.5 mM glutamate as the sole nitrogen source. Seeds from both control lines, COL and alaat1;2, as well as three independent insertion lines each of OsANT1:HvAlaAT, CaMV35S:PfAlaAT, CaMV35S:HvAlaAT, CaMV35S:MmAlaAT1 and CaMV35S:MmAlaAT2, in both a COL and an alaat1;2 knockout background, were used for analysis on 0 mM, 0.25 mM and 2 mM $KNO_3^-$ plates.

Transgenic plants containing OsANT1:HvAlaAT, CaMV35S:PfAlaAT and CaMV35S:MmAlaAT1, in both COL and alaat1;2 knockout backgrounds, were used for analysis on 2.5 mM glutamate and alanine. Plants were sown horizontally across square petri plates approximately 2 cm from the top of each plate; 6 plants were sown per plate. Control plants and transgenics were sown on the same plates in an alternating fashion. Three independent insertion lines for each AlaAT were assayed in quadruplicate along with control plants. Plants were grown vertically at 21° C., 60% humidity and a lighting cycle of 16 light/8 dark. Chambers were blocked for variations in lighting conditions, resulting in four blocks, with final lighting blocks containing a maximum difference of 20% across a single block with an average light intensity of 170 $\mu E$ $m^{-2}$ $sec^{-1}$. Plates were moved within lighting blocks daily and monitored for changes in growth and development. Changes in vertical tap root length were measure (cm) between 0-5 after sowing (DAS), 5-8 DAS and 8-12 DAS for plants grown on 2 mM and 0.25 mM $KNO_3^-$. The vertical growth of tap roots of plants grown on 2.5 mM glutamate and alanine was measured (cm) between 0-5, 5-8, 8-12, 12-15, 18 and 21 DAS for changes in root length. Changes in tap root lengths over these time periods were then used to analyze the rate of tap root growth between transgenics and controls. At 18 DAS or 21 DAS (earlier if plants were senescing or had grown too large for plates) tap root lengths were measured (cm) on all ½ MS plates (top of hypocotyl to root tip).

½ MS plates were also prepared varying nitrogen and carbon amounts. Modified ½ MS (0.8% (w/v) agar) containing 1 mM $KNO_3^-$ and 0% (w/v) sucrose was used to grow transgenic plants containing OsANT1:HvAlaAT, CaMV35S:PfAlaAT and CaMV35S:MmAlaAT1, in both COL and alaat1;2 knockout backgrounds, as well as control lines, in two different lighting conditions: ~170 $\mu E$ $m^{-2}$ $sec^{-1}$ (high) and ~100 $\mu E$ $m^{-2}$ $sec^{-1}$ (low) (see FIG. 3A). Modified ½ MS containing 0.25 mM $KNO_3^-$ and 0.2% (w/v) sucrose was also used to grow all of the above lines in a low light condition (~100 $\mu E$ $m^{-2}$ $sec^{-1}$) (see FIG. 3B). Changes in vertical tap root length were measured (cm) between 0-5 DAS, 5-8 DAS, 8-12 DAS and 12-15 DAS for all plates (top of hypocotyl to root tip) to assess the rate of tap root growth between transgenic and control lines. Plating, blocking and data collection, as well as chamber conditions for the growth of plants on these plates, was as outlined previously.

Phenotypic similarity between individual plant lines expressing the same AlaAT construct in all plating conditions was assessed via one-way ANOVA ($\alpha$=0.05, P value<0.05). Final tap root lengths of control plants and transgenic lines were compared using two-way ANOVA (P value<0.05), analyzing the genotype of plants and the lighting block plants were grown in.

Analysis of AlaAT Primary Structure

The enzymes with AlaAT activity that were obtained for expression studies and kinetic analysis and the amino acid sequences were compared using ClustalW software (full primary sequence comparison is provided in McAllister et al. 2012 (see FIG. 17).

Construction of Binary Vectors and *Agrobacterium* Mediated Transformation

The sequences of the genes using in the cloning are described in FIGS. 11 and 13-16 (SEQ ID NOs: 1 and 3-7, respectively) and the components for the gene constructs are provided in FIG. 1. PBpr1 promoter (SEQ ID NO: 5) was selected for tissue-specific expression in rice (*Oryza sativa* c.v. Nipponbare (NB)) and designed to be cloned using GeneArt (Invitrogen, Life Technologies, Carlsbad, Calif., USA). The constitutive promoter, maize Ubiquitin 1 promoter (SEQ ID NO: 6) was selected for expression in rice (*Oryza sativa* c.v. Nipponbare (NB)). The HvAlaAT cDNA (SEQ ID NO: 1) was introduced into pCAMBIA1300.

The constructs were transformed separately into *Agrobacterium tumefaciens* strain EHA105 by the freeze thaw method (Weigel and Glazebrook, 2002). The transformation of *Arabidopsis thaliana* is as described above.

Rice callus (*Oryza sativa* c.v. Nipponbare (NB)) was transformed with constructs, using an *Agrobacterium* transformation system developed in our laboratory (Shrawat and Good, 2011). The final AlaAT constructs for transformation into *Oryza sativa* c.v. Nipponbare (NB), the initial AlaAT source, the promoter used to drive AlaAT expression in vivo, as well as the binary vectors utilized for transformation are summarized in Table 2.

TABLE 2

List of promoters, genes and sequences used to build the specific expression vectors for transformation into *Oryza sativa*.

| Vector Name | Promoter | Gene | Accession # | Terminator | Vector Backbone |
|---|---|---|---|---|---|
| pGPMn | PBpr1 | Mm1AlaAT | NP_877957 | nos | pGPro2 |
| pGPPn | PBpr1 | PfAlaAT | NP_579226 | nos | pGPro2 |
| pGUMn | UBi1 | Mm1AlaAT | NP_877957 | nos | pGPro2 |
| pGUPn | UBi2 | PfAlaAT | NP_579226 | nos | pGPro2 |

EXAMPLE 1

Figure 2B:
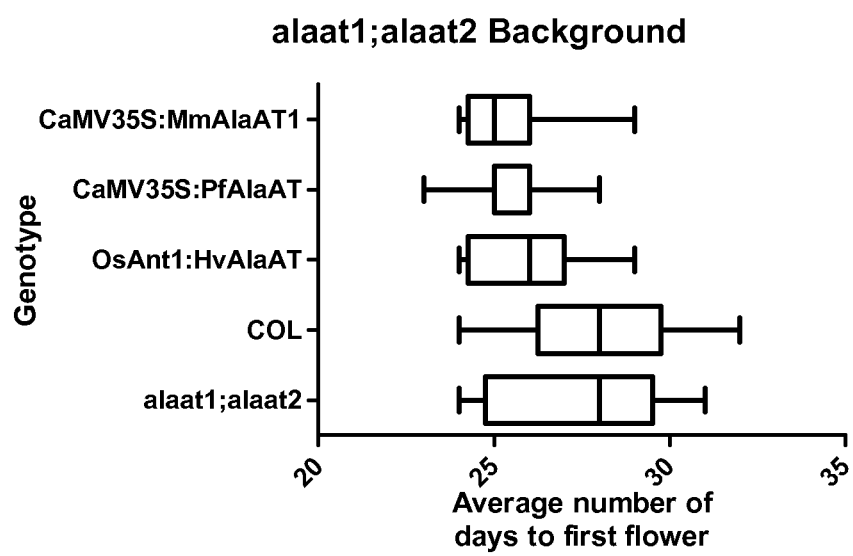

Novel AlaAT gene constructs (CaMV35S::MmAlaAT1; CaMV35S::PfAlaAT; and OsAnt1::HvAlaAT1) were introduced into either the alaat1;2 double knock out (DNK) (FIG. 2B) or the normal genetic background (COL background) (FIG. 2A).

The novel AlaAT gene constructs reduced the time to flowering in the transgenic Arabidopsis thaliana.

Figure 3A:
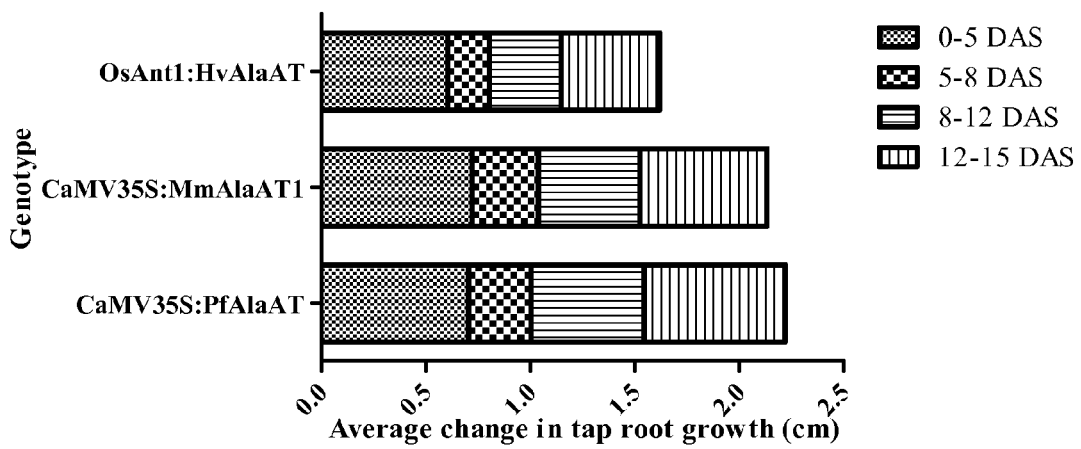
FIGS. 3A and 3B show the effects of specific constructs introduced into the ecotype Columbia on average change in tap root growth (cm) over time (DAS=days after inbibition/starting) under two different conditions.
Figure 3B:
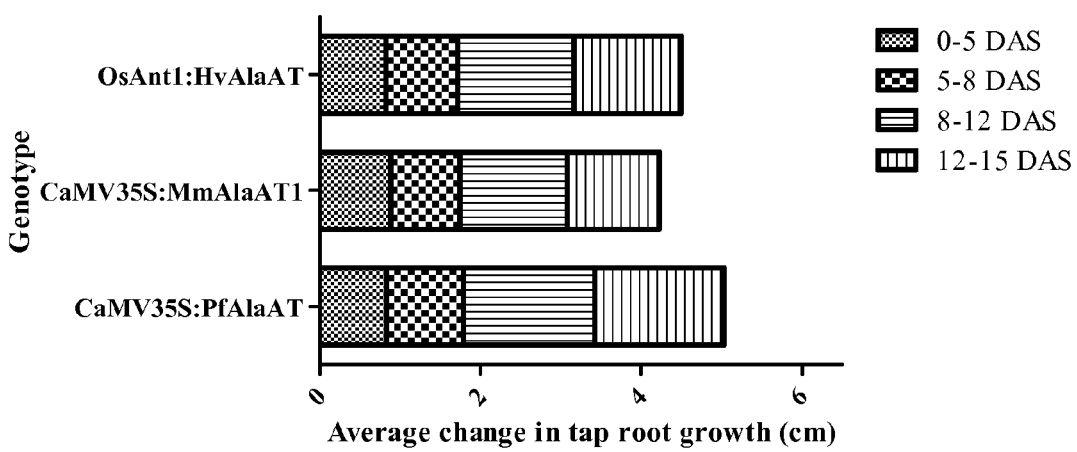
Figure 4:
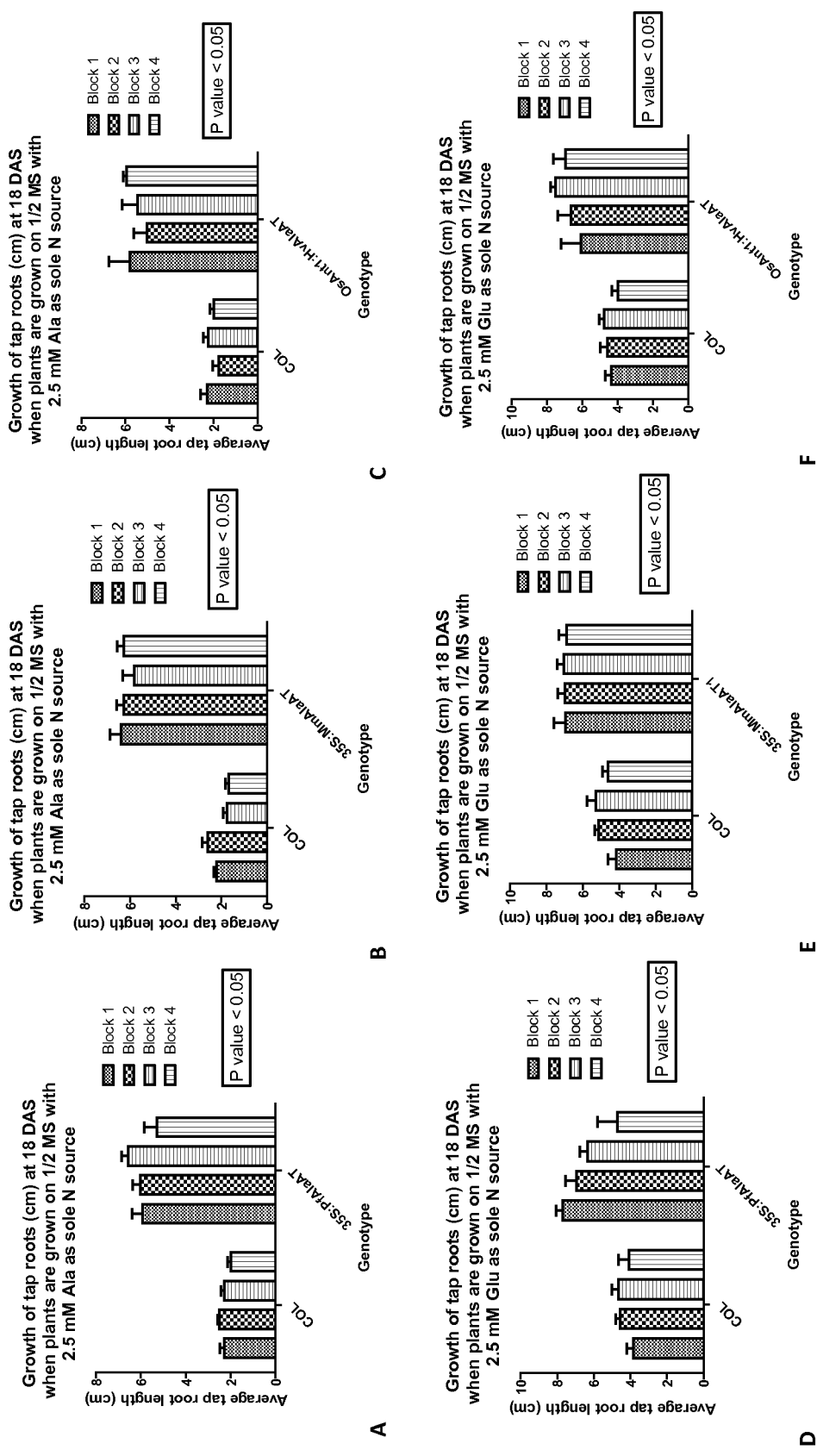
FIG. 4 shows *Arabidopsis* plants grown on modified ½ MS (Murashige and Skoog medium) supplemented with 2.5 mM alanine as the sole N source at 18 DAS. WT (COL) and AlaAT over-expressers (OE) were grown on the same plate and "blocks" are replicates that were moved accordingly. OE lines are a COL background. A: 35S::PfAlaAT; B: 35S::MmAlaAT; C: OsAnt1::HvAlaAT; D: 35S::PfAlaAT; E: 35S::MmAlaAT; F: OsAnt1::HvAlaAT.

Furthermore, the introduction of a novel AlaAT gene into either the normal genetic background or the DNK background, under two different conditions (as described above) increases the rate of root growth of the transgenic plant, and this rate changes as the plants get older (see FIGS. 3A and 3B). FIG. 3A illustrates the rate of tap root growth (cm) over 0-5, 5-8, 8-12 and 12-15 DAS with no sucrose added to the medium and 1 mM nitrate as the nitrogen source. FIG. 3B 3A illustrates the rate of tap root growth (cm) over 0-5, 5-8, 8-12 and 12-15 DAS with 0.2% sucrose added to the medium and 0.25 mM nitrate as the nitrogen source. The comparison between the two conditions suggests that the level of carbon availability or carbon/nitrogen ratio may have some impact on the rate of root development.

The effect of the novel AlaAT gene constructs (CaMV35S::MmAlaAT1; CaMV35S::PfAlaAT; and OsAnt1::HvAlaAT1) introduced into the normal genetic background (COL background) on root growth in Arabidopsis plants was determined at 18 DAS. As noted above, these plants were grown on ½ MS with 2.5 mM alanine or 2.5 mM glutamate as the only nitrogen source. The CaMV35S:PfAlaAT and CaMV35S:MmAlaAT grew significantly larger than the COL control; and both of them grew better than the OsANT1 promoter driving HvAlaAT. COL and AlaAT over-expressers (OE) were grown on the same plate and blocks are replicates that were moved accordingly.

EXAMPLE 2

Figure 5:
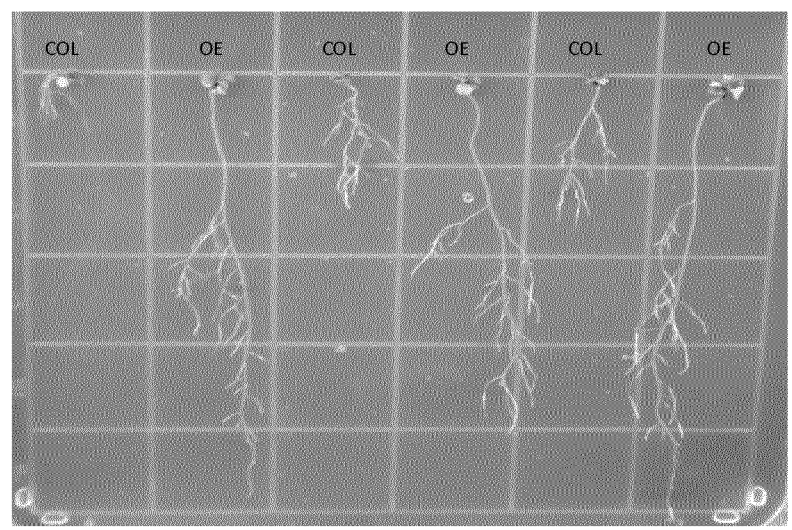
FIG. 5 shows *Arabidopsis* plants grown on modified ½ MS supplemented with 2.5 mM alanine as the sole N source at 21 DAS. WT (COL) and AlaAT over-expressers (OE) were grown on the same plate. OE lines are a COL background over-expressing MmAlaAT1 (35S:MmAlaAT1 line 2-1-7).

In FIG. 5, wild-type Arabidopsis plants and transgenic Arabidopsis plants over-expressing CaMV35S::MMAlaAT1 were grown on modified ½ MS supplemented with 2.5 mM alanine as the sole nitrogen source. WT and AlaAT over-expressers (OE) were grown on the same plate. OE lines are a COL background over-expressing MmAlaAT1 (35S: MmAlaAT1 line 2-1-7).

Figure 6:
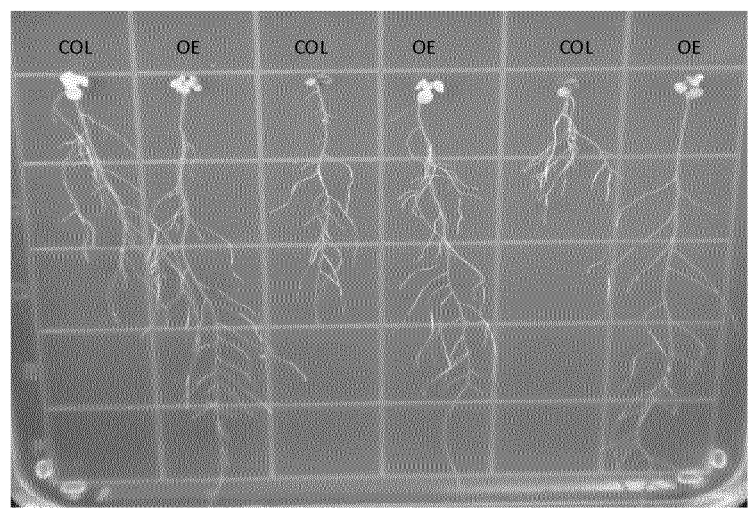
FIG. 6 shows *Arabidopsis* plants grown on modified ½ MS supplemented with 2.5 mM glutamate as the sole N source. WT (COL) and AlaAT over-expressers (OE) were grown on the same plate. OE lines are a COL background over-expressing PfAlaAT (35S:PfAlaAT line 4-1).

In FIG. 6, wild-type Arabidopsis plants and transgenic Arabidopsis plants over-expressing CaMV35S::PfAlaAT were grown on modified ½ MS supplemented with 2.5 mM glutamate as the sole nitrogen source. WT and AlaAT over-expressers (OE) were grown on the same plate. OE lines are a COL background over-expressing PfAlaAT (35S: PfAlaAT line 4-1-2).

FIGS. 5 and 6 demonstrate that when a novel AlaAT gene is driven by the correct promoter, it has a significant effect on root growth, root length and overall root branching.

EXAMPLE 3

Figure 7:
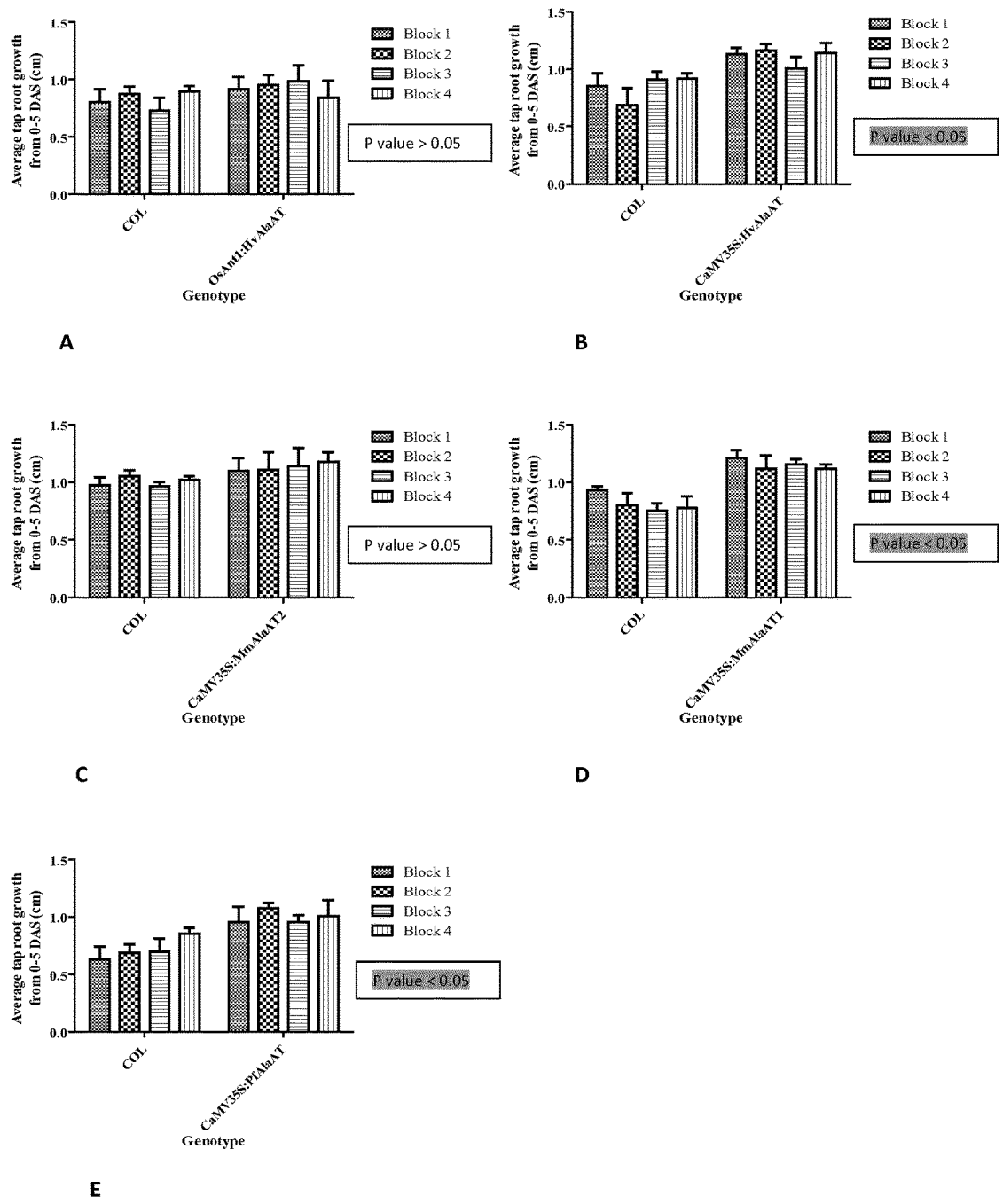
FIG. 7 shows the change in tap root growth (cm) between 0-5 DAS of control (COL) and AlaAT over-expressers (OE) in COL background grown on modified ½ MS supplemented with 0.25 mM $NO_3^-$ as the sole N source. A: OsAnt1::HvAlaAT; B: 35S::HvAlaAT; C: 35S::MmAlaAT2; D: 35S::MmAlaAT1; E: 35S::PfAlaAT.

In FIG. 7, wild-type Arabidopsis plants and transgenic Arabidopsis plants over-expressing novel AlaAT genes (Os-Ant1::HvAlaAT; CaMV35S::HvAlaAT; CaMV35S::MMAlaAT1; CaMV35S::MMAlaAT2; and CaMV35S::PfAlaAT) in a COL background were grown on modified ½ MS supplemented with 0.25 mM $KNO_3^-$ as the sole nitrogen source. The change in tap root growth (cm) between 0-5 DAS was measured.

Figure 8:
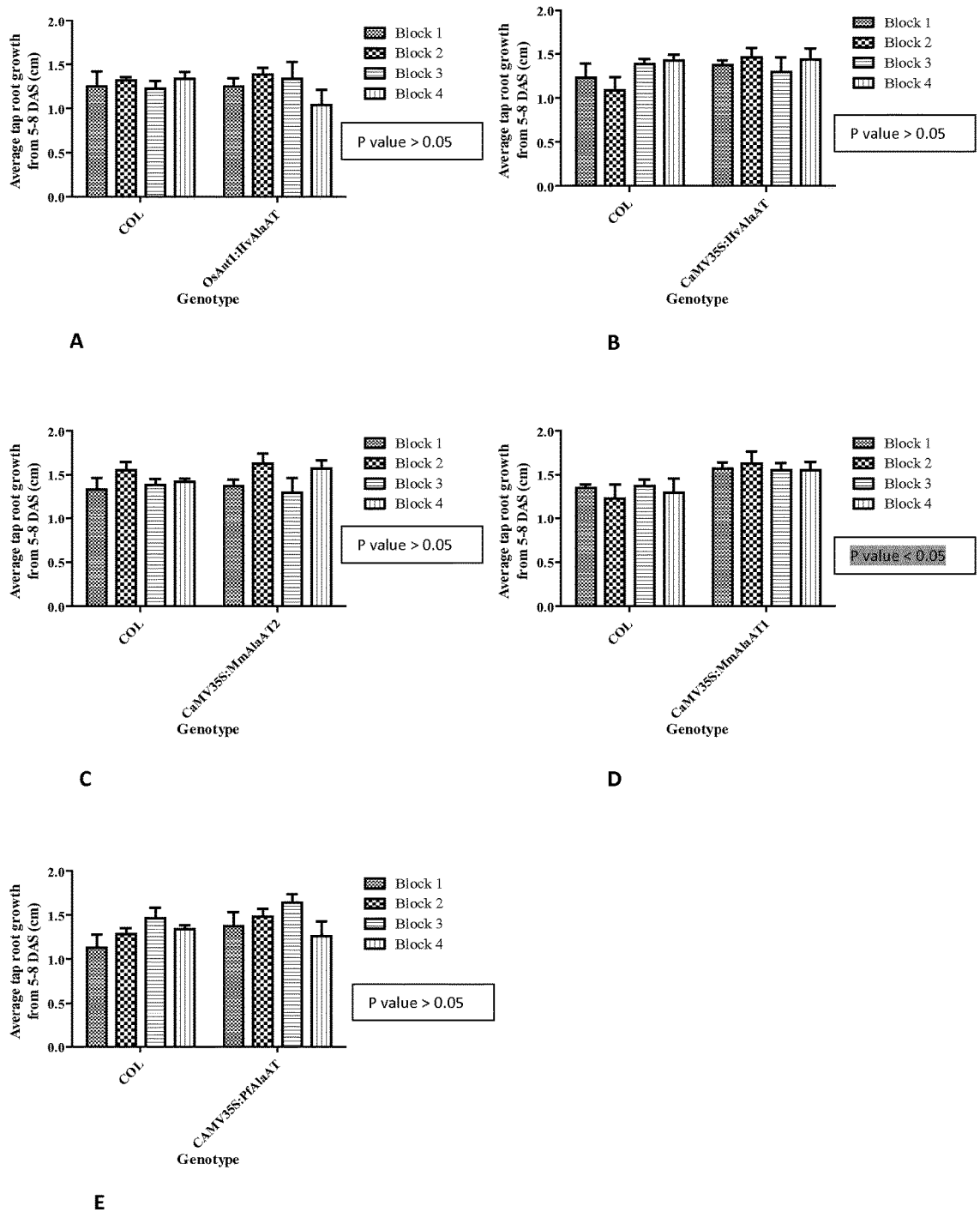
FIG. 8 shows the change in tap root growth (cm) between 5-8 DAS of control (COL) and AlaAT over-expressers (OE) in COL background grown on modified ½ MS supplemented with 0.25 mM $NO_3^-$ as the sole N source. A: OsAnt1::HvAlaAT; B: 35S::HvAlaAT; C: 35S::MmAlaAT2; D: 35S::MmAlaAT1; E: 35S::PfAlaAT.

In FIG. 8, wild-type Arabidopsis plants and transgenic Arabidopsis plants over-expressing novel AlaAT genes (Os-Ant1::HvAlaAT; CaMV35S::HvAlaAT; CaMV35S::MMAlaAT1; CaMV35S::MMAlaAT2; and CaMV35S::PfAlaAT) in a COL background were grown on modified ½ MS supplemented with 0.25 mM $KNO_3^-$ as the sole nitrogen source. The change in tap root growth (cm) between 5-8 DAS was measured.

Figure 9:
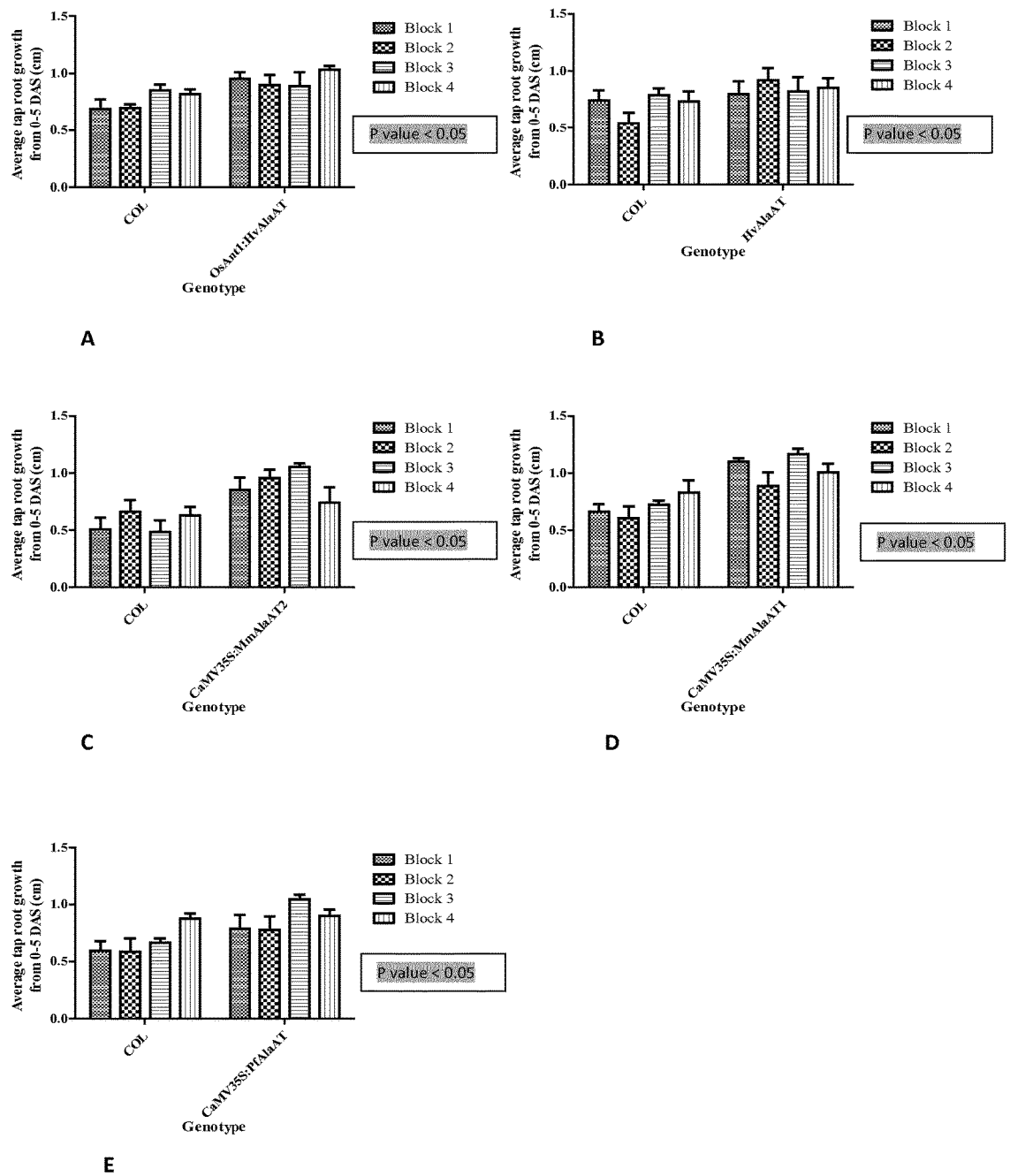
FIG. 9 shows the change in tap root growth (cm) between 0-5 DAS of control (COL) and AlaAT over-expressers (OE) in COL background grown on modified ½ MS supplemented with 2 mM $NO_3^-$ as the sole N source. A: OsAnt1::HvAlaAT; B: 35S::HvAlaAT; C: 35S::MmAlaAT2; D: 35S::MmAlaAT1; E: 35S::PfAlaAT.

In FIG. 9, wild-type Arabidopsis plants and transgenic Arabidopsis plants over-expressing novel AlaAT genes (Os-Ant1::HvAlaAT; CaMV35S::HvAlaAT; CaMV35S::MMAlaAT1; CaMV35S::MMAlaAT2; and CaMV35S::PfAlaAT) in a COL background were grown on modified ½ MS supplemented with 2 mM $KNO_3^-$ as the sole nitrogen source. The change in tap root growth (cm) between 0-5 DAS was measured.

Figure 10:
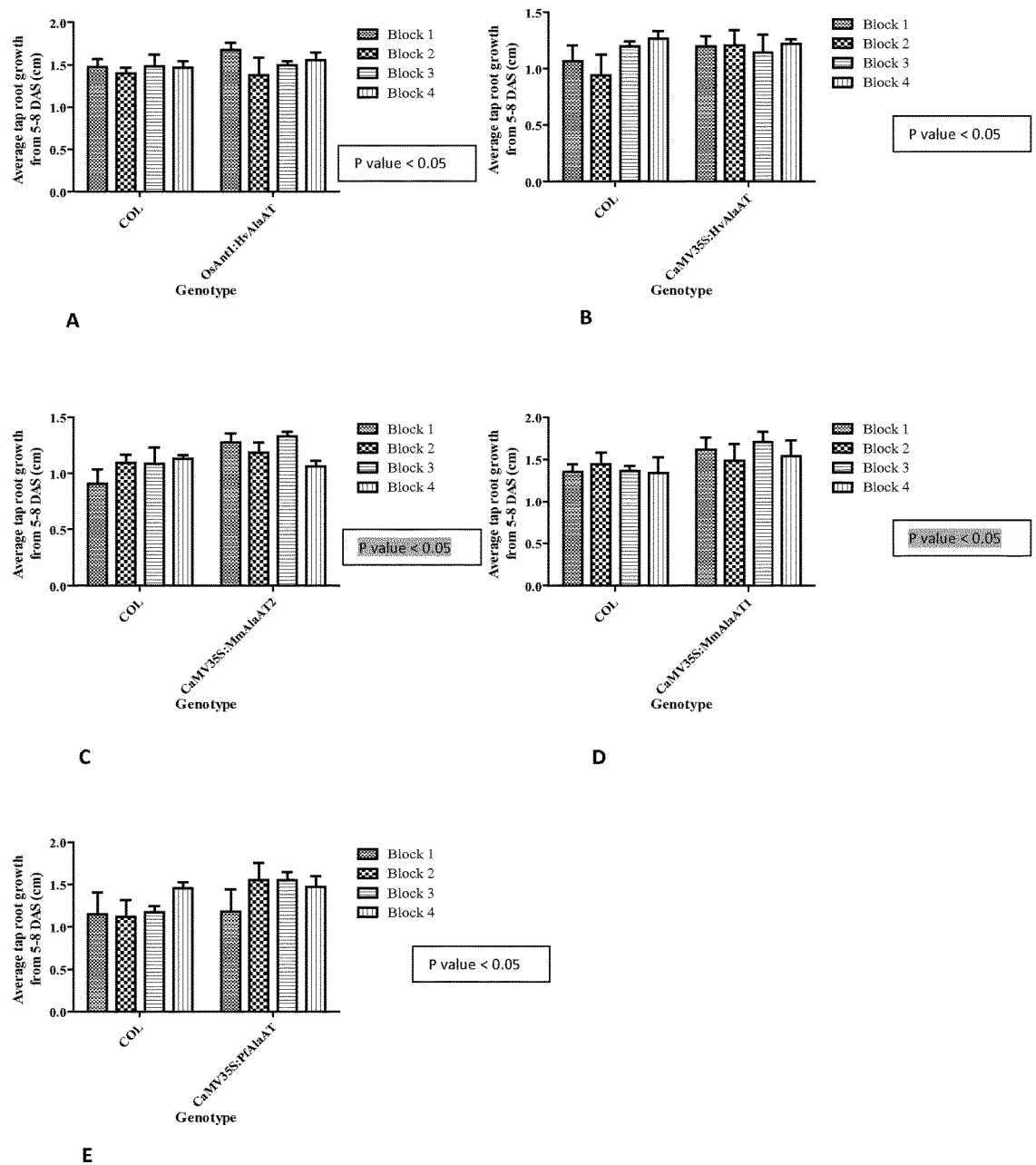
FIG. 10 shows the change in tap root growth (cm) between 5-8 DAS of control (COL) and AlaAT over-expressers (OE) in COL background grown on modified ½ MS supplemented with 2 mM $NO_3^-$ as the sole N source. A: OsAnt1::HvAlaAT; B: 35S::HvAlaAT; C: 35S::MmAlaAT2; D: 35S::MmAlaAT1; E: 35S::PfAlaAT.

In FIG. 10, wild-type Arabidopsis plants and transgenic Arabidopsis plants over-expressing novel AlaAT genes (Os-Ant1::HvAlaAT; CaMV35S::HvAlaAT; CaMV35S::MMAlaAT1; CaMV35S::MMAlaAT2; and CaMV35S::PfAlaAT) in a COL background were grown on modified ½ MS supplemented with 2 mM $KNO_3^-$ as the sole nitrogen source. The change in tap root growth (cm) between 5-10 DAS was measured.

The experiments carried out for FIGS. 7 through 10 demonstrate that when a novel AlaAT gene is driven by the correct promoter, the significant effect on root growth, and root length occurs at a very early developmental stage.

EXAMPLE 4: TRANSGENIC RICE

Heterozygous $T_0$ Seed Yield and Biomass Preliminary Screens

Transgenic rice (Oryza sativa) containing the specific genetic constructs above and outlined in FIG. 1 were produced using an Agrobacterium mediated approach, as described above. Leaf tissue was collected from two week old plants to determine if they were transgenic by means of a genomic DNA polymerase chain reaction (PCR) analysis using primers specific to the hygromycin resistance gene.

It was examined whether the amount of available nitrogen would have an effect on plant biomass and seed weight on plants expressing PBpr1::AlaAT grown under laboratory conditions when compared to similar plants that ectopically expressed the target nucleotide sequence under a constitutive promoter (maize ubiquitin 1).

Seed weights and biomass of the transgenic plants grown under laboratory conditions were examined at the dates provided below in Table 3. At the $T_0$ stage, several of the transgenic plants expressing AlaAT in a tissue-specific manner had higher above ground biomass and seed weight compared to transgenic plants expressing AlaAT in a constitute manner (Table 3).

TABLE 3

Biomass and seed weight for transgenic Oryza sativa plants expressing AlaAT in a tissue-specific or constitutive manner.

| plant # | seeding date | flowering date | prod tillers | biomass (g) | seed wt (g) |
| --- | --- | --- | --- | --- | --- |
| pGPMn1/1-1 | 12 Jun. 2012 | 28 Aug. 2012 | 10 | 31.5 | 10.88 |
| pGPMn1/1-2 | 12 Jun. 2012 | 17 Aug. 2012 | 9 | 25.73 | 10.06 |
| pGPMn1/1-3 | 12 Jun. 2012 | 19 Aug. 2012 | 10 | 27.6 | 5.67 |
| pGPMn1/1-4 | 12 Jun. 2012 | 19 Aug. 2012 | 8 | 30.26 | 11.52 |
| pGPMn1/1-5 | 12 Jun. 2012 | 27 Aug. 2012 | 14 | 31.62 | 10.11 |

TABLE 3-continued

Biomass and seed weight for transgenic *Oryza sativa* plants expressing AlaAT in a tissue-specific or constitutive manner.

| plant # | seeding date | flowering date | prod tillers | bio-mass (g) | seed wt (g) |
|---|---|---|---|---|---|
| pGPMn1/1-6 | 12 Jun. 2012 | 18 Aug. 2012 | 13 | 34.64 | 8.26 |
| pGPMn1/1-7 | 12 Jun. 2012 | 17 Aug. 2012 | 10 | 33.98 | 11.20 |
| pGPMn1/1-8 | 12 Jun. 2012 | 23 Aug. 2012 | 9 | 31.78 | 12.16 |
| pGPMn1/1-9 | 12 Jun. 2012 | 19 Aug. 2012 | 12 | 33.41 | 10.14 |
| pGPMn1/1-10 | 12 Jun. 2012 | 17 Aug. 2012 | 10 | 29.43 | 9.66 |
| pGPMn1/1-11 | 12 Jun. 2012 | 18 Aug. 2012 | 12 | 33.6 | 8.95 |
| pGPMn1/1-12 | 12 Jun. 2012 | 23 Aug. 2012 | 10 | 29.28 | 9.30 |
| pGPMn1/1-13 | 12 Jun. 2012 | 31 Aug. 2012 | 13 | 30.86 | 11.79 |
| pGPMn1/1-14 | 12 Jun. 2012 | 21 Sep. 2012 | 10 | 28.51 | 9.98 |
| pGPMn1/1-15 | 12 Jun. 2012 | 21 Sep. 2012 | 15 | 33.38 | 12.45 |
| pGPMn1/1-16 | 25 Jun. 2012 | 2 Sep. 2012 | 13 | 28.78 | 5.91 |
| pGPMn1/1-17 | 25 Jun. 2012 | 4 Sep. 2012 | 13 | 26.14 | 5.95 |
| pGPMn1/1-20 | 25 Jun. 2012 | 9 Sep. 2012 | 16 | 36.15 | 14.88 |
| pGPMn1/1-21 | 25 Jun. 2012 | 9 Sep. 2012 | 13 | 29.01 | 5.20 |
| pGPPn2/1-2 | 12 Jun. 2012 | 20 Aug. 2012 | 10 | 32.07 | 12.99 |
| pGPPn2/1-3 | 12 Jun. 2012 | 4 Sep. 2012 | 7 | 26.35 | 7.06 |
| pGPPn2/1-4 | 12 Jun. 2012 | 28 Aug. 2012 | 8 | 24.56 | 8.29 |
| pGPPn2/1-5 | 12 Jun. 2012 | 28 Aug. 2012 | 7 | 24.61 | 8.06 |
| pGPPn2/1-6 | 12 Jun. 2012 | 20 Aug. 2012 | 9 | 27.35 | 9.69 |
| pGPPn2/1-7 | 25 Jun. 2012 | 30 Sep. 2012 | 9 | 26.3 | 3.70 |
| pGPPn2/1-8 | 25 Jun. 2012 | 4 Sep. 2012 | 13 | 36.19 | 12.32 |
| pGPPn2/1-9 | 25 Jun. 2012 | 28 Aug. 2012 | 15 | 34.72 | 11.84 |
| pGPPn2/2-1 | 28 Aug. 2012 | 15 Nov. 2012 | 14 | 35.34 | 5.66 |
| pGPPn2/2-2 | 28 Aug. 2012 | 6 Nov. 2012 | 21 | 40.48 | 7.38 |
| pGPPn2/2-3 | 11 Sep. 2012 | 15 Nov. 2012 | 14 | 34.17 | 13.24 |
| pGPPn2/2-4 | 11 Sep. 2012 | 19 Nov. 2012 | 13 | 32.28 | 7.92 |
| pGPPn2/2-5 | 11 Sep. 2012 | 23 Nov. 2012 | 11 | 38.3 | 11.38 |
| pGPPn2/2-6 | 11 Sep. 2012 | 23 Nov. 2012 | 14 | 28.16 | 8.61 |
| pGPPn2/2-7 | 11 Sep. 2012 | 28 Nov. 2012 | 9 | 28.4 | 9.94 |
| pGPPn2/2-8 | 11 Sep. 2012 | 23 Nov. 2012 | 10 | 33.29 | 9.40 |
| pGUMn3/1-1 | 10 Sep. 2012 | 19 Nov. 2012 | 11 | 27.36 | 6.14 |
| pGUMn3/1-3 | 14 Sep. 2012 | 26 Nov. 2012 | 12 | 34.5 | 6.70 |
| pGUMn3/1-4 | 14 Sep. 2012 | 26 Nov. 2012 | 13 | 32.94 | 8.43 |
| pGUMn3/1-6 | 14 Sep. 2012 | 30 Nov. 2012 | 20 | 30.08 | 4.07 |
| pGUMn3/1-7 | 14 Sep. 2012 | 6 Dec. 2012 | 18 | 30.61 | 3.03 |
| pGUMn3/1-8 | 14 Sep. 2012 | 14 Nov. 2012 | 9 | 21.1 | 7.98 |
| pGUPn4/1-1 | 10 Sep. 2012 | 18 Nov. 2012 | 11 | 22.71 | 3.28 |
| pGUPn4/1-2 | 10 Sep. 2012 | 19 Nov. 2012 | 7 | 22.05 | 3.69 |
| pGUPn4/1-4 | 11 Sep. 2012 | 12 Nov. 2012 | 8 | 18.54 | 3.31 |
| pGUPn4/1-5 | 11 Sep. 2012 | 13 Nov. 2012 | 10 | 29.62 | 11.08 |
| pGUPn4/1-6 | 11 Sep. 2012 | 19 Nov. 2012 | 9 | 29.8 | 12.74 |
| pGUPn4/1-7 | 14 Sep. 2012 | 21 Dec. 2012 | 9 | 20.8 | 3.05 |
| pGUPn4/1-8 | 14 Sep. 2012 | 25 Nov. 2012 | 6 | 20.93 | 2.07 |
| pGUPn4/1-9 | 14 Sep. 2012 | 30 Nov. 2012 | 16 | 33.09 | 2.88 |
| pGUPn4/1-10 | 14 Sep. 2012 | 30 Nov. 2012 | 13 | 31.06 | 7.68 |
| pGUPn4/1-11 | 14 Sep. 2012 | 19 Nov. 2012 | 12 | 24.93 | 3.20 |
| pGUPn4/1-12 | 14 Sep. 2012 | 19 Nov. 2012 | 7 | 20.1 | 3.10 |
| pGUPn4/1-13 | 14 Sep. 2012 | 18 Nov. 2012 | 15 | 33.12 | 5.47 |

Thus, transgenic plants expressing a gene or nucleotide sequence encoding an enzyme involved in nitrogen assimilation or metabolism under tissue-specific promoter exhibited higher biomass and seed weight than plants expressing the same gene or nucleotide sequence under a constitutive promoter, in the presence of an adequate supply of nitrogen.

This indicates that transgenic *Oryza sativa* plants ectopically expressing an enzyme involved in nitrogen assimilation or metabolism are capable of optimising the utilization of available nitrogen under a range of environmental conditions thereby resulting in an increase in plant biomass, seed yield or a combination thereof.

Figure 18:
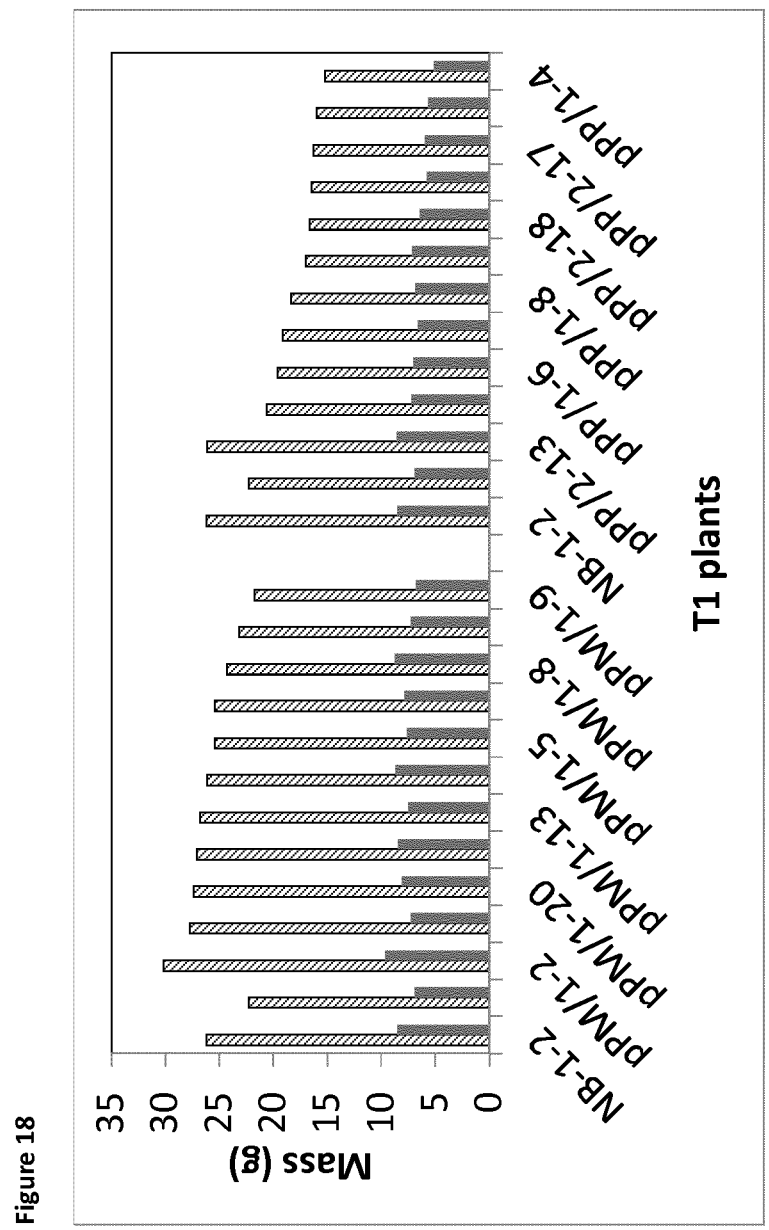
FIG. 18 shows average biomass and average seed weight from T1 transgenic *Oryza sativa* plant lines (11 lines with each 6 plants selected by biomass and seed weight). Hatched bars: average biomass; solid bars: average seed weight.

T1 plant lines were obtained and average biomass and seed-weight was determined for 6 plants per transgenic plant lines. The results are shown in FIG. 18.

Collectively the above results indicate that transgenic plants ectopically expressing an enzyme involved in nitrogen assimilation or metabolism are capable of optimising the utilization of available nitrogen under a range of environmental conditions thereby resulting in an increase in plant biomass, seed weight, root tap growth, root growth and root length or a combination thereof.

The present invention has been described with regard to one or more embodiments. However, it will be apparent to persons skilled in the art that a number of variations and modifications can be made without departing from the scope of the invention as defined in the claims All citations are hereby incorporated by reference.

REFERENCES

1. Beatty, P. H., Shrawat, A. K., Carroll, R. T., Zhu, T., and Good, A. G. (2009) Transcriptome analysis of nitrogen-efficient rice over-expressing alanine aminotransferase. *Plant Biotechnology Journal* 7, 562-576.
2. Burton, R. A., et al. (2011). Over-expression of specific HvCslF cellulose synthase-like genes or nucleotide sequences in transgenic barley increases the levels of cell wall (1,3;1,4)-β-d-glucans and alters their fine structure. *Plant Biotechnology Journal* 9, 117-135.
3. DellaPenna, D. (2001) Plant Metabolic Engineering. *Plant Physiology* 125: 160-163.
4. Duff S M G, Rydel T J, McClerren A L, Zhang W, Li J Y, et al. (2012) The enzymology of alanine aminotransferase (AlaAT) isoforms from *Hordeum vulgare* and other organisms, and the HvAlaAT crystal structure. *Arch Biochem Biophys*, doi: 10.1016/j.abb.2012.06.006.
5. Good et al., US 2009/0288224.
6. Good, A. G., Shrawat, A. K. and Muench, D. G. (2004) Can less yield more? Is reducing nutrient input into the environment compatible with maintaining crop production? *Trends Plant Sci.* 9, 597-605.
7. Good A. G. and Beatty P. H. (2011a) Biotechnological Approaches to Improving Nitrogen Use Efficiency in Plants: Alanine Aminotransferase as a Case Study. In, *The Molecular and Physiological Basis of Nutrient Use Efficiency in Crops*, First Edition. Edited by Malcolm J. Hawkesford, Peter Barraclough. John Wiley & Sons, Inc. Published 2011 by John Wiley & Sons, Inc.
8. Good A G and Beatty P H. 2011b. Fertilizing Nature: A Tragedy of Excess in the Commons. *PLoS Biol* 9(8): e1001124. doi:10.1371/journal.pbio.1001124.
9. Good, A. G., Johnson, S. J., DePauw, M. D., Carroll, R. T., Savidov, N., Vidamir, J., Lu, Z., Taylor, G. and Stroeher, V. (2007) Engineering nitrogen use efficiency with alanine aminotransferase. *Canadian Journal of Botany* 85, 252-262.
10. Greene, T. W., Kavakli, I. H., Kahn, M. L., & Okita, T. W. (1998). Generation of up-regulated allosteric variants of potato ADP-glucose pyrophosphorylase by reversion genetics. Proceedings of the National Academy of Sciences of the United States of America, 95(17), 10322-7. Retrieved from www.pubmedcentral.nih.gov/articlerender.fcgi?artid=21507&tool=pmcentrez&rendertype=abstract.
11. Harrison, S. J., Mott, E. K., Parsley, K. et al., (2006) A rapid and robust method of identifying transformed *Arabidopsis thaliana* seedlings following floral dip transformation. *Plant Methods.* 2:19 doi:10.1186/1746-4811-2-19.
12. Kasuga, M., Liu, Q., Miura, S., Yamaguchi-Shinozaki, K., and Shinozaki, K. (1999). Improving plant drought, salt and freezing tolerance by gene transfer of a single stress-inducible transcription factor. *Nature Biotechnology* 17, 287-291.
13. Lock Y. Y. (2011) Engineering nitrogen use efficiency in *Oryza sativa* by the developmental overexpression of barley alanine aminotransferase using a novel rice promoter. Master of Science thesis. University of Alberta, Edmonton, Alberta, Canada.
14. Ma Q-H (2008) Genetic engineering of cytokinins and their application to agriculture. *Critical Reviews in Biotechnology*, 28: 213-232.
15. McAllister C H, Facette M, Holt A, Good A G (2013) Analysis of the Enzymatic Properties of a Broad Family of Alanine Aminotransferases. *PLoS ONE* 8(2): e55032. doi:10.1371/journal.pone.0055032.
16. McAllister C, Beatty P H and Good A G. 2012. Engineering nitrogen use efficient crop plants; the current status. *Plant Biotechnology Journal* doi: 10.1111/j.1467-7652.2012.00700.x.
17. Miyashita, Y. and Good, A. G. (2008). NAD(H)-dependent glutamate dehydrogenase is essential for the survival of *Arabidopsis thaliana* during dark-induced carbon starvation. *Journal of Experimental Botany*, 59, 667-80.
18. Muench, D. G., and Good, A. G. (1994) Hypoxically inducible barley alanine aminotransferase: cDNA cloning and expression analysis. *Plant Molecular Biology* 24, 417-427.
19. Napoli, C., Lemieux, C., & Jorgensen, R. (1990). Introduction of a Chimeric Chalcone Synthase Gene into Petunia Results in Reversible Co-Suppression of Homologous Genes in trans. *The Plant cell*, 2(4), 279-289. doi:10.1105/tpc.2.4.279.
20. Oguchi, K., Tanaka, N., Komatsu, S., and Akao, S. (2004) Methylmalonate-semialdehyde dehydrogenase is induced in auxin-stimulated and zinc-stimulated root formation in rice. *Plant cell reports* 22, 848-858.
21. Paine, J. A. et al (2005) Improving the nutritional value of Golden Rice through increased pro-vitamin A content. *Nat. Biotechnol.* 23, 482-487.
22. Pino M-T, Skinner J. S., Park E-J et al. (2007) Use of s stress inducible promoter to drive ectopic AtCBF expression improves potato freezing tolerance while minimizing negative effects on tuber yield. *Plant Biotechnology Journal* 5, 591-604.
23. Qu, L. Q., and Takaiwa, F. (2004) Evaluation of tissue specificity and expression strength of rice seed component gene promoters in transgenic rice. *Plant Biotechnology Journal* 2, 113-125.
24. Rus, A., Baxter, I., Muthukumar, B., Gustin, J., Lahner, B., Yakubova, E., & Salt, D. E. (2006). Natural variants of AtHKT1 enhance Na+ accumulation in two wild populations of *Arabidopsis*. *PLoS Genetics*, 2(12), e210. doi: 10.1371/journal.pgen.0020210.
25. Shelton, A. M., Zhao, J., and Roush, R. T. (2002). Economic, ecological, food safety and social consequences of the deployment of BT transgenic plants. *Annual Reviews in Entomology* 47, 845-881.
26. Shrawat, A. K., and Good, A. G. (2011). *Agrobacterium tumefaciens*-mediated genetic transformation of cereals using immature embryos. *Methods in molecular biology* 710, 355-372.
27. Shrawat, A. K., Carroll, R. T., DePauw, M., Taylor, G. J. and Good, A. G. (2008) Genetic engineering of improved nitrogen use efficiency in rice by the tissue-specific expression of alanine aminotransferase. *Plant Biotechnology Journal* 6, 722-732.
28. Tao, H., & Cornish, V. W. (2002). Milestones in directed enzyme evolution. *Current opinion in chemical biology*, 6(6), 858-64. Retrieved from www.ncbi.nlm.nih.gov/pubmed/12470742.
29. Trostle, C. L., Bloom, P. R. and Allan, D. L. (2001) HEDTA-Nitrilotriacetic Acid Chelator-Buffered Nutrient Solution for Zinc Deficiency Evaluation in Rice. *Soil Sci. Soc. Am. J.* 65:385-390.
30. Weigel, D., and Glazebrook, J. (2002) *Arabidopsis*: A Laboratory Manual. Cold Spring Harbor Laboratory Press, Cold Spring Harbor, N.Y.
31. Yanagisawa, S. (2000) Dof1 and Dof2 transcription factors are associated with expression of multiple genes involved in carbon metabolism in maize. *Plant J.* 21, 281-288.
32. Yanagisawa, S., Akiyama, A., Kisaka, H., Uchimiya, H. and Miwa, T. (2004) Metabolic engineering with Dof1 transcription factor in plants: improved nitrogen assimilation and growth under low-nitrogen conditions. *PNAS*, 101, 7833-7838.
33. Yang R, Park S, Reagan W J, Goldstein R, Zhong S, et al. (2009) Alanine aminotransferase isoenzyme: molecular cloning and quantitative analysis of tissue expression in rats and serum elevation in liver toxicity. *Hepatology* 49:598-607.
34. Zhang, K., Bhuiya, M.-W., Pazo, J. R., Miao, Y., Kim, H., Ralph, J., & Liu, C.-J. (2012). An engineered monolignol 4-o-methyltransferase depresses lignin biosynthesis and confers novel metabolic capability in *Arabidopsis*. *The Plant Cell*, 24(7), 3135-52. doi:10.1105/tpc.112.101287.

The invention claimed is:

1. A transgenic plant, plant cell, or plant part comprising a polynucleotide encoding an alanine amino transferase (AlaT) protein from a non-plant organism gene operably linked to a PBpr1 promoter which comprises the nucleotide sequence of SEQ ID No. 5, wherein the polynucleotide comprises a nucleotide sequence encoding a protein having at least 80% amino acid identity to the amino acid sequence of SEQ ID No. 14 or SEQ ID No. 15 or SEQ ID No. 16.

2. The transgenic plant, plant cell, or plant part according to claim 1, wherein the plant is corn, wheat, maize, rice, barley, canola, soybean, cotton, alfalfa, safflower, tomato or potato.

3. A seed obtained from the transgenic plant according to claim 1, comprising said polynucleotide operably linked to said PBpr1 promoter.

4. The transgenic plant, plant cell, or plant part according to claim 1, wherein the plant cell is a rice plant cell, a barley plant cell, a wheat plant cell or a maize plant cell.

5. The transgenic plant, plant cell, or plant part according to claim 1, wherein the plant cell is a rice plant cell.

6. The transgenic plant, plant cell, or plant part according to claim 1, wherein the gene encoding the AlaAT protein comprises a nucleotide sequence having 95% identity to SEQ ID No. 3 or 4.

7. The transgenic plant, plant cell, or plant part according to claim 6, wherein the plant cell is a rice plant cell, a barley plant cell, a wheat plant cell or a maize plant cell.

8. A genetic construct comprising a polynucleotide encoding an alanine amino transferase (AlaT) protein from a non-plant organism operably linked to a PBpr1 promoter which comprises the nucleotide sequence of SEQ ID No. 5, wherein the polynucleotide comprises a nucleotide sequence encoding a protein having at least 80% amino acid identity to the amino acid sequence of SEQ ID No. 14 or SEQ ID No. 15 or SEQ ID No. 16.

9. The genetic construct according to claim 8, wherein the polynucleotide comprises a nucleotide sequence having 95% identity to SEQ ID No. 3 or 4.

10. A method of generating a plant having increased biomass, increased nitrogen use efficiency or increased seed yield comprising:
transforming a plant cell with the genetic construct according to claim 9, and
growing the transformed plant cell to produce a plant that expresses the protein, thereby generating a plant having increased biomass, increased nitrogen use efficiency or increased seed yield, wherein the increased biomass, increased nitrogen use efficiency or increased seed yield is relative to the biomass, nitrogen use efficiency or seed yield of a wild-type plant grown under identical conditions.

11. A method of generating a plant having increased nitrogen use efficiency, increased biomass or increased seed yield comprising:
transforming a plant cell with the genetic construct according to claim 8, and
growing the transformed plant cell to produce a plant that expresses the protein, thereby generating a plant having increased nitrogen use efficiency, increased biomass or increased seed yield, wherein the increased nitrogen use efficiency, increased biomass or increased seed yield is relative to the nitrogen use efficiency, biomass or seed yield respectively of a wild-type plant grown under identical conditions.

12. The method according to claim 11, wherein the plant is corn, wheat, maize, rice, barley, canola, soybean, cotton, alfalfa, safflower, sugarcane, tomato or potato.

13. A method for producing a plant having increased nitrogen use efficiency, increased biomass, increased seed yield, earlier development time, or a combination thereof, comprising:
growing a plant from a plant, plant part or seed, comprising the genetic construct according to claim 8, thereby producing a plant having increased nitrogen uptake, increased biomass, increased seed yield, earlier development time, or a combination thereof, wherein the increased nitrogen uptake, increased biomass and increased seed yield is relative to the nitrogen uptake, biomass and seed yield of a wild-type plant grown under identical conditions.

14. The method of claim 13, further comprising providing a fertilizer to the plant or the habitat of the plant.

15. The method of claim 14, wherein the fertilizer is a nitrogen containing fertilizer.

* * * * *

SEQUENCE LISTING

```
<160> NUMBER OF SEQ ID NOS: 26

<210> SEQ ID NO 1
<211> LENGTH: 1455
<212> TYPE: DNA
<213> ORGANISM: Hordeum vulgare

<400> SEQUENCE: 1
atggctgcca ccgtcgccgt ggacaacctg aaccccaagg ttttaaaatg tgagtatgct      60
gtgcgtggag agattgtcat ccatgctcag cgcttgcagg aacagctaaa gactcaacca     120
gggtctctac cttttgatga gatcctctat tgtaacattg ggaacccaca atctcttggt     180
cagcaaccag ttacattctt cagggaggtt cttgcccttt gtgatcatcc agacctgttg     240
caaagagagg aaatcaaaac attgttcagt gctgattcta tttctcgagc aaagcagatt     300
cttgccatga tacctgaaag agcaacagga gcatacagcc atagccaggg tattaaagga     360
```

```
cttcgtgatg caattgcttc tgggatcgct tcacgagatg gattccctgc taatgctgat    420
gacattttc tcacagatgg agcaagtcct ggggtgcacc tgatgatgca attactgata    480
aggaatgaga aagatggcat tcttgtcccg attcctcagt accccttgta ctcggcttcc    540
atagctcttc atggcggagc tcttgtccca tactatctca atgaatcgac gggctggggt    600
ttggaaacct ctgatgttaa gaagcaactt gaagatgctc ggtcaagagg catcaacgtt    660
agggctttgg tggttatcaa tccaggaaat ccaactggac aggtacttgc tgaagaaaac    720
caatatgaca tagtgaagtt ctgcaaaaat gagggtcttg ttcttctagc tgatgaggta    780
taccaagaga acatctatgt tgacaacaag aaattccact ctttcaagaa gatagtgaga    840
tccttgggat acggcgagga ggatctccct ctagtatcat atcaatctgt ttctaaggga    900
tattatggtg agtgtggtaa aagaggtggt tactttgaga ttactggctt cagtgctcca    960
gtaagagagc agatctacaa aatagcatca gtgaacctat gctccaatat cactggccag   1020
atccttgcta gtcttgtcat gaacccacca aaggctagtg atgaatcata cgcttcatac   1080
aaggcagaaa aagatggaat cctcgcatct ttagctcgtc gtgcgaaggc attggagcat   1140
gcattcaata aacttgaggg aattacttgc aacgaggctg aaggagcaat gtacgtgttc   1200
cctcaaatct gtctgccaca gaaggcaatt gaggctgcta aagctgctaa caaagcacct   1260
gatgcattct atgctcttcg tctcctcgag tcgactggaa tcgtcgttgt ccctggatca   1320
ggatttggcc aggttcctgg cacatggcac ttcaggtgca cgatccttcc gcaggaggat   1380
aagatcccgg cagtcatctc ccgcttcacg gtgttccatg aggcgttcat gtcagagtat   1440
cgtgactaaa ctggt                                                   1455
```

<210> SEQ ID NO 2
<211> LENGTH: 482
<212> TYPE: PRT
<213> ORGANISM: Hordeum vulgare

<400> SEQUENCE: 2

```
Met Ala Ala Thr Val Ala Val Asp Asn Leu Asn Pro Lys Val Leu Lys
1               5                   10                  15

Cys Glu Tyr Ala Val Arg Gly Glu Ile Val Ile His Ala Gln Arg Leu
            20                  25                  30

Gln Glu Gln Leu Lys Thr Gln Pro Gly Ser Leu Pro Phe Asp Glu Ile
        35                  40                  45

Leu Tyr Cys Asn Ile Gly Asn Pro Gln Ser Leu Gly Gln Gln Pro Val
    50                  55                  60

Thr Phe Phe Arg Glu Val Leu Ala Leu Cys Asp His Pro Asp Leu Leu
65                  70                  75                  80

Gln Arg Glu Glu Ile Lys Thr Leu Phe Ser Ala Asp Ser Ile Ser Arg
                85                  90                  95

Ala Lys Gln Ile Leu Ala Met Ile Pro Gly Arg Ala Thr Gly Ala Tyr
            100                 105                 110

Ser His Ser Gln Gly Ile Lys Gly Leu Arg Asp Ala Ile Ala Ser Gly
        115                 120                 125

Ile Ala Ser Arg Asp Gly Phe Pro Ala Asn Ala Asp Asp Ile Phe Leu
    130                 135                 140

Thr Asp Gly Ala Ser Pro Gly Val His Leu Met Met Gln Leu Leu Ile
145                 150                 155                 160

Arg Asn Glu Lys Asp Gly Ile Leu Val Pro Ile Pro Gln Tyr Pro Leu
                165                 170                 175
```

Tyr Ser Ala Ser Ile Ala Leu His Gly Gly Ala Leu Val Pro Tyr Tyr
                180                 185                 190

Leu Asn Glu Ser Thr Gly Trp Gly Leu Glu Thr Ser Asp Val Lys Lys
            195                 200                 205

Gln Leu Glu Asp Ala Arg Ser Arg Gly Ile Asn Val Arg Ala Leu Val
210                 215                 220

Val Ile Asn Pro Gly Asn Pro Thr Gly Gln Val Leu Ala Glu Glu Asn
225                 230                 235                 240

Gln Tyr Asp Ile Val Lys Phe Cys Lys Asn Glu Gly Leu Val Leu Leu
                245                 250                 255

Ala Asp Glu Val Tyr Gln Glu Asn Ile Tyr Val Asp Asn Lys Lys Phe
            260                 265                 270

His Ser Phe Lys Lys Ile Val Arg Ser Leu Gly Tyr Gly Glu Glu Asp
        275                 280                 285

Leu Pro Leu Val Ser Tyr Gln Ser Val Ser Lys Gly Tyr Tyr Gly Glu
    290                 295                 300

Cys Gly Lys Arg Gly Gly Tyr Phe Glu Ile Thr Gly Phe Ser Ala Pro
305                 310                 315                 320

Val Arg Glu Gln Ile Tyr Lys Ile Ala Ser Val Asn Leu Cys Ser Asn
                325                 330                 335

Ile Thr Gly Gln Ile Leu Ala Ser Leu Val Met Asn Pro Pro Lys Ala
            340                 345                 350

Ser Asp Glu Ser Tyr Ala Ser Tyr Lys Ala Glu Lys Asp Gly Ile Leu
        355                 360                 365

Ala Ser Leu Ala Arg Arg Ala Lys Ala Leu Glu His Ala Phe Asn Lys
    370                 375                 380

Leu Glu Gly Ile Thr Cys Asn Glu Ala Glu Gly Ala Met Tyr Val Phe
385                 390                 395                 400

Pro Gln Ile Cys Leu Pro Gln Lys Ala Ile Glu Ala Ala Lys Ala Ala
                405                 410                 415

Asn Lys Ala Pro Asp Ala Phe Tyr Ala Leu Arg Leu Leu Glu Ser Thr
            420                 425                 430

Gly Ile Val Val Val Pro Gly Ser Gly Phe Gly Gln Val Pro Gly Thr
        435                 440                 445

Trp His Phe Arg Cys Thr Ile Leu Pro Gln Glu Asp Lys Ile Pro Ala
    450                 455                 460

Val Ile Ser Arg Phe Thr Val Phe His Glu Ala Phe Met Ser Glu Tyr
465                 470                 475                 480

Arg Asp

<210> SEQ ID NO 3
<211> LENGTH: 1490
<212> TYPE: DNA
<213> ORGANISM: Mus musculus

<400> SEQUENCE: 3
atggcctcac aaaggaatga ccggatccag gcttcaagga atggactgaa ggggaaggtg      60
ctaactctgg ataccatgaa cccatgtgtg cggagggtgg agtatgcagt ccgaggcccc     120
atcgtgcaac gtgccttgga gctggagcag agctgcgcc agggtgtgaa gaagcctttt      180
actgaggtta tccgtgccaa tattggggat gcacaagcca tggggcagag acccatcacc     240
ttcttccgcc aggtcctggc cctctgtgtc taccccaatc ttctgagcag tccggacttc     300
ccagaggatg ccaagagaag ggcagaacgc atcttgcagg catgcgggg ccacagcctg      360

```
ggtgcctata gcattagctc tggaatccag ccgattcggg aggatgtggc gcaatatatt    420
gagaggagag acggaggcat ccctgcagac ccgaacaaca tatttctgtc cacaggggcc    480
agcgatgcca tcgtgaccat gctcaagctg ctggtagccg gcgagggccg tgcgcgaacc    540
ggtgtactca ttcccattcc tcagtaccca ctgtactcag ctgcgctggc tgagctggac    600
gccgtgcaag tggactacta cctggacgaa gagcgcgcct gggctcttga catcgctgag    660
ctgcggcgcg ctctgtgcca ggcacgtgac cgctgctgcc ctcgagtact atgcgtcatc    720
aaccccggca accccacggg gcaggtgcag acccgtgaat gcatcgaggc cgtaatccgc    780
tttgctttcg aagagggact cttcctgatg gctgatgagg tataccaaga caatgtatat    840
gctgagggct ctcagttcca ttcattcaag aaggtgctca cggagatggg gccaccatat    900
gccacgcagc aggagctcgc gtcttttccac tcagtctcta agggctacat gggcgagtgc    960
gggtttcgtg gtggctatgt ggaagtggta acatggatgc cgaggtgcag aaacagatg     1020 gcgaaactga tgagcgtgcg gttgtgtcca ccagtgccgg ccaggctttt gatgggcatg    1080
gtggtcagtc cgccaacccc ctcggagccg tccttcaagc agtttcaagc agagaggcag    1140
gaggtgctgg ctgaactggc agccaaggct aaactcacgg agcaggtctt caacgaggcc    1200
cccgggatcc gctgcaaccc ggtgcagggc gctatgtatt ccttccctca aattcagctg    1260
cctttgaaag cagtgcagcg tgcgcaggac ctgggcctgg cccctgacat gttcttctgt    1320
ctgtgcctcc tggaagagac cggcatctgc gttgtgcctg ggagtggctt tgggcagcag    1380
gagggcacct atcatttccg gatgaccatt ctgcccccca tggagaaact gcgggtgctg    1440
ctggagaaac tgaggcactt ccatgctaaa ttcactcatg agtactcctt               1490

<210> SEQ ID NO 4
<211> LENGTH: 1199
<212> TYPE: DNA
<213> ORGANISM: Pyrococcus furiosus

<400> SEQUENCE: 4
atgataaggg cctcaaagag agctctctct gtggagtatg ctattagaga tgtcgttcta     60
cctgcaaggg aacttgaaaa aaagggaatc aaggtaatta ggctaaacat aggcgatcct    120
gtaaagttcg actttcaacc acccgagcac atgaaggaag catattgtaa agcaattaaa    180
gaggggcaca attactatgg agatagtgag ggattacccg agttaagaaa agctatagta    240
gaaagggaaa agaggaagaa tggagtggac ataactcccg atgacgtgag ggttacagct    300
gcagtcactg aagctctcca gctaattttt ggagctctat tagacccagg agatgaaatt    360
ctagttcctg ggcccagtta tcctccctat acagggcttg taaagttcta cggtggaaag    420
cctgtggaat atagaactat tgaagaggaa gactggcaac ctgatattga cgacattagg    480
aagaagataa cagacagaac aaaagctata gcagttataa accccaacaa cccgactgga    540
gcgctctacg acaaaaagac acttgaggaa atcttgaaca tcgcagggga atatgaaatt    600
cctgttataa gcgacgagat atacgatttg atgacatacg agggagaaca catttctccc    660
ggatcattaa ccaaagatgt tcctgtaata gttatgaacg gattatccaa agtctacttt    720
gccacagggt ggagacttgg atacatgtac tttgtcgatc cagagaataa attgagtgag    780
gtcagagagg caatagatag attggcaagg attagactgt gtccaaatac ccccgcacaa    840
ttcgcagcta tagcaggact aacgggccca atgattatc tcaaagaata catgaaaaag    900
ctcaaggaga gaagagatta catctacaag aggctaaatg agatcccagg aataagcacg    960
```

```
acaaaaccac aaggagcatt ttacatattc cccaagatag aggtgggacc gtggaagaat    1020
gataaagaat tcgttcttga cgttctccac aatgctcacg ttctatttgt tcacggttca    1080
ggatttggag agtatggtgc aggccacttt agagcagtgt tcttgcctcc aatagaaatc    1140
ctggaagagg ctatggatag attcgaaaag ttcatgaaag aaagactgaa agaatgatt     1199

<210> SEQ ID NO 5
<211> LENGTH: 742
<212> TYPE: DNA
<213> ORGANISM: Artificial Sequence
<220> FEATURE:
<223> OTHER INFORMATION: PBpr1 promoter sequence

<400> SEQUENCE: 5
gaattctgaa agtttccgtc caaatcgcac cttttaaccg tttgaaaaac atacaaacga      60
aaaataatct atatcttaat caggaagaaa gagtacgaaa tggtgaaccg tcgaaactat     120
tcatatacgt cgtctgtctc atgaaaaaaa aaatcaatcc agaaggatac gagacacttt     180
tacttcaaca aatatagaca tgagcttatt ctactaggtt tggttgttta ataagacgaa     240
agaaatacat tggttagttt ttcattaaaa aataatcgtt tgactgacat aaacctagga     300
aatactggat taagatagat cagtaggatt aagatccact gatgtaattt cccactgatt     360
tggtggctga catgtggacc tgagagttgt gtgggctcac atgtcaaatc acggtgaaca     420
gtacgtcacg atatgttaga ggttcctctt ccggagatac ttatacgaat tttgcgaaa     480 cctgcaaact tgatggacg attgaggcga gtttagttct aaattttttc ttcaaacttc     540
taactttttc atcacatcgt ttcaatttca atcaaacttc caatgttgac gtgaactaaa     600
cacacctatg agatatgaga agcgggttga cacttgacaa gtcctgacat gctgtgttgg     660
cgtgggcccc acctgccacg tcaggtccag ctccgggtgg ttgggtttgg tgctttccga     720
taggcacgag ctcggtacca tg                                             742

<210> SEQ ID NO 6
<211> LENGTH: 1507
<212> TYPE: DNA
<213> ORGANISM: Artificial Sequence
<220> FEATURE:
<223> OTHER INFORMATION: Maize Ubiquitin 1 plus 1st Intron promoter

<400> SEQUENCE: 6
ctgcagtgca gcgtgacccg gtcgtgcccc tctctagaga taatgagcat tgcatgtcta      60
agttataaaa aattaccaca tattttttt gtcacacttg tttgaagtgc agtttatcta     120
tctttataca tatatttaaa ctttactcta cgaataatat aatctatagt actacaataa     180
tatcagtgtt ttagagaatc atataaatga acagttagac atggtctaaa ggacaattga     240 gtatttgac aacaggactc tacagtttta tctttttagt gtgcatgtgt tctccttttt     300
ttttgcaaat agcttcacct atataatact tcatccattt tattagtaca tccatttagg     360
gtttagggtt aatggttttt atagactaat ttttttagta catctatttt attctatttt     420
agcctctaaa ttaagaaaac taaaactcta tttagttttt ttatttaat aatttagata     480 taaaatagaa taaaataaag tgactaaaaa ttaaacaaat acccttaag aaattaaaaa     540 aactaaggaa acatttttct tgtttcgagt agataatgcc agcctgttaa acgccgtcga     600
tcgacgagtc taacggacac caaccagcga accagcagcg tcgcgtcggg ccaagcgaag     660
cagacggcac ggcatctctg tcgctgcctc tggaccctc tcgagagttc cgctccaccg     720
ttggacttgc tccgctgtcg gcatccagaa attgcgtggc ggagcggcag acgtgagccg     780
```

```
gcacggcagg cggcctcctc ctcctctcac ggcaccggca gctacggggg attcctttcc    840
caccgctcct tcgctttccc ttcctcgccc gccgtaataa atagacaccc cctccacacc    900
ctctttcccc aacctcgtgt tgttcggagc gcacacacac acaaccagat ctcccccaaa    960
tccacccgtc ggcacctccg cttcaaggta cgccgctcgt cctcccccccc cccccctctc   1020 taccttctct agatcggcgt tccggtccat ggttagggcc cggtagttct acttctgttc   1080
atgtttgtgt tagatccgtg tttgtgttag atccgtgctg ctagcgttcg tacacggatg   1140
cgacctgtac gtcagacacg ttctgattgc taacttgcca gtgtttctct ttggggaatc   1200
ctgggatggc tctagccgtt ccgcagacgg gatcgatcta ggataggtat acatgttgat   1260
gtgggtttta ctgatgcata tacatgatgg catatgcagc atctattcat atgctctaac   1320
cttgagtacc tatctattat aataaacaag tatgttttat aattattttg atcttgatat   1380
acttggatga tggcatatgc agcagctata tgtggatttt tttagccctg ccttcatacg   1440
ctatttattt gcttggtact gtttcttttg tcgatgctca ccctgttgtt tggtgttact   1500
tctgcag                                                             1507
```

<210> SEQ ID NO 7
<211> LENGTH: 507
<212> TYPE: PRT
<213> ORGANISM: Saccharomyces cerevisiae

<400> SEQUENCE: 7

```
Met Thr Met Thr His Gln Gln Asp Leu Lys Gly Val Phe Thr Ala Lys
1               5                   10                  15

Asp Leu Asp Phe Lys Pro Ala Gly Lys Ile Thr Lys Lys Asp Leu Asn
                20                  25                  30

Thr Gly Val Thr Lys Ala Glu Tyr Ala Val Arg Gly Ala Ile Pro Thr
            35                  40                  45

Arg Ala Asp Glu Leu Lys Glu Glu Leu Lys Lys Asn Pro Glu Val Leu
        50                  55                  60

Pro Phe Asp Asp Ile Ile Asn Ala Asn Ile Gly Asn Pro Gln Gln Leu
65                  70                  75                  80

Asp Gln Lys Pro Leu Thr Phe Thr Arg Gln Val Leu Ala Ile Leu Glu
                85                  90                  95

Tyr Pro Glu Ile Leu Arg Val Gly His Asn Glu Leu Ala Ser Leu Asn
            100                 105                 110

Leu Phe Ser Arg Asp Ala Leu Glu Arg Ala Glu Arg Leu Leu Asn Asp
        115                 120                 125

Ile Gly Gly Ser Ile Gly Ala Tyr Ser His Ser Gln Gly Val Pro Gly
    130                 135                 140

Ile Arg Gln Thr Val Ala Asp Phe Ile Thr Arg Arg Asp Gly Gly Glu
145                 150                 155                 160

Pro Ala Thr Pro Glu Asp Ile Tyr Leu Thr Thr Gly Ala Ser Ser Ala
                165                 170                 175

Ala Thr Ser Leu Leu Ser Leu Leu Cys Lys Asp Ser Gln Thr Gly Leu
            180                 185                 190

Leu Ile Pro Ile Pro Gln Tyr Pro Leu Tyr Thr Ala Ser Ala Ser Leu
        195                 200                 205

Phe Asn Ala Gln Val Leu Pro Tyr Tyr Leu Asp Glu Glu Ser Asn Trp
    210                 215                 220

Ser Thr Asn Ser Asp Glu Ile Glu Lys Val Val Gln Asp Ala Leu Lys
225                 230                 235                 240
```

```
Lys Gln Ile Arg Pro Ser Val Leu Ile Val Ile Asn Pro Gly Asn Pro
                245                 250                 255

Thr Gly Ala Val Leu Ser Glu Glu Thr Ile Ser Arg Ile Cys Leu Ile
            260                 265                 270

Ala Ala Lys Tyr Gly Ile Thr Ile Ile Ser Asp Glu Val Tyr Gln Glu
            275                 280                 285

Asn Val Phe Asn Asp Val Lys Phe His Ser Met Lys Lys Val Leu Arg
        290                 295                 300

Lys Leu Gln His Leu Tyr Pro Gly Lys Phe Asp Asn Val Gln Leu Ala
305                 310                 315                 320

Ser Leu His Ser Ile Ser Lys Gly Phe Met Gly Glu Cys Gly Gln Arg
                325                 330                 335

Gly Gly Tyr Met Glu Ile Ile Gly Phe Ser Gln Glu Ile Arg Asp Ala
            340                 345                 350

Leu Phe Lys Leu Met Ser Ile Ser Ile Cys Ser Val Val Thr Gly Gln
        355                 360                 365

Ala Val Val Asp Leu Met Val Lys Pro Pro Gln Pro Gly Asp Glu Ser
        370                 375                 380

Tyr Glu Gln Asp His Asp Glu Arg Leu Lys Ile Phe His Glu Met Arg
385                 390                 395                 400

Thr Arg Ala Asn Leu Leu Tyr Glu Thr Phe Lys Glu Leu Glu Gly Ile
                405                 410                 415

Glu Cys Gln Lys Pro Gln Gly Ala Met Tyr Leu Phe Pro Arg Leu Val
            420                 425                 430

Leu Pro Lys Lys Ala Leu Cys Glu Ser Glu Arg Leu Gly Ile Glu Pro
        435                 440                 445

Asp Glu Phe Tyr Cys Thr Ser Leu Leu Glu Ser Thr Gly Ile Cys Thr
        450                 455                 460

Val Pro Gly Ser Gly Phe Gly Gln Arg Pro Gly Thr Tyr His Val Arg
465                 470                 475                 480

Thr Thr Phe Leu Ala Pro Gly Thr Lys Trp Ile Gln Asp Trp Lys Glu
                485                 490                 495

Phe His Gln Asp Phe Phe Ser Lys Tyr Arg Asn
            500                 505

<210> SEQ ID NO 8
<211> LENGTH: 592
<212> TYPE: PRT
<213> ORGANISM: Saccharomyces cerevisiae

<400> SEQUENCE: 8

Met Leu Ser Leu Ser Ala Lys Asn His Phe Thr Val Ser Asn Ser Ile
1               5                   10                  15

Thr His Val Ile Lys Ser Tyr His Ile Arg Thr Leu Thr Ser Ser Ala
            20                  25                  30

Glu Lys Met Pro His Ile Thr Thr Pro Phe Ser Thr Ser Ala Ser Ser
        35                  40                  45

Thr Lys Leu Lys Ala Phe Arg Lys Val Arg Pro Val Leu Gln Arg His
    50                  55                  60

Ser Ser Ser Trp Ile Val Ala Gln Asn His Arg Ser Leu Ser Gly
65                  70                  75                  80

Gln Ser Ser Leu Asn Asp Leu Arg His Leu Asn Arg Phe Pro His His
                85                  90                  95

Thr Leu Lys Thr Ser Asn Asn Glu Phe Tyr Pro Ala Glu Gln Leu Thr
```

```
            100             105               110
Leu Glu Asp Val Asn Glu Asn Val Leu Lys Ala Lys Tyr Ala Val Arg
            115             120             125
Gly Ala Ile Pro Met Arg Ala Glu Glu Leu Lys Ala Gln Leu Glu Lys
            130             135             140
Asp Pro Gln Ser Leu Pro Phe Asp Arg Ile Ile Asn Ala Asn Ile Gly
145             150             155             160
Asn Pro Gln Gln Leu Gln Gln Lys Pro Leu Thr Tyr Tyr Arg Gln Val
            165             170             175
Leu Ser Leu Leu Gln Tyr Pro Glu Leu Leu Asn Gln Asn Glu Gln Gln
            180             185             190
Leu Val Asp Ser Lys Leu Phe Lys Leu Asp Ala Ile Lys Arg Ala Lys
            195             200             205
Ser Leu Met Glu Asp Ile Gly Gly Ser Val Gly Ala Tyr Ser Ser Ser
            210             215             220
Gln Gly Val Glu Gly Ile Arg Lys Ser Val Ala Glu Phe Ile Thr Lys
225             230             235             240
Arg Asp Glu Gly Glu Ile Ser Tyr Pro Glu Asp Ile Phe Leu Thr Ala
            245             250             255
Gly Ala Ser Ala Ala Val Asn Tyr Leu Leu Ser Ile Phe Cys Arg Gly
            260             265             270
Pro Glu Thr Gly Val Leu Ile Pro Ile Pro Gln Tyr Pro Leu Tyr Thr
            275             280             285
Ala Thr Leu Ala Leu Asn Asn Ser Gln Ala Leu Pro Tyr Tyr Leu Asp
            290             295             300
Glu Asn Ser Gly Trp Ser Thr Asn Pro Glu Glu Ile Glu Thr Val Val
305             310             315             320
Lys Glu Ala Ile Gln Asn Glu Ile Lys Pro Thr Val Leu Val Val Ile
            325             330             335
Asn Pro Gly Asn Pro Thr Gly Ala Val Leu Ser Pro Glu Ser Ile Ala
            340             345             350
Gln Ile Phe Glu Val Ala Ala Lys Tyr Gly Thr Val Val Ile Ala Asp
            355             360             365
Glu Val Tyr Gln Glu Asn Ile Phe Pro Gly Thr Lys Phe His Ser Met
            370             375             380
Lys Lys Ile Leu Arg His Leu Gln Arg Glu His Pro Gly Lys Phe Asp
385             390             395             400
Asn Val Gln Leu Ala Ser Leu His Ser Thr Ser Lys Gly Val Ser Gly
            405             410             415
Glu Cys Gly Gln Arg Gly Gly Tyr Met Glu Leu Thr Gly Phe Ser His
            420             425             430
Glu Met Arg Gln Val Ile Leu Lys Leu Ala Ser Ile Ser Leu Cys Pro
            435             440             445
Val Val Thr Gly Gln Ala Leu Val Asp Leu Met Val Arg Pro Pro Val
            450             455             460
Glu Gly Glu Glu Ser Phe Glu Ser Asp Gln Ala Glu Arg Asn Ser Ile
465             470             475             480
His Glu Lys Leu Ile Thr Arg Ala Met Thr Leu Tyr Glu Thr Phe Asn
            485             490             495
Ser Leu Glu Gly Ile Glu Cys Gln Lys Pro Gln Gly Ala Met Tyr Leu
            500             505             510
Phe Pro Lys Ile Asp Leu Pro Phe Lys Ala Val Gln Glu Ala Arg His
            515             520             525
```

```
Leu Glu Leu Thr Pro Asp Glu Phe Tyr Cys Lys Lys Leu Glu Ser
            530                 535                 540

Thr Gly Ile Cys Thr Val Pro Gly Ser Gly Phe Gly Gln Glu Pro Gly
545                 550                 555                 560

Thr Tyr His Leu Arg Thr Thr Phe Leu Ala Pro Gly Leu Glu Trp Ile
            565                 570                 575

Lys Lys Trp Glu Ser Phe His Lys Glu Phe Asp Gln Tyr Arg Asp
            580                 585                 590

<210> SEQ ID NO 9
<211> LENGTH: 543
<212> TYPE: PRT
<213> ORGANISM: Arabidopsis thaliana

<400> SEQUENCE: 9

Met Arg Arg Phe Val Ile Gly Gln Ala Lys Asn Leu Ile Asp Gln Ser
1               5                   10                  15

Arg Arg Arg Gln Leu His His His Lys Asn Leu Ser Phe Val Ser Leu
            20                  25                  30

Ile Pro Pro Phe Ser Ala Pro Ser Asp Ser Ser Arg His Leu Ser
        35                  40                  45

Ser Ser Ser Ser Asp Met Ser Ala Ser Ser Ser Ser Ser Leu
    50                  55                  60

Pro Val Thr Leu Asp Thr Ile Asn Pro Lys Val Ile Lys Cys Glu Tyr
65                  70                  75                  80

Ala Val Arg Gly Glu Ile Val Asn Ile Ala Gln Lys Leu Gln Glu Asp
                85                  90                  95

Leu Lys Thr Asn Lys Asp Ala Tyr Pro Phe Asp Glu Ile Ile Tyr Cys
            100                 105                 110

Asn Ile Gly Asn Pro Gln Ser Leu Gly Gln Gln Pro Ile Thr Phe Phe
        115                 120                 125

Arg Glu Val Leu Ala Leu Cys Ser Tyr Thr Ala Leu Leu Asp Glu Ser
    130                 135                 140

Ala Thr His Gly Leu Phe Ser Ser Asp Ser Ile Glu Arg Ala Trp Lys
145                 150                 155                 160

Ile Leu Asp Gln Ile Pro Gly Arg Ala Thr Gly Ala Tyr Ser His Ser
                165                 170                 175

Gln Gly Ile Lys Gly Leu Arg Asp Ala Ile Ala Asp Gly Ile Glu Ala
            180                 185                 190

Arg Asp Gly Phe Pro Ala Asp Pro Asn Asp Ile Phe Met Thr Asp Gly
        195                 200                 205

Ala Ser Pro Gly Val His Met Met Met Gln Leu Leu Ile Thr Ser Glu
    210                 215                 220

Lys Asp Gly Ile Leu Cys Pro Ile Pro Gln Tyr Pro Leu Tyr Ser Ala
225                 230                 235                 240

Ser Ile Ala Leu His Gly Gly Thr Leu Val Pro Tyr Tyr Leu Asp Glu
                245                 250                 255

Ala Ser Gly Trp Gly Leu Glu Ile Ser Glu Leu Lys Lys Gln Leu Glu
            260                 265                 270

Asp Ala Arg Ser Lys Gly Ile Thr Val Arg Ala Leu Val Ile Asn
        275                 280                 285

Pro Gly Asn Pro Thr Gly Gln Val Leu Ser Glu Glu Asn Gln Arg Asp
    290                 295                 300

Val Val Lys Phe Cys Lys Gln Glu Gly Leu Val Leu Leu Ala Asp Glu
```

```
            305                 310                 315                 320
    Val Tyr Gln Glu Asn Val Tyr Val Pro Asp Lys Lys Phe His Ser Phe
                    325                 330                 335

Lys Lys Val Ala Arg Ser Met Gly Tyr Gly Lys Asp Leu Ala Leu
                340                 345                 350

Val Ser Phe Gln Ser Val Ser Lys Gly Tyr Gly Glu Cys Gly Lys
                355                 360                 365

Arg Gly Gly Tyr Met Glu Val Thr Gly Phe Thr Ser Asp Val Arg Glu
        370                 375                 380

Gln Ile Tyr Lys Met Ala Ser Val Asn Leu Cys Ser Asn Ile Ser Gly
    385                 390                 395                 400

Gln Ile Leu Ala Ser Leu Ile Met Ser Pro Lys Pro Gly Asp Asp
                405                 410                 415

Ser Tyr Glu Ser Tyr Ile Ala Glu Lys Asp Gly Ile Leu Ser Ser Leu
                420                 425                 430

Ala Arg Arg Ala Lys Thr Leu Glu Glu Ala Leu Asn Lys Leu Glu Gly
        435                 440                 445

Val Thr Cys Asn Arg Ala Glu Gly Ala Met Tyr Leu Phe Pro Cys Leu
    450                 455                 460

His Leu Pro Gln Lys Ala Ile Ala Ala Ala Glu Ala Lys Thr Ala
    465                 470                 475                 480

Pro Asp Asn Phe Tyr Cys Lys Arg Leu Leu Lys Ala Thr Gly Ile Val
                485                 490                 495

Val Val Pro Gly Ser Gly Phe Arg Gln Val Pro Gly Thr Trp His Phe
                500                 505                 510

Arg Cys Thr Ile Leu Pro Gln Glu Asp Lys Ile Pro Ala Ile Val Asp
        515                 520                 525

Arg Leu Thr Ala Phe His Gln Ser Phe Met Asp Glu Phe Arg Asp
        530                 535                 540

<210> SEQ ID NO 10
<211> LENGTH: 540
<212> TYPE: PRT
<213> ORGANISM: Arabidopsis thaliana

<400> SEQUENCE: 10

Met Arg Arg Phe Leu Ile Asn Gln Ala Lys Gly Leu Val Asp His Ser
1               5                   10                  15

Arg Arg Gln His His His Lys Ser Pro Ser Phe Leu Ser Pro Gln Pro
                20                  25                  30

Arg Pro Leu Ala Ser Ser Pro Ala Leu Ser Arg Phe Phe Ser Ser
            35                  40                  45

Thr Ser Glu Met Ser Ala Ser Asp Ser Thr Ser Ser Leu Pro Val Thr
    50                  55                  60

Leu Asp Ser Ile Asn Pro Lys Val Leu Lys Cys Glu Tyr Ala Val Arg
65                  70                  75                  80

Gly Glu Ile Val Asn Ile Ala Gln Lys Leu Gln Asp Leu Lys Thr
                85                  90                  95

Asn Lys Asp Ala Tyr Pro Phe Asp Glu Ile Ile Tyr Cys Asn Ile Gly
            100                 105                 110

Asn Pro Gln Ser Leu Gly Gln Leu Pro Ile Lys Phe Phe Arg Glu Val
        115                 120                 125

Leu Ala Leu Cys Asp His Ala Ser Leu Leu Asp Glu Ser Glu Thr His
    130                 135                 140
```

```
Gly Leu Phe Ser Thr Asp Ser Ile Asp Arg Ala Trp Arg Ile Leu Asp
145                 150                 155                 160

His Ile Pro Gly Arg Ala Thr Gly Ala Tyr Ser His Ser Gln Gly Ile
            165                 170                 175

Lys Gly Leu Arg Asp Val Ile Ala Ala Gly Ile Glu Ala Arg Asp Gly
        180                 185                 190

Phe Pro Ala Asp Pro Asn Asp Ile Phe Leu Thr Asp Gly Ala Ser Pro
    195                 200                 205

Ala Val His Met Met Met Gln Leu Leu Leu Ser Ser Glu Lys Asp Gly
210                 215                 220

Ile Leu Ser Pro Ile Pro Gln Tyr Pro Leu Tyr Ser Ala Ser Ile Ala
225                 230                 235                 240

Leu His Gly Gly Ser Leu Val Pro Tyr Tyr Leu Asp Glu Ala Thr Gly
                245                 250                 255

Trp Gly Leu Glu Ile Ser Asp Leu Lys Lys Gln Leu Glu Glu Ala Arg
            260                 265                 270

Ser Lys Gly Ile Ser Val Arg Ala Leu Val Ile Asn Pro Gly Asn
        275                 280                 285

Pro Thr Gly Gln Val Leu Ala Glu Glu Asn Gln Arg Asp Ile Val Asn
290                 295                 300

Phe Cys Lys Gln Glu Gly Leu Val Leu Leu Ala Asp Glu Val Tyr Gln
305                 310                 315                 320

Glu Asn Val Tyr Val Pro Asp Lys Lys Phe His Ser Phe Lys Lys Val
                325                 330                 335

Ala Arg Ser Leu Gly Tyr Gly Glu Lys Asp Ile Ser Leu Val Ser Phe
        340                 345                 350

Gln Ser Val Ser Lys Gly Tyr Tyr Gly Glu Cys Gly Lys Arg Gly Gly
    355                 360                 365

Tyr Met Glu Val Thr Gly Phe Thr Ser Asp Val Arg Glu Gln Ile Tyr
370                 375                 380

Lys Met Ala Ser Val Asn Leu Cys Ser Asn Ile Ser Gln Ile Leu
385                 390                 395                 400

Ala Ser Leu Val Met Ser Pro Lys Pro Gly Asp Asp Ser Tyr Asp
            405                 410                 415

Ser Tyr Met Ala Glu Arg Asp Gly Ile Leu Ser Ser Met Ala Lys Arg
        420                 425                 430

Ala Lys Thr Leu Glu Asp Ala Leu Asn Ser Leu Glu Gly Val Thr Cys
    435                 440                 445

Asn Arg Ala Glu Gly Ala Met Tyr Leu Phe Pro Arg Ile Asn Leu Pro
450                 455                 460

Gln Lys Ala Ile Glu Ala Ala Glu Ala Glu Lys Thr Ala Pro Asp Ala
465                 470                 475                 480

Phe Tyr Cys Lys Arg Leu Leu Asn Ala Thr Gly Val Val Val Pro
            485                 490                 495

Gly Ser Gly Phe Gly Gln Val Pro Gly Thr Trp His Phe Arg Cys Thr
        500                 505                 510

Ile Leu Pro Gln Glu Asp Lys Ile Pro Ala Ile Val Asn Arg Leu Thr
    515                 520                 525

Glu Phe His Lys Ser Phe Met Asp Glu Phe Arg Asn
530                 535                 540

<210> SEQ ID NO 11
<211> LENGTH: 524
<212> TYPE: PRT
```

<213> ORGANISM: Medicago truncatula

<400> SEQUENCE: 11

```
Met Arg Lys Ser Ala Ala Asp Arg Phe Arg His Leu Phe Asn Arg Ser
1               5                   10                  15

Leu Val Phe Val Arg Asn Gln Asn Gln Gln Tyr His His Pro Ser Pro
            20                  25                  30

Leu Arg Ser Leu Ser Ser Met Ala Ser Asp Ser Pro Phe Pro Val Thr
        35                  40                  45

Ala Gln Asn Ile Asn Pro Gln Val Leu Lys Cys Gln Tyr Ala Val Arg
50                  55                  60

Gly Glu Ile Val Thr Leu Ala Gln Asn Leu Gln Lys Ala Leu Gln Ala
65                  70                  75                  80

Asn Pro Asp Ala His Ser Phe Asp Glu Ile Ile Tyr Cys Asn Ile Gly
                85                  90                  95

Asn Pro Gln Ser Leu Gly Gln Gln Pro Ile Thr Phe Phe Arg Glu Val
            100                 105                 110

Leu Ala Leu Cys Asp Tyr Pro Ala Leu Leu Asp Lys Ser Glu Thr Gln
        115                 120                 125

Gly Leu Phe Ser Ala Asp Ser Ile Glu Arg Ala Trp Gln Ile Val Asp
130                 135                 140

Gln Ile Pro Gly Arg Ala Thr Gly Ala Tyr Ser His Ser Gln Gly Ile
145                 150                 155                 160

Gln Gly Leu Arg Asp Thr Ile Ala Ala Gly Ile Glu Glu Arg Asp Gly
                165                 170                 175

Phe Pro Cys Asn Ala Asn Asp Ile Phe Leu Thr Asp Gly Ala Ser Pro
            180                 185                 190

Ala Val His Met Met Met Gln Leu Leu Ile Arg Ser Glu Lys Asp Gly
        195                 200                 205

Ile Leu Cys Pro Ile Pro Gln Tyr Pro Leu Tyr Ser Ala Ser Ile Thr
210                 215                 220

Leu His Gly Gly His Leu Val Pro Tyr Tyr Leu Asp Glu Ala Thr Gly
225                 230                 235                 240

Trp Gly Leu Glu Ile Ser Glu Leu Lys Lys Gln Leu Glu Asp Ala Lys
                245                 250                 255

Ser Lys Gly Ile Ser Val Arg Ala Leu Ala Val Ile Asn Pro Gly Asn
            260                 265                 270

Pro Thr Gly Gln Val Leu Ala Glu Asp Asn Gln Arg Ala Ile Val Glu
        275                 280                 285

Phe Cys Lys Gln Glu Gly Leu Val Leu Leu Ala Asp Glu Val Tyr Gln
290                 295                 300

Glu Asn Val Tyr Val Pro Glu Lys Lys Phe His Ser Phe Lys Lys Val
305                 310                 315                 320

Ser Arg Ser Met Gly Tyr Gly Asp Asn Asp Ile Cys Leu Val Ser Phe
                325                 330                 335

Gln Ser Val Ser Lys Gly Tyr His Gly Glu Cys Gly Lys Arg Gly Gly
            340                 345                 350

Tyr Met Glu Val Thr Gly Phe Ser Pro Asp Val Arg Glu Gln Ile Tyr
        355                 360                 365

Lys Val Ala Ser Val Asn Leu Cys Ser Asn Ile Thr Gly Gln Ile Leu
370                 375                 380

Ala Ser Leu Ile Met Ser Pro Pro Lys Val Gly Asp Glu Ser Tyr Glu
385                 390                 395                 400
```

```
Ser Phe Met Ala Glu Arg Gly Ala Ile Leu Ser Ser Leu Thr Thr Arg
                405                 410                 415

Ala Lys Ala Leu Glu Glu Ala Leu Asn Lys Leu Glu Gly Val Thr Cys
            420                 425                 430

Asn Lys Ala Glu Gly Ala Met Tyr Leu Phe Pro Arg Ile Arg Leu Pro
        435                 440                 445

Glu Lys Ala Ile Lys Ala Ala Glu Ala Glu Lys Ser Ala Pro Asp Ala
    450                 455                 460

Phe Tyr Cys Lys Arg Leu Leu Asn Ala Thr Gly Ile Val Val Val Pro
465                 470                 475                 480

Gly Ser Gly Phe Gly Gln Val Pro Gly Thr Trp His Phe Arg Cys Thr
                485                 490                 495

Ile Leu Pro Gln Glu Asp Arg Ile Pro Ala Ile Val Thr Arg Leu Thr
            500                 505                 510

Glu Phe His Gln Lys Phe Met Asp Glu Phe Arg Asp
        515                 520

<210> SEQ ID NO 12
<211> LENGTH: 481
<212> TYPE: PRT
<213> ORGANISM: Arabidopsis thaliana

<400> SEQUENCE: 12

Met Ala Leu Lys Ala Leu Asp Tyr Asp Thr Leu Asn Glu Asn Val Lys
1               5                   10                  15

Lys Cys Gln Tyr Ala Val Arg Gly Glu Leu Tyr Leu Arg Ala Ser Glu
                20                  25                  30

Leu Gln Lys Glu Gly Lys Lys Ile Ile Phe Thr Asn Val Gly Asn Pro
            35                  40                  45

His Ala Leu Gly Gln Lys Pro Leu Thr Phe Pro Arg Gln Val Val Ala
        50                  55                  60

Leu Cys Gln Ala Pro Phe Leu Leu Asp Asp Pro Asn Val Gly Met Leu
65                  70                  75                  80

Phe Pro Ala Asp Ala Ile Ala Arg Ala Lys His Tyr Leu Ser Leu Thr
                85                  90                  95

Ser Gly Gly Leu Gly Ala Tyr Ser Asp Ser Arg Gly Leu Pro Gly Val
                100                 105                 110

Arg Lys Glu Val Ala Glu Phe Ile Gln Arg Arg Asp Gly Tyr Pro Ser
            115                 120                 125

Asp Pro Glu Leu Ile Phe Leu Thr Asp Gly Ala Ser Lys Gly Val Met
        130                 135                 140

Gln Ile Leu Asn Cys Val Ile Arg Gly Asn Gly Asp Gly Ile Leu Val
145                 150                 155                 160

Pro Val Pro Gln Tyr Pro Leu Tyr Ser Ala Thr Ile Ser Leu Leu Gly
                165                 170                 175

Gly Thr Leu Val Pro Tyr Tyr Leu Asp Glu Ser Glu Asn Trp Gly Leu
                180                 185                 190

Asp Val Ala Asn Leu Arg Gln Ser Val Ala Gln Ala Arg Ser Gln Gly
            195                 200                 205

Ile Thr Val Arg Ala Met Val Ile Ile Asn Pro Gly Asn Pro Thr Gly
        210                 215                 220

Gln Cys Leu Ser Glu Ala Asn Ile Arg Glu Ile Leu Lys Phe Cys Tyr
225                 230                 235                 240

Asn Glu Lys Leu Val Leu Leu Gly Asp Glu Val Tyr Gln Gln Asn Ile
                245                 250                 255
```

Tyr Gln Asp Glu Arg Pro Phe Ile Ser Ser Lys Lys Val Leu Met Glu
            260                 265                 270

Met Gly Ser Pro Phe Ser Lys Glu Val Gln Leu Val Ser Phe His Thr
        275                 280                 285

Val Ser Lys Gly Tyr Trp Gly Glu Cys Gly Gln Arg Gly Gly Tyr Phe
    290                 295                 300

Glu Met Thr Asn Leu Pro Pro Arg Val Glu Glu Ile Tyr Lys Val
305                 310                 315                 320

Ala Ser Ile Ala Leu Ser Pro Asn Val Ser Ala Gln Ile Phe Met Gly
                325                 330                 335

Leu Met Val Asn Pro Pro Lys Pro Gly Asp Ile Ser Tyr Asp Gln Phe
            340                 345                 350

Ala Arg Glu Ser Lys Gly Ile Leu Glu Ser Leu Arg Arg Ala Arg
        355                 360                 365

Leu Met Thr Asp Gly Phe Asn Ser Cys Lys Asn Val Val Cys Asn Phe
    370                 375                 380

Thr Glu Gly Ala Met Tyr Ser Phe Pro Gln Ile Arg Leu Pro Thr Gly
385                 390                 395                 400

Ala Leu Gln Ala Ala Lys Gln Ala Gly Lys Val Pro Asp Val Phe Tyr
                405                 410                 415

Cys Leu Lys Leu Leu Glu Ala Thr Gly Ile Ser Thr Val Pro Gly Ser
            420                 425                 430

Gly Phe Gly Gln Lys Glu Gly Val Phe His Leu Arg Thr Thr Ile Leu
        435                 440                 445

Pro Ala Glu Asp Glu Met Pro Glu Ile Met Asp Ser Phe Lys Lys Phe
    450                 455                 460

Asn Asp Glu Phe Met Thr Gln Tyr Asp Asn Asn Phe Gly Tyr Ser Lys
465                 470                 475                 480

Met

<210> SEQ ID NO 13
<211> LENGTH: 481
<212> TYPE: PRT
<213> ORGANISM: Arabidopsis thaliana

<400> SEQUENCE: 13

Met Ser Leu Lys Ala Leu Asp Tyr Glu Ser Leu Asn Glu Asn Val Lys
1               5                   10                  15

Asn Cys Gln Tyr Ala Val Arg Gly Glu Leu Tyr Leu Arg Ala Ser Glu
            20                  25                  30

Leu Gln Lys Glu Gly Lys Lys Ile Ile Phe Thr Asn Val Gly Asn Pro
        35                  40                  45

His Ala Leu Gly Gln Lys Pro Leu Thr Phe Pro Arg Gln Val Val Ser
    50                  55                  60

Leu Cys Gln Ala Pro Phe Leu Leu Asp Asp Pro Asn Val Gly Met Ile
65                  70                  75                  80

Phe Pro Ala Asp Ala Ile Ala Arg Ala Lys His Tyr Leu Ser Leu Thr
                85                  90                  95

Ser Gly Gly Leu Gly Ala Tyr Ser Asp Ser Arg Gly Leu Pro Gly Val
            100                 105                 110

Arg Lys Glu Val Ala Glu Phe Ile Glu Arg Arg Asp Gly Tyr Pro Ser
        115                 120                 125

Asp Pro Glu Leu Ile Phe Leu Thr Asp Gly Ala Ser Lys Gly Val Met
    130                 135                 140

```
Gln Ile Leu Asn Cys Val Ile Arg Gly Gln Lys Asp Gly Ile Leu Val
145                 150                 155                 160

Pro Val Pro Gln Tyr Pro Leu Tyr Ser Ala Thr Ile Ser Leu Leu Gly
            165                 170                 175

Gly Thr Leu Val Pro Tyr Tyr Leu Glu Glu Ser Glu Asn Trp Gly Leu
            180                 185                 190

Asp Val Asn Asn Leu Arg Gln Ser Val Ala Gln Ala Arg Ser Gln Gly
            195                 200                 205

Ile Thr Val Arg Ala Met Val Ile Ile Asn Pro Gly Asn Pro Thr Gly
210                 215                 220

Gln Cys Leu Ser Glu Ala Asn Ile Arg Glu Ile Leu Arg Phe Cys Cys
225                 230                 235                 240

Asp Glu Arg Leu Val Leu Leu Gly Asp Glu Val Tyr Gln Gln Asn Ile
            245                 250                 255

Tyr Gln Asp Glu Arg Pro Phe Ile Ser Ser Lys Lys Val Leu Met Asp
            260                 265                 270

Met Gly Ala Pro Ile Ser Lys Glu Val Gln Leu Ile Ser Phe His Thr
            275                 280                 285

Val Ser Lys Gly Tyr Trp Gly Glu Cys Gly Gln Arg Gly Gly Tyr Phe
290                 295                 300

Glu Met Thr Asn Ile Pro Pro Arg Thr Val Glu Glu Ile Tyr Lys Val
305                 310                 315                 320

Ala Ser Ile Ala Leu Ser Pro Asn Val Ser Ala Gln Ile Phe Met Gly
            325                 330                 335

Leu Met Val Ser Pro Pro Lys Pro Gly Asp Ile Ser Tyr Asp Gln Phe
            340                 345                 350

Val Arg Glu Ser Lys Gly Ile Leu Glu Ser Leu Arg Arg Arg Ala Arg
            355                 360                 365

Met Met Thr Asp Gly Phe Asn Ser Cys Lys Asn Val Val Cys Asn Phe
370                 375                 380

Thr Glu Gly Ala Met Tyr Ser Phe Pro Gln Ile Lys Leu Pro Ser Lys
385                 390                 395                 400

Ala Ile Gln Ala Ala Lys Gln Ala Gly Lys Val Pro Asp Val Phe Tyr
            405                 410                 415

Cys Leu Lys Leu Leu Glu Ala Thr Gly Ile Ser Thr Val Pro Gly Ser
            420                 425                 430

Gly Phe Gly Gln Lys Glu Gly Val Phe His Leu Arg Thr Thr Ile Leu
            435                 440                 445

Pro Ala Glu Glu Glu Met Pro Glu Ile Met Asp Ser Phe Lys Lys Phe
            450                 455                 460

Asn Asp Glu Phe Met Ser Gln Tyr Ala Asp Asn Phe Gly Tyr Ser Arg
465                 470                 475                 480

Met

<210> SEQ ID NO 14
<211> LENGTH: 398
<212> TYPE: PRT
<213> ORGANISM: Pyrococcus furiosus

<400> SEQUENCE: 14

Met Ile Arg Ala Ser Lys Arg Ala Leu Ser Val Glu Tyr Ala Ile Arg
1               5                   10                  15

Asp Val Val Leu Pro Ala Arg Glu Leu Glu Lys Lys Gly Ile Lys Val
            20                  25                  30
```

```
Ile Arg Leu Asn Ile Gly Asp Pro Val Lys Phe Asp Phe Gln Pro Pro
            35                  40                  45

Glu His Met Lys Glu Ala Tyr Cys Lys Ala Ile Lys Glu Gly His Asn
 50                  55                  60

Tyr Tyr Gly Asp Ser Glu Gly Leu Pro Glu Leu Arg Lys Ala Ile Val
 65                  70                  75                  80

Glu Arg Glu Lys Arg Lys Asn Gly Val Asp Ile Thr Pro Asp Val
                 85                  90                  95

Arg Val Thr Ala Ala Val Thr Glu Ala Leu Gln Leu Ile Phe Gly Ala
                100                 105                 110

Leu Leu Asp Pro Gly Asp Glu Ile Leu Val Pro Gly Pro Ser Tyr Pro
                115                 120                 125

Pro Tyr Thr Gly Leu Val Lys Phe Tyr Gly Lys Pro Val Glu Tyr
    130                 135                 140

Arg Thr Ile Glu Glu Asp Trp Gln Pro Asp Ile Asp Asp Ile Arg
145                 150                 155                 160

Lys Lys Ile Thr Asp Arg Thr Lys Ala Ile Ala Val Ile Asn Pro Asn
                165                 170                 175

Asn Pro Thr Gly Ala Leu Tyr Asp Lys Lys Thr Leu Glu Glu Ile Leu
                180                 185                 190

Asn Ile Ala Gly Glu Tyr Glu Ile Pro Val Ile Ser Asp Glu Ile Tyr
                195                 200                 205

Asp Leu Met Thr Tyr Glu Gly Glu His Ile Ser Pro Gly Ser Leu Thr
                210                 215                 220

Lys Asp Val Pro Val Ile Val Met Asn Gly Leu Ser Lys Val Tyr Phe
225                 230                 235                 240

Ala Thr Gly Trp Arg Leu Gly Tyr Met Tyr Phe Val Asp Pro Glu Asn
                245                 250                 255

Lys Leu Ser Glu Val Arg Glu Ala Ile Asp Arg Leu Ala Arg Ile Arg
                260                 265                 270

Leu Cys Pro Asn Thr Pro Ala Gln Phe Ala Ala Ile Ala Gly Leu Thr
                275                 280                 285

Gly Pro Met Asp Tyr Leu Lys Glu Tyr Met Lys Lys Leu Lys Glu Arg
                290                 295                 300

Arg Asp Tyr Ile Tyr Lys Arg Leu Asn Glu Ile Pro Gly Ile Ser Thr
305                 310                 315                 320

Thr Lys Pro Gln Gly Ala Phe Tyr Ile Phe Pro Lys Ile Glu Val Gly
                325                 330                 335

Pro Trp Lys Asn Asp Lys Glu Phe Val Leu Asp Val Leu His Asn Ala
                340                 345                 350

His Val Leu Phe Val His Gly Ser Gly Phe Gly Glu Tyr Gly Ala Gly
                355                 360                 365

His Phe Arg Ala Val Phe Leu Pro Pro Ile Glu Ile Leu Glu Glu Ala
                370                 375                 380

Met Asp Arg Phe Glu Lys Phe Met Lys Glu Arg Leu Lys Glu
385                 390                 395
```

<210> SEQ ID NO 15
<211> LENGTH: 496
<212> TYPE: PRT
<213> ORGANISM: Mus musculus

<400> SEQUENCE: 15

Met Ala Ser Gln Arg Asn Asp Arg Ile Gln Ala Ser Arg Asn Gly Leu

-continued

```
1               5                   10                  15
Lys Gly Lys Val Leu Thr Leu Asp Thr Met Asn Pro Cys Val Arg Arg
                20                  25                  30

Val Glu Tyr Ala Val Arg Gly Pro Ile Val Gln Arg Ala Leu Glu Leu
                35                  40                  45

Glu Gln Glu Leu Arg Gln Gly Val Lys Lys Pro Phe Thr Glu Val Ile
                50                  55                  60

Arg Ala Asn Ile Gly Asp Ala Gln Ala Met Gly Gln Arg Pro Ile Thr
65                  70                  75                  80

Phe Phe Arg Gln Val Leu Ala Leu Cys Val Tyr Pro Asn Leu Leu Ser
                85                  90                  95

Ser Pro Asp Phe Pro Glu Asp Ala Lys Arg Arg Ala Glu Arg Ile Leu
                100                 105                 110

Gln Ala Cys Gly Gly His Ser Leu Gly Ala Tyr Ser Ile Ser Ser Gly
                115                 120                 125

Ile Gln Pro Ile Arg Glu Asp Val Ala Gln Tyr Ile Glu Arg Arg Asp
                130                 135                 140

Gly Gly Ile Pro Ala Asp Pro Asn Asn Ile Phe Leu Ser Thr Gly Ala
145                 150                 155                 160

Ser Asp Ala Ile Val Thr Met Leu Lys Leu Leu Val Ala Gly Glu Gly
                165                 170                 175

Arg Ala Arg Thr Gly Val Leu Ile Pro Ile Pro Gln Tyr Pro Leu Tyr
                180                 185                 190

Ser Ala Ala Leu Ala Glu Leu Asp Ala Val Gln Val Asp Tyr Tyr Leu
                195                 200                 205

Asp Glu Glu Arg Ala Trp Ala Leu Asp Ile Ala Glu Leu Arg Arg Ala
                210                 215                 220

Leu Cys Gln Ala Arg Asp Arg Cys Cys Pro Arg Val Leu Cys Val Ile
225                 230                 235                 240

Asn Pro Gly Asn Pro Thr Gly Gln Val Gln Thr Arg Glu Cys Ile Glu
                245                 250                 255

Ala Val Ile Arg Phe Ala Phe Glu Glu Gly Leu Phe Leu Met Ala Asp
                260                 265                 270

Glu Val Tyr Gln Asp Asn Val Tyr Ala Glu Gly Ser Gln Phe His Ser
                275                 280                 285

Phe Lys Lys Val Leu Thr Glu Met Gly Pro Pro Tyr Ala Thr Gln Gln
                290                 295                 300

Glu Leu Ala Ser Phe His Ser Val Ser Lys Gly Tyr Met Gly Glu Cys
305                 310                 315                 320

Gly Phe Arg Gly Gly Tyr Val Glu Val Val Asn Met Asp Ala Glu Val
                325                 330                 335

Gln Lys Gln Met Ala Lys Leu Met Ser Val Arg Leu Cys Pro Pro Val
                340                 345                 350

Pro Gly Gln Ala Leu Met Gly Met Val Val Ser Pro Pro Thr Pro Ser
                355                 360                 365

Glu Pro Ser Phe Lys Gln Phe Gln Ala Glu Arg Gln Glu Val Leu Ala
                370                 375                 380

Glu Leu Ala Ala Lys Ala Lys Leu Thr Glu Gln Val Phe Asn Glu Ala
385                 390                 395                 400

Pro Gly Ile Arg Cys Asn Pro Val Gln Gly Ala Met Tyr Ser Phe Pro
                405                 410                 415

Gln Ile Gln Leu Pro Leu Lys Ala Val Gln Arg Ala Gln Asp Leu Gly
                420                 425                 430
```

Leu Ala Pro Asp Met Phe Phe Cys Leu Cys Leu Leu Glu Glu Thr Gly
        435                 440                 445

Ile Cys Val Val Pro Gly Ser Gly Phe Gly Gln Gln Glu Gly Thr Tyr
450                 455                 460

His Phe Arg Met Thr Ile Leu Pro Pro Met Glu Lys Leu Arg Val Leu
465                 470                 475                 480

Leu Glu Lys Leu Arg His Phe His Ala Lys Phe Thr His Glu Tyr Ser
            485                 490                 495

<210> SEQ ID NO 16
<211> LENGTH: 522
<212> TYPE: PRT
<213> ORGANISM: Mus musculus

<400> SEQUENCE: 16

Met Gln Arg Ala Ala Val Leu Val Arg Arg Gly Ser Cys Pro Arg Ala
1               5                   10                  15

Ser Gly Pro Trp Gly Arg Ser His Ser Ser Ala Ala Glu Ala Ser
            20                  25                  30

Ala Ala Leu Lys Val Arg Pro Glu Arg Ser Pro Arg Asp Arg Ile Leu
        35                  40                  45

Thr Leu Glu Ser Met Asn Pro Gln Val Lys Ala Val Glu Tyr Ala Val
50                  55                  60

Arg Gly Pro Ile Val Leu Lys Ala Gly Glu Ile Glu Met Glu Leu Gln
65                  70                  75                  80

Arg Gly Ile Lys Lys Pro Phe Thr Glu Val Ile Arg Ala Asn Ile Gly
            85                  90                  95

Asp Ala His Ala Met Gly Gln Gln Pro Ile Thr Phe Leu Arg Gln Val
        100                 105                 110

Met Ala Leu Cys Thr Tyr Pro Asn Leu Leu Asn Ser Pro Ser Phe Pro
    115                 120                 125

Glu Asp Ala Lys Lys Arg Ala Arg Arg Ile Leu Gln Ala Cys Gly Gly
    130                 135                 140

Asn Ser Leu Gly Ser Tyr Ser Ala Ser Gln Gly Val Asn Cys Ile Arg
145                 150                 155                 160

Glu Asp Val Ala Ala Phe Ile Thr Arg Arg Asp Gly Val Pro Ala Asp
                165                 170                 175

Pro Asp Asn Ile Tyr Leu Thr Thr Gly Ala Ser Asp Gly Ile Ser Thr
            180                 185                 190

Ile Leu Lys Leu Leu Val Ser Gly Gly Gly Lys Ser Arg Thr Gly Val
        195                 200                 205

Met Ile Pro Ile Pro Gln Tyr Pro Leu Tyr Ser Ala Val Ile Ser Glu
    210                 215                 220

Leu Asp Ala Val Gln Val Asn Tyr Tyr Leu Asp Glu Glu Asn Cys Trp
225                 230                 235                 240

Ala Leu Asn Val Asp Glu Leu Arg Arg Ala Leu Arg Gln Ala Lys Asp
                245                 250                 255

His Cys Asp Pro Lys Val Leu Cys Ile Ile Asn Pro Gly Asn Pro Thr
            260                 265                 270

Gly Gln Val Gln Ser Arg Lys Cys Ile Glu Asp Val Ile His Phe Ala
        275                 280                 285

Trp Glu Glu Lys Leu Phe Leu Leu Ala Asp Glu Val Tyr Gln Asp Asn
    290                 295                 300

Val Tyr Ser Pro Asp Cys Arg Phe His Ser Phe Lys Lys Val Leu Tyr

```
                305                 310                 315                 320
        Gln Met Gly His Glu Tyr Ser Ser Asn Val Glu Leu Ala Ser Phe His
                        325                 330                 335

Ser Thr Ser Lys Gly Tyr Met Gly Glu Cys Gly Tyr Arg Gly Gly Tyr
                        340                 345                 350

Met Glu Val Ile Asn Leu His Pro Glu Ile Lys Gly Gln Leu Val Lys
                        355                 360                 365

Leu Leu Ser Val Arg Leu Cys Pro Pro Val Ser Gly Gln Ala Ala Met
                        370                 375                 380

Asp Ile Val Val Asn Pro Pro Glu Pro Gly Glu Ser Phe Glu Gln
        385                 390                 395                 400

Phe Ser Arg Glu Lys Glu Phe Val Leu Gly Asn Leu Ala Lys Lys Ala
                        405                 410                 415

Lys Leu Thr Glu Asp Leu Phe Asn Gln Val Pro Gly Ile Gln Cys Asn
                        420                 425                 430

Pro Leu Gln Gly Ala Met Tyr Ala Phe Pro Arg Ile Leu Ile Pro Ala
                        435                 440                 445

Lys Ala Val Glu Ala Ala Gln Ser His Lys Met Ala Pro Asp Met Phe
                        450                 455                 460

Tyr Cys Met Lys Leu Leu Glu Glu Thr Gly Ile Cys Val Val Pro Gly
        465                 470                 475                 480

Ser Gly Phe Gly Gln Arg Glu Gly Thr Tyr His Phe Arg Met Thr Ile
                        485                 490                 495

Leu Pro Pro Val Asp Lys Leu Lys Thr Val Leu His Lys Val Lys Asp
                        500                 505                 510

Phe His Leu Lys Phe Leu Glu Gln Tyr Ser
                        515                 520

<210> SEQ ID NO 17
<211> LENGTH: 496
<212> TYPE: PRT
<213> ORGANISM: Homo sapiens

<400> SEQUENCE: 17

Met Ala Ser Ser Thr Gly Asp Arg Ser Gln Ala Val Arg His Gly Leu
        1               5                   10                  15

Arg Ala Lys Val Leu Thr Leu Asp Gly Met Asn Pro Arg Val Arg Arg
                        20                  25                  30

Val Glu Tyr Ala Val Arg Gly Pro Ile Val Gln Arg Ala Leu Glu Leu
                        35                  40                  45

Glu Gln Glu Leu Arg Gln Gly Val Lys Lys Pro Phe Thr Glu Val Ile
                        50                  55                  60

Arg Ala Asn Ile Gly Asp Ala Gln Ala Met Gly Gln Arg Pro Ile Thr
        65                  70                  75                  80

Phe Leu Arg Gln Val Leu Ala Leu Cys Val Asn Pro Asp Leu Leu Ser
                        85                  90                  95

Ser Pro Asn Phe Pro Asp Asp Ala Lys Lys Arg Ala Glu Arg Ile Leu
                        100                 105                 110

Gln Ala Cys Gly Gly His Ser Leu Gly Ala Tyr Ser Val Ser Ser Gly
                        115                 120                 125

Ile Gln Leu Ile Arg Glu Asp Val Ala Arg Tyr Ile Glu Arg Arg Asp
                        130                 135                 140

Gly Gly Ile Pro Ala Asp Pro Asn Asn Val Phe Leu Ser Thr Gly Ala
        145                 150                 155                 160
```

Ser Asp Ala Ile Val Thr Val Leu Lys Leu Leu Val Ala Gly Glu Gly
            165                 170                 175

His Thr Arg Thr Gly Val Leu Ile Pro Ile Pro Gln Tyr Pro Leu Tyr
            180                 185                 190

Ser Ala Thr Leu Ala Glu Leu Gly Ala Val Gln Val Asp Tyr Tyr Leu
            195                 200                 205

Asp Glu Glu Arg Ala Trp Ala Leu Asp Val Ala Glu Leu His Arg Ala
            210                 215                 220

Leu Gly Gln Ala Arg Asp His Cys Arg Pro Arg Ala Leu Cys Val Ile
225                 230                 235                 240

Asn Pro Gly Asn Pro Thr Gly Gln Val Gln Thr Arg Glu Cys Ile Glu
            245                 250                 255

Ala Val Ile Arg Phe Ala Phe Glu Glu Arg Leu Phe Leu Leu Ala Asp
            260                 265                 270

Glu Val Tyr Gln Asp Asn Val Tyr Ala Ala Gly Ser Gln Phe His Ser
            275                 280                 285

Phe Lys Lys Val Leu Met Glu Met Gly Pro Pro Tyr Ala Gly Gln Gln
            290                 295                 300

Glu Leu Ala Ser Phe His Ser Thr Ser Lys Gly Tyr Met Gly Glu Cys
305                 310                 315                 320

Gly Phe Arg Gly Gly Tyr Val Glu Val Val Asn Met Asp Ala Ala Val
            325                 330                 335

Gln Gln Gln Met Leu Lys Leu Met Ser Val Arg Leu Cys Pro Pro Val
            340                 345                 350

Pro Gly Gln Ala Leu Leu Asp Leu Val Val Ser Pro Pro Ala Pro Thr
            355                 360                 365

Asp Pro Ser Phe Ala Gln Phe Gln Ala Glu Lys Gln Ala Val Leu Ala
            370                 375                 380

Glu Leu Ala Ala Lys Ala Lys Leu Thr Glu Gln Val Phe Asn Glu Ala
385                 390                 395                 400

Pro Gly Ile Ser Cys Asn Pro Val Gln Gly Ala Met Tyr Ser Phe Pro
            405                 410                 415

Arg Val Gln Leu Pro Pro Arg Ala Val Glu Arg Ala Gln Glu Leu Gly
            420                 425                 430

Leu Ala Pro Asp Met Phe Phe Cys Leu Arg Leu Leu Glu Glu Thr Gly
            435                 440                 445

Ile Cys Val Val Pro Gly Ser Gly Phe Gly Gln Arg Glu Gly Thr Tyr
            450                 455                 460

His Phe Arg Met Thr Ile Leu Pro Pro Leu Glu Lys Leu Arg Leu Leu
465                 470                 475                 480

Leu Glu Lys Leu Ser Arg Phe His Ala Lys Phe Thr Leu Glu Tyr Ser
            485                 490                 495

<210> SEQ ID NO 18
<211> LENGTH: 523
<212> TYPE: PRT
<213> ORGANISM: Homo sapiens

<400> SEQUENCE: 18

Met Gln Arg Ala Ala Ala Leu Val Arg Arg Gly Cys Gly Pro Arg Thr
1               5                   10                  15

Pro Ser Ser Trp Gly Arg Ser Gln Ser Ala Ala Ala Glu Ala Ser
            20                  25                  30

Ala Val Leu Lys Val Arg Pro Glu Ser Arg Arg Glu Arg Ile Leu
            35                  40                  45

```
Thr Leu Glu Ser Met Asn Pro Gln Val Lys Ala Val Glu Tyr Ala Val
 50                  55                  60

Arg Gly Pro Ile Val Leu Lys Ala Gly Glu Ile Glu Leu Glu Leu Gln
 65                  70                  75                  80

Arg Gly Ile Lys Lys Pro Phe Thr Glu Val Ile Arg Ala Asn Ile Gly
             85                  90                  95

Asp Ala Gln Ala Met Gly Gln Gln Pro Ile Thr Phe Leu Arg Gln Val
            100                 105                 110

Met Ala Leu Cys Thr Tyr Pro Asn Leu Leu Asp Ser Pro Ser Phe Pro
            115                 120                 125

Glu Asp Ala Lys Lys Arg Ala Arg Arg Ile Leu Gln Ala Cys Gly Gly
130                 135                 140

Asn Ser Leu Gly Ser Tyr Ser Ala Ser Gln Gly Val Asn Cys Ile Arg
145                 150                 155                 160

Glu Asp Val Ala Ala Tyr Ile Thr Arg Asp Gly Gly Val Pro Ala
                165                 170                 175

Asp Pro Asp Asn Ile Tyr Leu Thr Thr Gly Ala Ser Asp Gly Ile Ser
            180                 185                 190

Thr Ile Leu Lys Ile Leu Val Ser Gly Gly Lys Ser Arg Thr Gly
            195                 200                 205

Val Met Ile Pro Ile Pro Gln Tyr Pro Leu Tyr Ser Ala Val Ile Ser
210                 215                 220

Glu Leu Asp Ala Ile Gln Val Asn Tyr Tyr Leu Asp Glu Glu Asn Cys
225                 230                 235                 240

Trp Ala Leu Asn Val Asn Glu Leu Arg Arg Ala Val Gln Glu Ala Lys
                245                 250                 255

Asp His Cys Asp Pro Lys Val Leu Cys Ile Ile Asn Pro Gly Asn Pro
            260                 265                 270

Thr Gly Gln Val Gln Ser Arg Lys Cys Ile Glu Asp Val Ile His Phe
            275                 280                 285

Ala Trp Glu Glu Lys Leu Phe Leu Leu Ala Asp Glu Val Tyr Gln Asp
290                 295                 300

Asn Val Tyr Ser Pro Asp Cys Arg Phe His Ser Phe Lys Lys Val Leu
305                 310                 315                 320

Tyr Glu Met Gly Pro Glu Tyr Ser Ser Asn Val Glu Leu Ala Ser Phe
                325                 330                 335

His Ser Thr Ser Lys Gly Tyr Met Gly Glu Cys Gly Tyr Arg Gly Gly
            340                 345                 350

Tyr Met Glu Val Ile Asn Leu His Pro Glu Ile Lys Gly Gln Leu Val
            355                 360                 365

Lys Leu Leu Ser Val Arg Leu Cys Pro Pro Val Ser Gly Gln Ala Ala
370                 375                 380

Met Asp Ile Val Val Asn Pro Pro Val Ala Gly Glu Glu Ser Phe Glu
385                 390                 395                 400

Gln Phe Ser Arg Glu Lys Glu Ser Val Leu Gly Asn Leu Ala Lys Lys
                405                 410                 415

Ala Lys Leu Thr Glu Asp Leu Phe Asn Gln Val Pro Gly Ile His Cys
            420                 425                 430

Asn Pro Leu Gln Gly Ala Met Tyr Ala Phe Pro Arg Ile Phe Ile Pro
            435                 440                 445

Ala Lys Ala Val Glu Ala Ala Gln Ala His Gln Met Ala Pro Asp Met
450                 455                 460
```

```
Phe Tyr Cys Met Lys Leu Leu Glu Glu Thr Gly Ile Cys Val Val Pro
465                 470                 475                 480

Gly Ser Gly Phe Gly Gln Arg Glu Gly Thr Tyr His Phe Arg Met Thr
            485                 490                 495

Ile Leu Pro Pro Val Glu Lys Leu Lys Thr Val Leu Gln Lys Val Lys
        500                 505                 510

Asp Phe His Ile Asn Phe Leu Glu Lys Tyr Ala
        515                 520
```

```
<210> SEQ ID NO 19
<211> LENGTH: 20
<212> TYPE: DNA
<213> ORGANISM: Artificial Sequence
<220> FEATURE:
<223> OTHER INFORMATION: Forward PCR primer HvAlaAT

<400> SEQUENCE: 19
gaggttcttg ccctttgtga                                              20

<210> SEQ ID NO 20
<211> LENGTH: 19
<212> TYPE: DNA
<213> ORGANISM: Artificial Sequence
<220> FEATURE:
<223> OTHER INFORMATION: Reverse PCR primer HvAlaAT

<400> SEQUENCE: 20
ttcagctcgt tgcaagtaa                                               19

<210> SEQ ID NO 21
<211> LENGTH: 20
<212> TYPE: DNA
<213> ORGANISM: Artificial Sequence
<220> FEATURE:
<223> OTHER INFORMATION: Forward PCR primer MmAlaAT1

<400> SEQUENCE: 21
ccagaggatg ccaagagaag                                              20

<210> SEQ ID NO 22
<211> LENGTH: 20
<212> TYPE: DNA
<213> ORGANISM: Artificial Sequence
<220> FEATURE:
<223> OTHER INFORMATION: Reverse PCR primer MmAlaAT1

<400> SEQUENCE: 22
gctccgtgag tttagccttg                                              20

<210> SEQ ID NO 23
<211> LENGTH: 18
<212> TYPE: DNA
<213> ORGANISM: Artificial Sequence
<220> FEATURE:
<223> OTHER INFORMATION: Forward PCR primer MmAlaAT2

<400> SEQUENCE: 23
gcaggcttgt ggtggaaa                                                18

<210> SEQ ID NO 24
<211> LENGTH: 24
<212> TYPE: DNA
<213> ORGANISM: Artificial Sequence
<220> FEATURE:
<223> OTHER INFORMATION: Reverse PCR primer MmAlaAT2
```

```
<400> SEQUENCE: 24
gcactttctt aaaggagtgg aatc                                              24

<210> SEQ ID NO 25
<211> LENGTH: 26
<212> TYPE: DNA
<213> ORGANISM: Artificial Sequence
<220> FEATURE:
<223> OTHER INFORMATION: Forward PCR primer PfAlaAT

<400> SEQUENCE: 25
gcgctctacg acaaaaagac acttga                                            26

<210> SEQ ID NO 26
<211> LENGTH: 26
<212> TYPE: DNA
<213> ORGANISM: Artificial Sequence
<220> FEATURE:
<223> OTHER INFORMATION: Reverse PCR primer PfAlaAT

<400> SEQUENCE: 26
cgttagtcct gctatagctg cgaatt                                            26
```